US008288423B2

(12) United States Patent
Cho et al.

(10) Patent No.: US 8,288,423 B2
(45) Date of Patent: Oct. 16, 2012

(54) FXA INHIBITORS WITH CYCLIC AMIDINES AS P4 SUBUNIT, PROCESSES FOR THEIR PREPARATIONS, AND PHARMACEUTICAL COMPOSITIONS AND DERIVATIVES THEREOF

(75) Inventors: Young Lag Cho, Daejeon (KR); Ho Young Song, Daejeon (KR); Dae Yon Lee, Daejeon (KR); Sung Yoon Baek, Daejeon (KR); Sang Eun Chae, Daejeon (KR); Sang Hui Jo, Daejeon (KR); Yeon Ok Kim, Daejeon (KR); Hyang Sook Lee, Daejeon (KR); Ju Hyun Park, Daejeon (KR); Tae Kyo Park, Daejeon (KR); Sung Ho Woo, Daejeon (KR); Yong Zu Kim, Daejeon (KR)

(73) Assignee: Legochem Bioscience Ltd., Daejeon (KR)

( * ) Notice: Subject to any disclaimer, the term of this patent is extended or adjusted under 35 U.S.C. 154(b) by 445 days.

(21) Appl. No.: 12/598,010

(22) PCT Filed: May 9, 2008

(86) PCT No.: PCT/KR2008/002619
§ 371 (c)(1),
(2), (4) Date: Oct. 28, 2009

(87) PCT Pub. No.: WO2008/140220
PCT Pub. Date: Nov. 20, 2008

(65) Prior Publication Data
US 2010/0184781 A1 Jul. 22, 2010

(30) Foreign Application Priority Data

May 9, 2007 (KR) .......................... 10-2007-0044980
May 8, 2008 (KR) .......................... 10-2008-0042740

(51) Int. Cl.
| A01N 43/64 | (2006.01) |
| A01N 43/76 | (2006.01) |
| A01N 43/50 | (2006.01) |
| A01N 43/02 | (2006.01) |
| A01N 43/06 | (2006.01) |
| A61K 31/41 | (2006.01) |
| A61K 31/42 | (2006.01) |
| A61K 31/415 | (2006.01) |
| A61K 31/38 | (2006.01) |

(52) U.S. Cl. ........ 514/359; 514/374; 514/385; 514/430; 514/438

(58) Field of Classification Search .................. 514/359, 514/374, 385, 430, 438
See application file for complete search history.

(56) References Cited

U.S. PATENT DOCUMENTS
2004/0242660 A1 12/2004 Straub et al.

FOREIGN PATENT DOCUMENTS
| WO | 99/31092 A1 | 6/1999 |
| WO | 01/47919 A1 | 7/2001 |

*Primary Examiner* — Yong S. Chong
(74) *Attorney, Agent, or Firm* — Sughrue Mion, PLLC

(57) ABSTRACT

The present invention relates to novel oxazolidinone derivatives with cyclic amidines, and prodrugs, hydrates, solvates, isomers and pharmaceutically acceptable salts thereof, and processes for preparing the same, and pharmaceutical compositions comprising the same. The oxazolidinone derivatives with cyclic amidines, and prodrugs, hydrates, solvates, isomers and pharmaceutically acceptable salts thereof can be usefully employed as an anticoagulant for treating thromboembolism and tumors via inhibition of coagulation factor Xa.

8 Claims, 1 Drawing Sheet

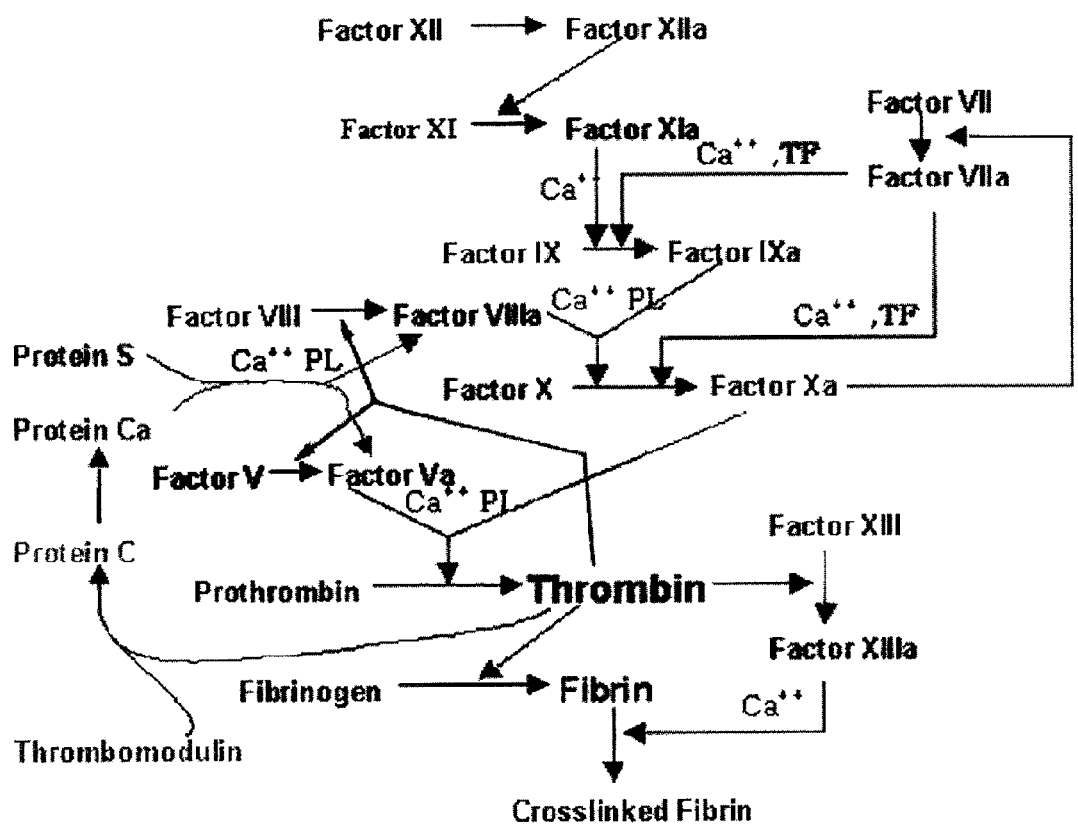

FXA INHIBITORS WITH CYCLIC AMIDINES AS P4 SUBUNIT, PROCESSES FOR THEIR PREPARATIONS, AND PHARMACEUTICAL COMPOSITIONS AND DERIVATIVES THEREOF

TECHNICAL FIELD

The present invention relates to novel oxazolidinone derivatives with cyclic amidines, represented by Chemical Formula (1), and prodrugs, hydrates, solvates, isomers and pharmaceutically acceptable salts thereof, and processes for preparing the same, and pharmaceutical compositions comprising the same.

[Chemical Formula 1]

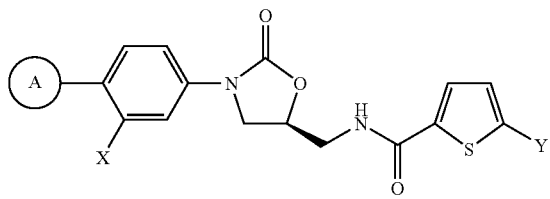

In Chemical Formula (1), A is selected from the following structures.

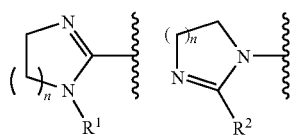

The antithrombotic and anticoagulant activities of the novel oxazolidinone derivatives with cyclic amidines, represented by Chemical Formula (1) according to the present invention result from inhibition against activated coagulation protease known as factor Xa, or inhibition of other activated serine proteases such as factor Xa, factor IXa or thrombin.

BACKGROUND ART

The blood coagulation factors are distributed in plasma, with various types of factors from $1^{st}$ coagulation factor to $13^{th}$ coagulation factor working sequentially to result in blood coagulation. The mechanism wherein individual blood coagulation factors participate in blood coagulation is shown in FIG. 1.

As illustrated in FIG. 1, blood coagulation is accomplished through very delicate and complex processes wherein reactions occur sequentially. In general, inactive precursors are activated by certain activated coagulation factors (indicated by "a" at the end of the designation of the coagulation factor), and then the coagulation factors are activated. Most of the activated coagulation factors are enzymes called serine protease. These bind to the surface of platelets to sequentially activate the blood coagulation factors to finally create fibrin clot to complete hemostasis.

Thrombin plays the most important role among them. Thrombin is activated from prothrombin (the precursor) via prothrombinase complex consisting of Va factor, Xa factor, Ca++ and phospholipids (PL). When fibrinogen is converted into fibrin thereby, fibrins are crosslinked by the activated XIIIa factor to finally provide stabilized fibrin clot.

In order to form prothrombinase complex, X factor should be activated to Xa factor; this occurs by means of factor Xase complex. Factors produced via intrinsic pathway such as VIIIa factor, IXa factor, Ca++ and phospholipids (PL), or factors produced via extrinsic pathway such as VIIa factor, tissue factor (TF) and Ca++ serve as the factor Xase complex.

In the meanwhile, thrombin functions to activate V factor and VIII factor. If thrombin is excessively generated, problem of vaso-occlusion may occur. In order to control such a problem, thrombin would run a process for inhibiting blood coagulation. Thus, thrombin binds to thrombomodulin to activate protein C to generate protein Ca, which will bind to protein S to inactivate the activated Va and VIIIa factors.

Factor Xa is one of the proteases associated with complex processes of blood coagulation, catalyzing conversion of prothrombin into thrombin. Thrombin crosslinks with fibrinogen, and then decompose it into fibrin monomer which essentially contributes thrombus formation. Activation of thrombin may induce thromboembolism. However, inhibition of thrombin may inhibit formation of fibrin which is associated with thrombus formation.

Thus, inhibition of factor Xa may prevent formation of thrombin, and the compounds of Chemical Formula (1) according to the present invention and salts thereof inhibit factor Xa, to participate in the processes of blood coagulation, thereby inhibiting thrombus formation.

Among the compounds known as factor Xa inhibitors up to the present, protein inhibitors are antistasin (ATS), tick anticoagulant peptide (TAP), and the like. ATS is a compound consisting of 119 amino acids, obtained from leeches, having Ki value for factor Xa of 0.05 nM, while TAP is a compound consisting of 60 amino acids having Ki value for factor Xa of 0.5 nM. Those protein inhibitors are not employed in clinical practices at present, while heparin, sulfated polysaccharides, or the like is rarely employed with limitation.

Development of inhibitors against blood coagulation, particularly factor Xa inhibitors, as a low molecular compound was disclosed by WO9529189. Factor Xa inhibitors employing indole derivatives are described in WO9933800. Various types of factor Xa inhibitors have been reported, including nitrogen-containing heterocyclic compounds (WO2004058743), imidazole derivatives (WO2004050636), pyrazole derivatives (WO2004056815), indole-2-carboxamide derivatives (WO2003044014), oxybenzamide derivatives (WO2002051831), guanidine and amidine derivatives (WO2002046159), amino-bicyclic pyrazinone and pyridinone derivatives (WO2004002405).

However, those low molecular compounds have to overcome the problems to meet stability in plasma and liver, selectivity from other serine proteases (thrombin, trypsin, cathepsin G, or the like), low toxicity and high bioavailability, as well as high pharmaceutical activity.

The most advanced one among the oxazolidinone type compounds similar to those of the present invention up to the present is Rivaroxaban represented by Chemical Formula (A), of which clinical studies in three aspects are now on progress. Likewise, oxazolidinone derivatives represented by Chemical Formula (B) are disclosed by WO 01/47917. Those compounds, however, have limited solubility yet: for example, about 8 mg/L of solubility for Rivaroxaban. Improvement in this regard is considerably required.

[Chemical Formula A]

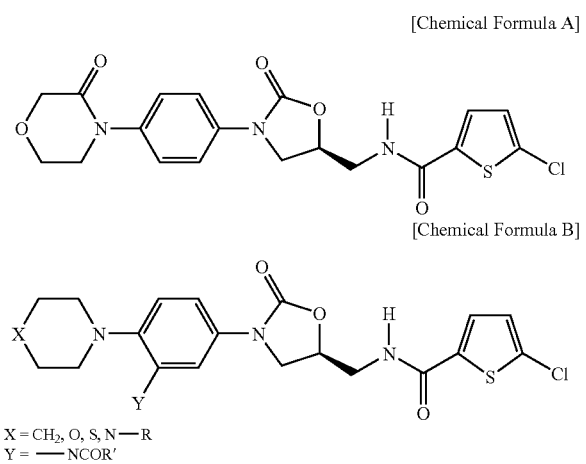

[Chemical Formula B]

X = CH₂, O, S, N—R
Y = —NCOR'

Furthermore, factor Xa inhibitors using Apixaban derivatives represented by Chemical Formula (C) with cyclic amidine group being incorporated or sulfonyl amidine derivatives represented by Chemical Formula (D) were disclosed in WO 2004/83174. However, oxazolidinone derivatives with cyclic amidines (compounds of the present invention) have not been used in this regard.

[Chemical Formula C]

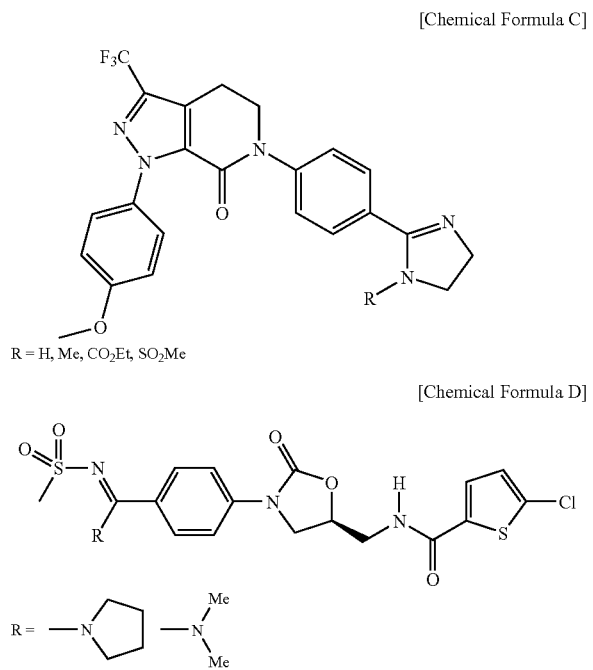

R = H, Me, CO₂Et, SO₂Me

[Chemical Formula D]

The keypoint of the studies on FXa inhibitors and thrombin inhibitors in the same cascade having been known up to the present is on the inhibitor comprising P1 group containing benzamidine as an arginine derivative. Since both FXa and thrombin comprise arginine at P1 position, they have similar features of problems. The amidine (including guanidine derivatives) groups which replaces the guanidine moiety of arginine is very hydrophilic, so that most inhibitors containing the groups result in poor or insufficient absorption, and even though they are once absorbed, they frequently exhibit short half-life due to the specific property of high clearance (Drugs of the Future, 1999, 24(7), 771).

Amidine itself has strongly basic structure with the PKa of about 12.5. Considering that insufficient absorbance comes from tendency of being positively charged, replacements with derivatives with low basicity have been tried. Representatives include pyridine derivatives, amidrazone, cyclic amines, alkylamine derivatives, aminobenzisoxazole, and the like (U.S. Pat. No. 6,958,356), and a representative example of investigations to replace the amidine with other derivatives is replacement of amidine with amidoxime. Amidoxim has a structure with hydroxyl group attached to amidine itself, being a prodrug taking advantage that weak N—O bond is easily reduced to amidine in vivo. On the base, it makes use of the fact that PKa of amidoxime (about 8-9) is noticeably lower than that of amidine. Representative example of amidoximes is ximelagatran. Such a tendency is equivalently observed in the studies on FXa inhibitors as well as on thrombin inhibitors. When such various trials face limitations, incorporation of neutral P1 group has been rather tried. However, being different from other drug substances, FXa and thrombin inhibitors are advantageous as the blood concentration increases, and the free drug concentration, without binding with protein in blood, is a very important field. In case of neutral P1 group inhibitor, the pharmacological effect rarely appears because the protein binding is relatively high.

In order to solve the problems described above, the present inventors tried to incorporate a relatively polar group at the other site of the inhibitor, instead of limiting P1 group to neutral groups, in order to 1) improve water solubility and 2) lower the protein binding. Lowered protein binding usually provides beneficial effects in PT assay. Practically, lowered protein binding can be indirectly checked by excellent PT value, in spite of relatively low binding affinity to FXa. Thus, the inventors have proceeded with the studies for increasing pharmacological effect by reducing the protein binding.

The position for incorporation of polar group according to the invention is P4 site. The theoretical background is described below. The S4 site of FXa comprises the binding site of "⊂"-shape with three sides have been surrounded by Tyr99, Phe174 and Trp215. Since the binding site consists only of aromatic amino acid side chains, it is basically different from thrombin surrounded by Leu99, Ile174 and Trp215. During the course of drug design, such differences are positively utilized.

The S4 pocket of FXa has high tendency of interaction with cationic residue, which is usually called "π-cation interaction". In practice, some inhibitors have been designed and synthesized as a positively charged group at P4 site. The present invention intends to enhance the pharmacological effect by improving water solubility and lowering the protein binding, as described above, via incorporation of cyclic amidines at P4 site. The reason for selecting cyclic amidine rather than non-substituted amidine is that amidine has three NH bonds (substantially four in biological PH) so that it negatively acts in terms of drug-likeness, while a cyclic amidine having 0 to 1 NH group is advantageous from the same aspect. According to recent investigations, it is more advantageous if the number of pharmaceutically acceptable hydrogen bond donor (HBD) decreases less than that of hydrogen bond acceptor (HBA). According to Lipinski's rule, up to ten (10) HBA's are acceptable, but the number of HBD is restricted to five (5) (Adv. Drug Delivery Rev., 2001, 46, 3-26). Average HBD value of known new drugs is about 1.8—being relatively strict on HBD (J. Med. Chem. 2004, 47, 6338-48). From this point of view, it is anticipated that a substituted cyclic amidine (number of HBD=0) is far advantageous as compared to an unsubstituted amidine (number of HBD=3). Though a substituted amidine has noticeably decreased number of NH, the amidine functional group itself still has positive charge, so that separation-purification-storage can be done in salt state, thereby having excellent water solubility.

From the studies of the present invention, these features of compounds of Chemical Formula (1) were practically confirmed. In the experiment section, the water solubility and protein binding values, as well as 2×PT value versus Ki are diagrammed.

DISCLOSURE

Technical Problem

The present inventors synthesized novel oxazolidinone derivatives with cyclic amidines having useful properties, which can be applied to preparations of pharmaceutical Particularly, since the oxazolidinone derivatives with cyclic amidines exhibit factor Xa-inhibiting property, they can be used for treating or preventing thrombosis, myocardial infarction, arteriosclerosis, inflammation, cerebral apoplexy, angina pectoris, recurrent stricture after angioplasty, and thromboembolism such as intermittent claudication. Further, the oxazolidinone derivatives with cyclic amidines according to the present invention may function as an inhibitor against factor VIIIa, factor IXa and thrombin as coagulation factors in a blood coagulation cascade.

Thus, the object of the invention is to provide oxazolidinone derivatives with cyclic amidines exhibiting factor Xa-inhibiting property, and prodrugs, hydrates, solvates, isomers and pharmaceutically acceptable salts thereof.

Another object of the invention is to provide anticoagulant pharmaceutical composition containing oxazolidinone derivatives with cyclic amidines, and prodrugs, hydrates, solvates, isomers and pharmaceutically acceptable salts thereof, as an active ingredient.

Still another object of the invention is to provide pharmaceutical compositions comprising oxazolidinone derivatives with a cyclic amidines, prodrugs, hydrates, solvates, isomers and pharmaceutically acceptable salts thereof, as an active ingredient, for treating or preventing thrombosis, myocardial infarction, arteriosclerosis, inflammation, cerebral apoplexy, angina pectoris, recurrent stricture, intermittent claudication, phlebothrombosis, pulmonary embolism, arterial thrombosis, myocardial ischemia or thromboembolism.

Still another object of the invention is to provide pharmaceutical compositions comprising oxazolidinone derivatives with a cyclic amidines, prodrugs, hydrates, solvates, isomers and pharmaceutically acceptable salts thereof, in combination with a thrombolytic drug, for treating or preventing diseases in coronary, cerebral or peripheral arteries.

Still another object of the invention is to provide use of oxazolidinone derivatives with cyclic amidines, prodrugs, hydrates, solvates, isomers and pharmaceutically acceptable salts thereof, as an anticoagulant for preserving blood, plasma or blood products in vitro.

Technical Solution

The present invention relates to novel oxazolidinone derivatives with cyclic amidines, represented by Chemical Formula (1), and prodrugs, hydrates, solvates, isomers and pharmaceutically acceptable salts thereof, and processes for preparing the same, and pharmaceutical compositions comprising the same.

[Chemical Formula 1]

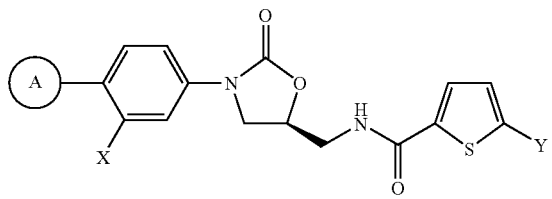

[In Chemical Formula (1), A is selected from the following structures:

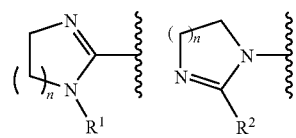

X represents hydrogen or halogen;

Y represents halogen;

$R^1$ and $R^2$ independently represent hydrogen, $(C_1-C_7)$ alkyl, $(C_3-C_{12})$cycloalkyl, a 5- to 7-membered heterocycloalkyl containing one or more heteroatom(s) selected from N, O and S, $(C_1-C_7)$alkyl containing one or more heteroatom(s) selected from N, O and S, $(C_6R_{12})$aryl, $(C_4-C_{12})$heteroaryl, $-(CR^{11}R^{12})_mCO-R^{13}$, $-(CR^{11}R^{12})_mSO_2-R^{14}$ or $-(CR^{11}R^{12})_mCR^{21}=CR^{22}R^{23}$ containing one or more heteroatom(s) selected from N, O and S; and the alkyl, cycloalkyl, aryl or heteroaryl of $R^1$ and $R^2$ may be further substituted by one or more substituent(s) selected from $(C_1-C_7)$ alkyl, halo $(C_1-C_7)$ alkyl, $(C_1-C_7)$ alkoxy and halogen;

$R^{11}$ and $R^{12}$ independently represent hydrogen or $(C_1-C_7)$ alkyl, or they may be linked via $(C_2-C_5)$alkylene to form a ring;

$R^{13}$ and $R^{14}$ independently represent hydrogen, $(C_1-C_7)$ alkyl or $(C_1-C_7)$ alkoxy;

$R^{21}$ through $R^{23}$ independently represent hydrogen or $(C_1-C_7)$ alkyl, m represents an integer from 0 to 3; and n represents an integer from 1 to 3.]

Preferable examples of the oxazolidinone derivatives with cyclic amidines, represented by Chemical Formula (1) according to the invention include compounds represented by one of Chemical Formulas (2) and (3):

[Chemical Formula 2]

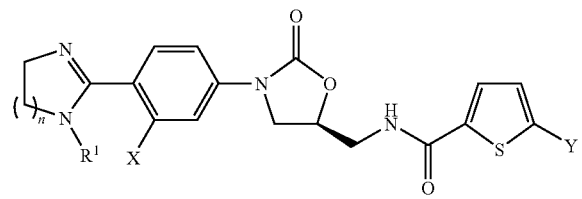

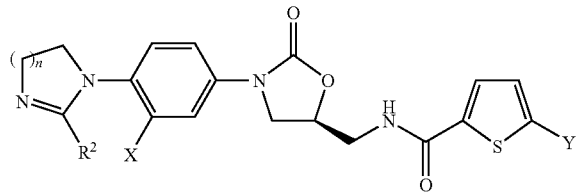

[wherein, $R^1$ and $R^2$ are defined as in Chemical Formula (1);

X represents hydrogen, F or Cl;

Y represents Cl or Br; and n is an integer of 1 or 2.]

In the preferable oxazolidinone derivatives with cyclic amidines according to the invention, $R^1$ and $R^2$ independently represent hydrogen, methyl, ethyl, n-propyl, i-propyl, n-butyl, i-butyl, t-butyl, cyclopropyl, cyclobutyl, allyl, methylcarbonyl, methylsulfonyl, or a substituent selected from the following structures; and n is 1 or 2:

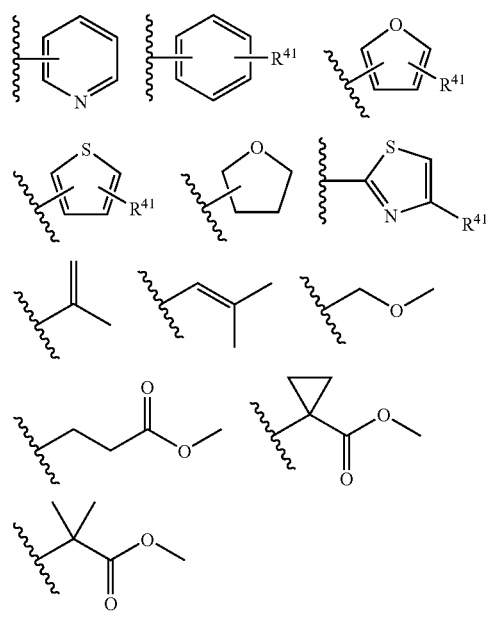

[wherein, $R^{41}$ represents hydrogen, $(C_1-C_7)$alkyl, halo$(C_1-C_7)$alkyl or halogen.]

The oxazolidinone derivatives with cyclic amidines according to the invention can be exemplified by the following compounds, but the invention is not restricted thereto.

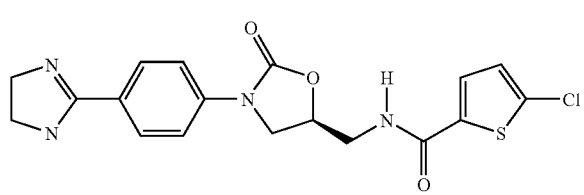

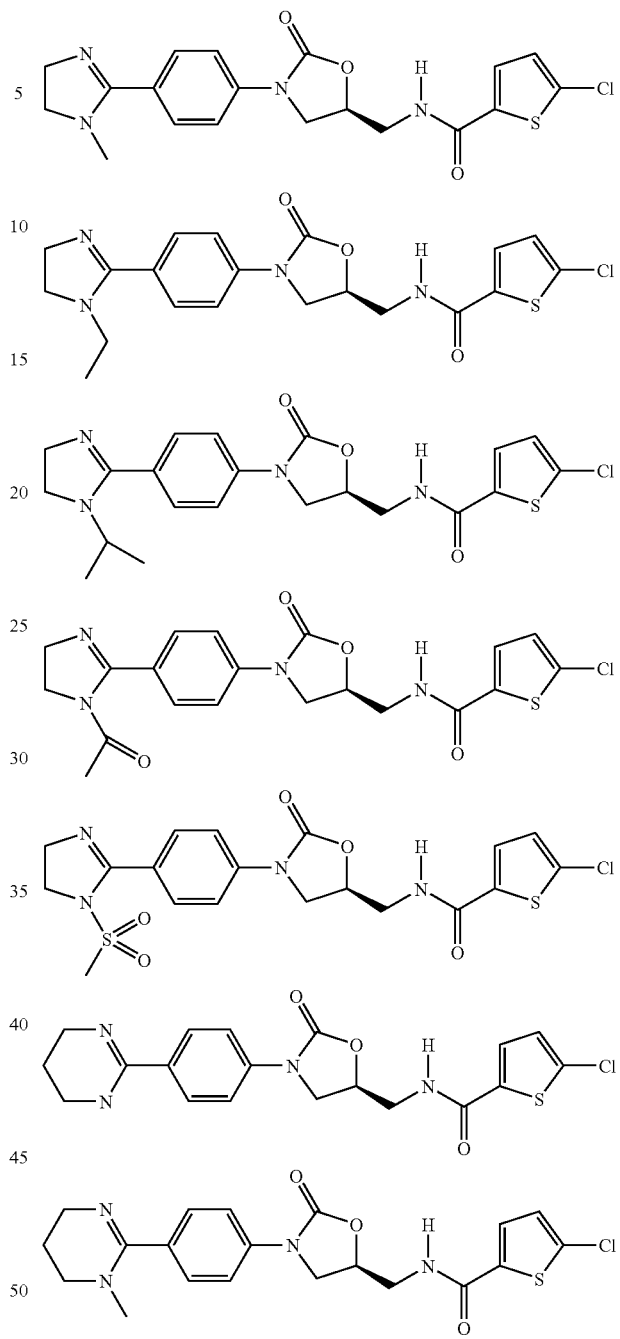

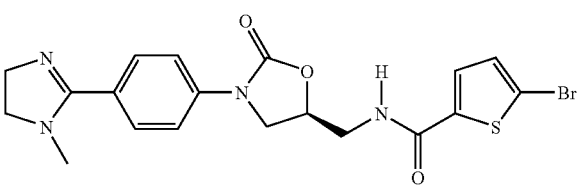

-continued
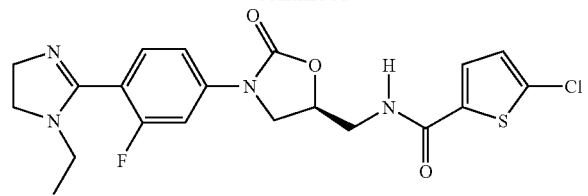
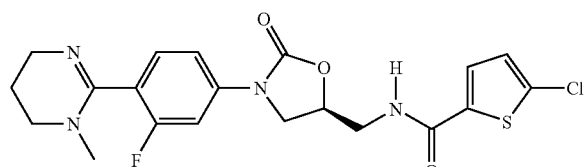
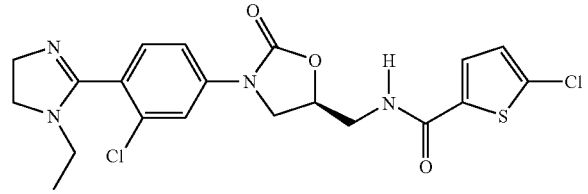
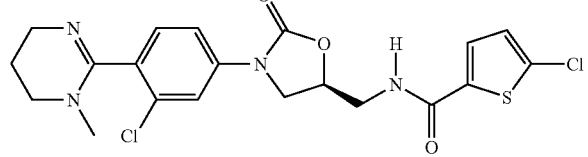
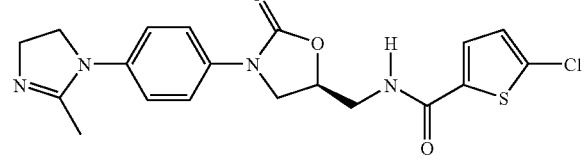
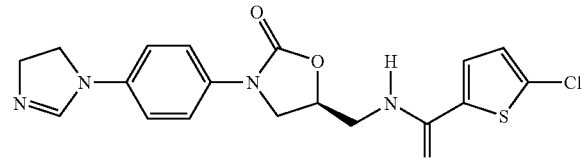
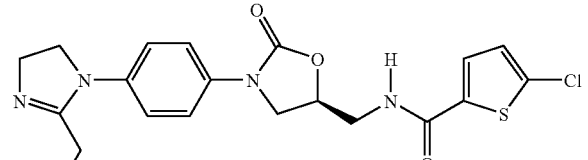
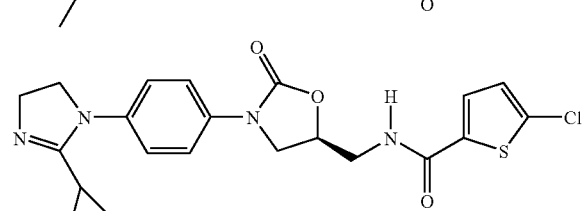
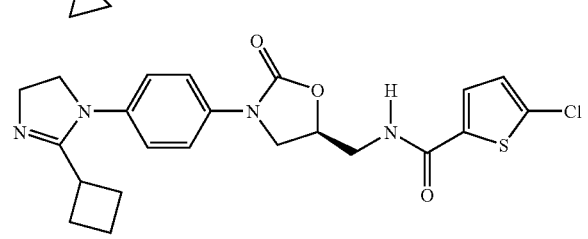
-continued
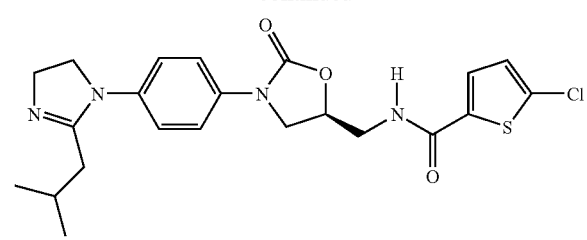
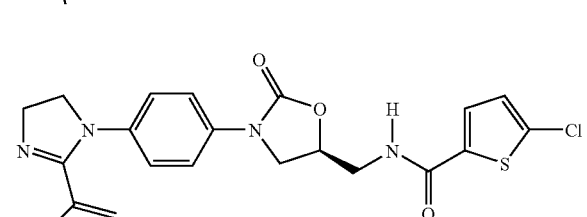
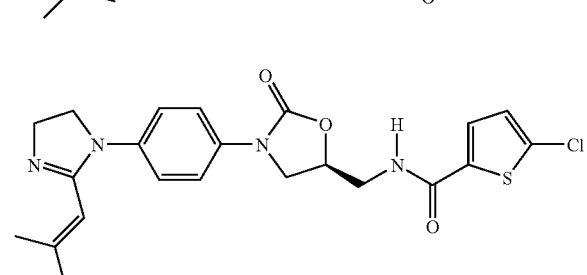
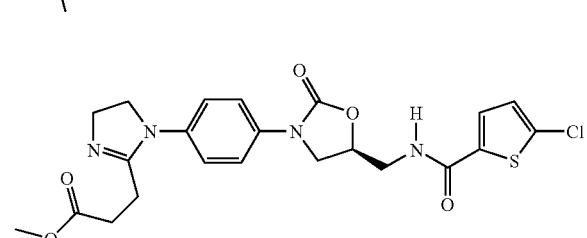
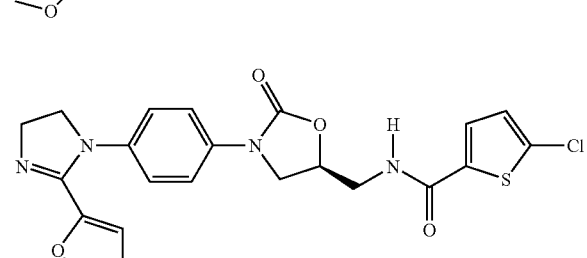
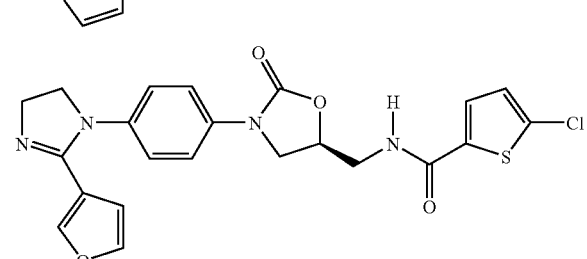
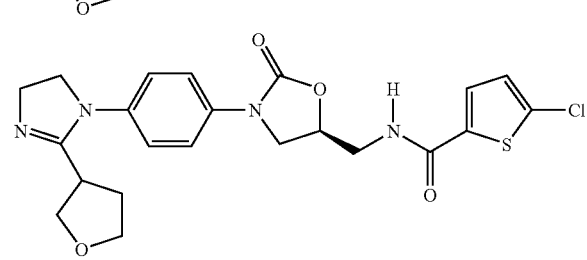

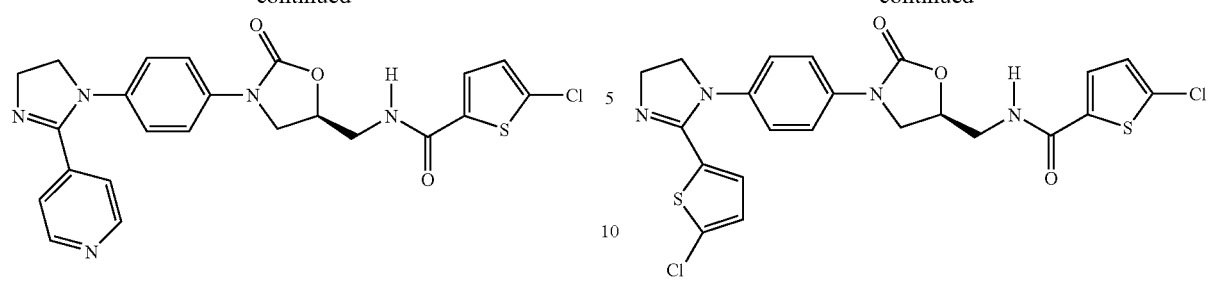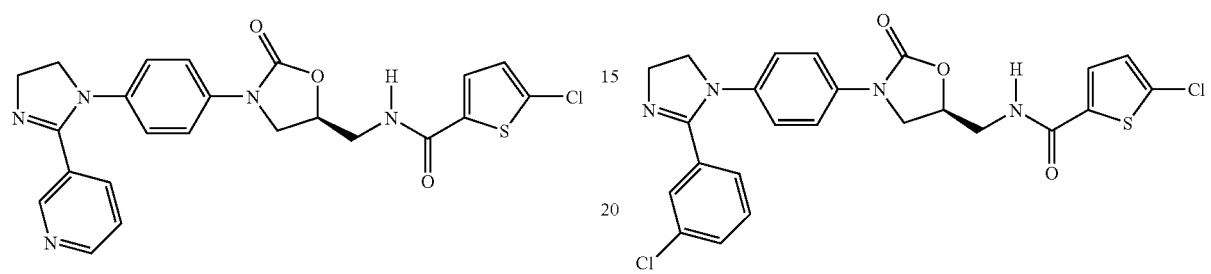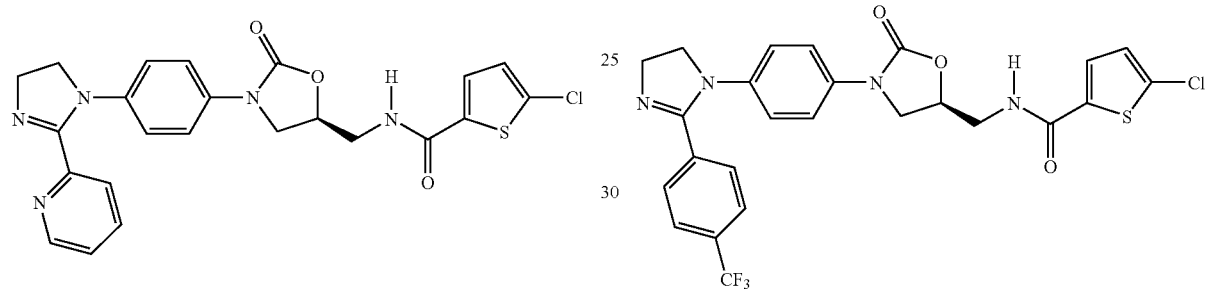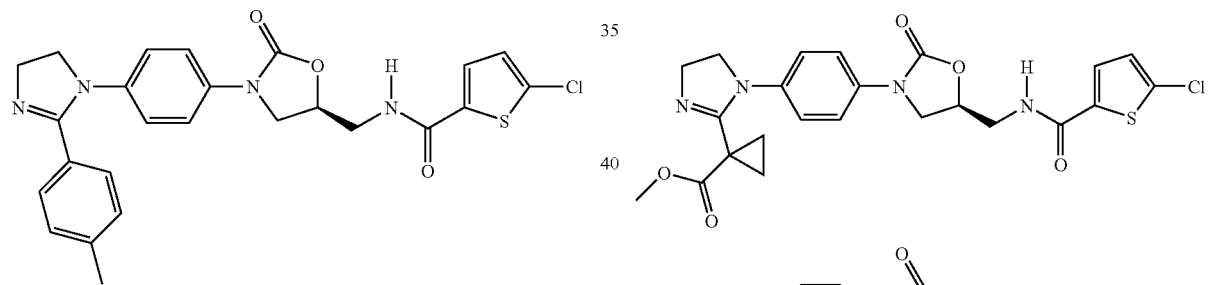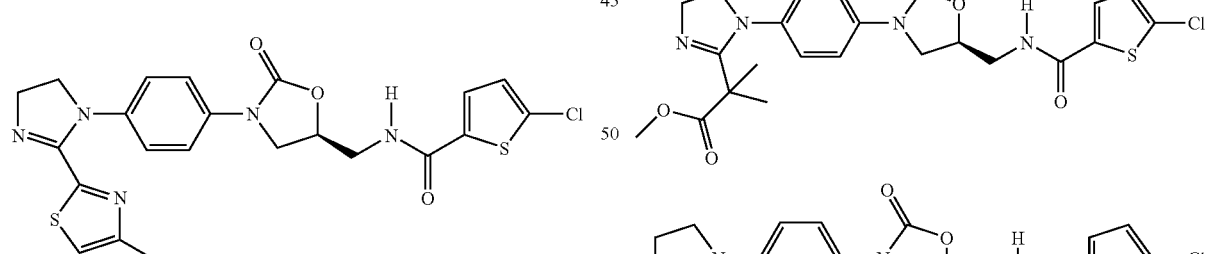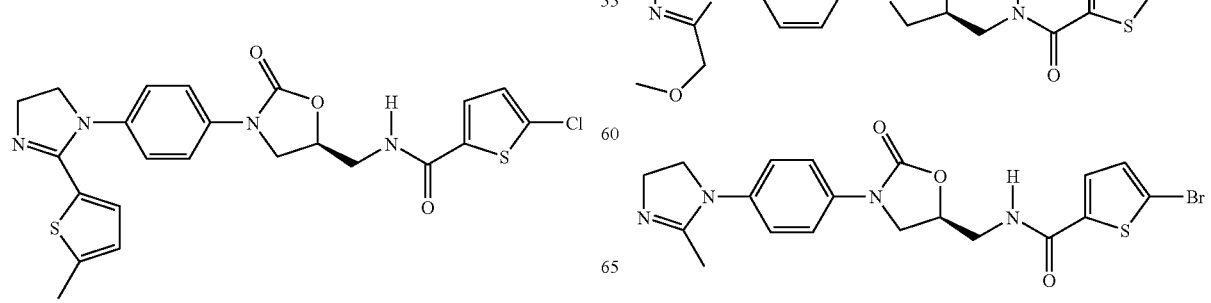

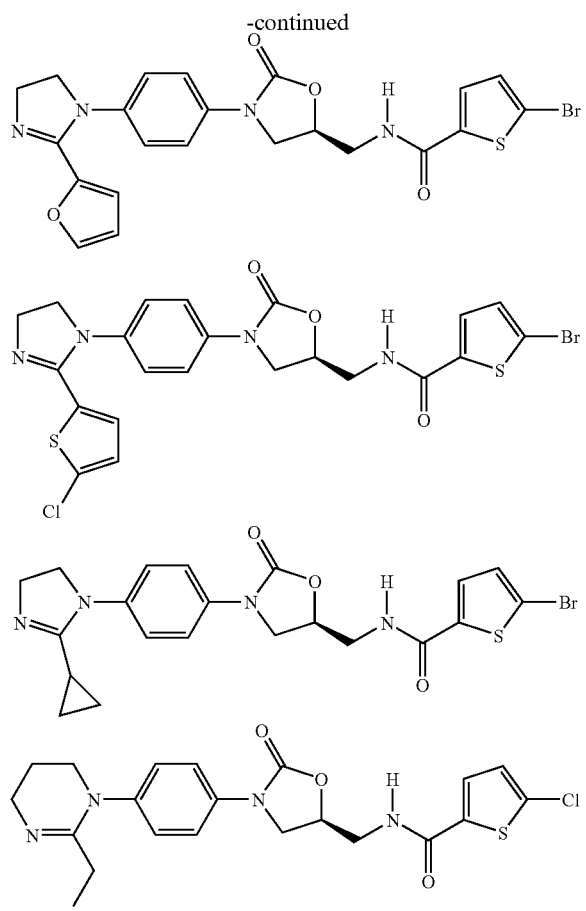

The oxazolidinone derivatives with cyclic amidines, represented by Chemical Formula (1) according to the invention are classified into compounds of type (B) and type (C) depending on the structure of Ring (A). Type (B) compounds can be synthesized according to Reaction Scheme (1), while type (C) compounds can be synthesized according to Reaction Scheme (2). The preparation processes described below does not restrict the processes for preparing the oxazolidinone derivatives with cyclic amidines, represented by Chemical Formula (1) according to the invention, but modification of the processes are obvious to a person having ordinary skill in the art. Definitions of the substituents in the Reaction Schemes are identical to those in Chemical Formula (1), if not specified otherwise.

Type (B) compounds among the compounds of Chemical Formula (1) can be synthesized according to Reaction Scheme (1) below: they were synthesized via Path (A) or Path (B) depending on the type of X in Chemical Formula (1). Most of compounds of type (B) wherein X is hydrogen were synthesized via Path B, starting from Compound (VI). The compounds wherein X is not hydrogen were synthesized via Path (A) or Path (B), depending upon the starting materials commercially available. As is illustrated in Reaction Scheme (1), Compound (I) or (VI) is reacted with (S)-1-(t-butoxycarbonyl)-2,3-oxiranylamine (II) to synthesize Compound (IV) or (VII), which was then reacted with 1,1-carbonyldiimidazole and DMAP to obtain cyclic oxazolidinone compound (V) or (VIII). Compound (V) can be converted to Compound (VIII) by using $Zn(CN)_2/Pd(PPh_3)_4$. The synthesis at this stage can be carried out by using 2-(((S)-oxiran-2-yl)methyl)isoindoline-1,3-dione (III) instead of (X)-1-(t-butoxycarbonyl)-2,3-oxiranylamine (II), to obtain an amine compound protected by phthalimide instead of boc. This process will be explained with regard to Reaction Scheme (2). Though Reaction Scheme (1) indicates the process using (S)-1-(t-butoxycarbonyl)-2,3-oxiranylamine (II), both processes may be employed. When boc protective group of Compound (VIII) was removed by using hydrochloric acid, and the product was condensated with chlorothiophenecarboxylic acid or bromothiophenecarboxylic acid, Compound (X) could be obtained. Compound (X) was then treated with hydrochloride gas, and reacted with various diamine compounds (XI) to obtain Compound (B).

Path A:

[Reaction Scheme 1]

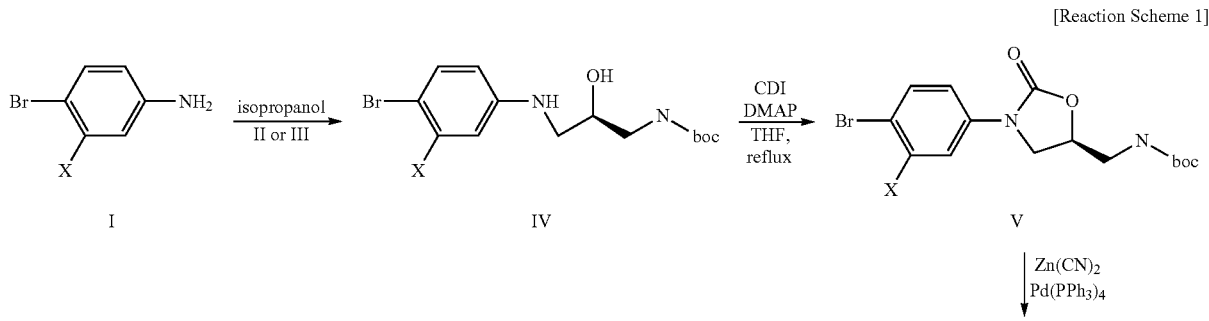

Path B:

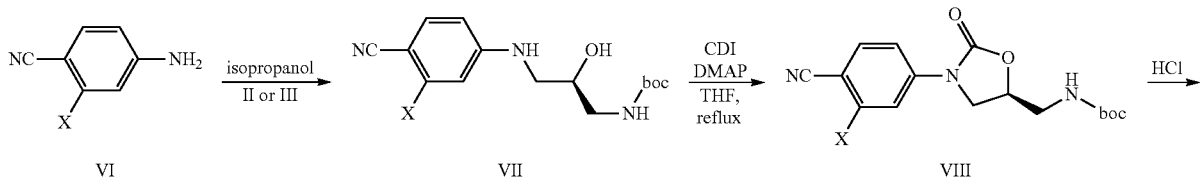

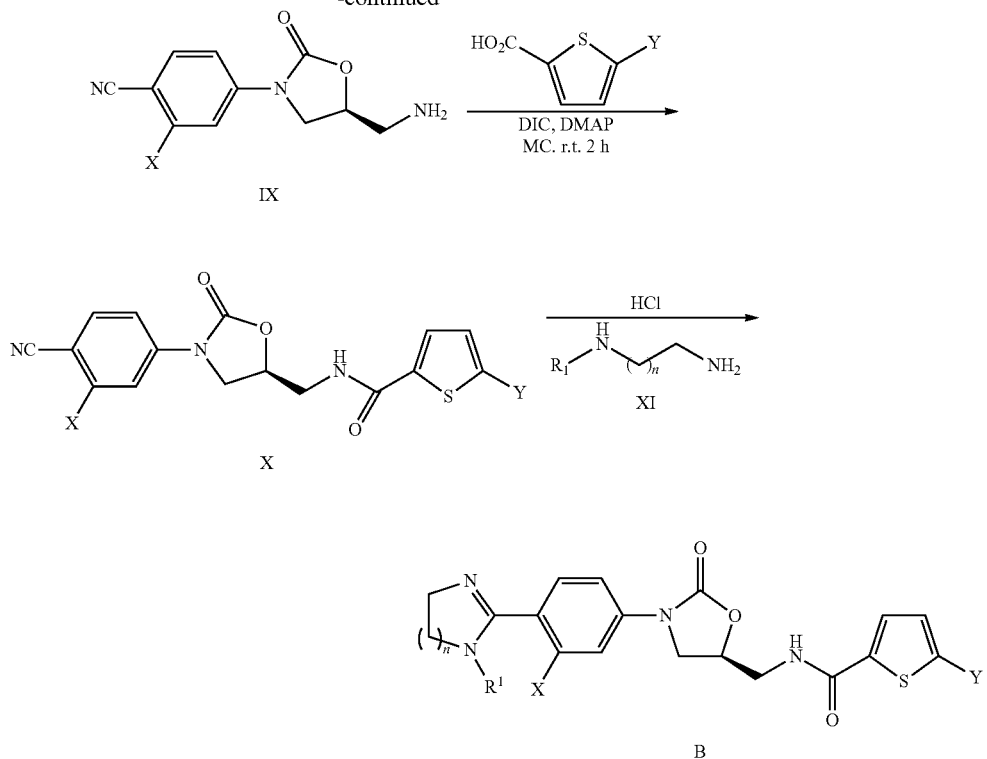

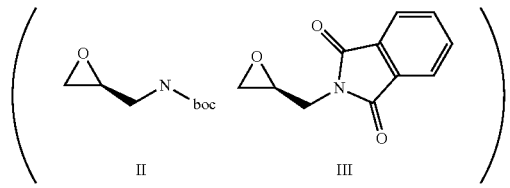

Type (C) compounds of Chemical Formula (1) can be synthesized as shown in Reaction Scheme (2) below. In the same manner as for synthesis of Compounds (B), Compounds (C) can be synthesized via Path (C) or Path (D), depending upon the type of X in Chemical Formula (1). First, Compound (XII) was protected by Boc, and reduced by using hydrogen gas under palladium catalyst. Then the product was reacted with 2-(((S)-oxiran-2-yl)methyl)isoindoline-1,3-dione (III) to obtain Compound (XIV). In this stage, (S)-1-(t-butoxycarbonyl)-2,3-oxiranylamine (II) can be also used as explained for Reaction Scheme (1), but only the process employing 2-(((S)-oxiran-2-yl)methyl)isoindoline-1,3-dione (III) is described herein. Compound (XIV) thus obtained was reacted with 1,1-carbonyldiimidazole and DMAP to form a cyclic oxazolidinone compound (XV). The phthalimide protective group of Compound (XV) was then deprotected by using hydrazine, and the product was condensed with chlorothiophene carboxylic acid or bromothiophene carboxylic acid to obtain Compound (XVI). After treating Compound (XVI) with hydrochloride gas, it is reacted with several aminoaldehyde compounds (XVII) having different methylenic lengths to obtain Compound (XVIII). Compound (XVIII) was again treated with hydrochloric acid and subjected to cyclization to provide Compound (C). In the same manner as in Path (D), the diamine compounds (XX) having different lengths were first reacted with Compound (XIX) to produce Compound (XXI) with diamine moiety incorporated, which was then subjected to the same procedure as Path (D) to produce Compound (XVIII).

[Reaction Scheme 2]

Path C:

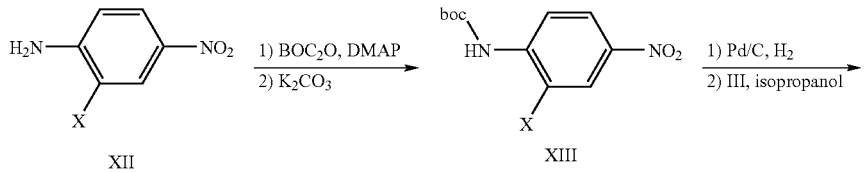

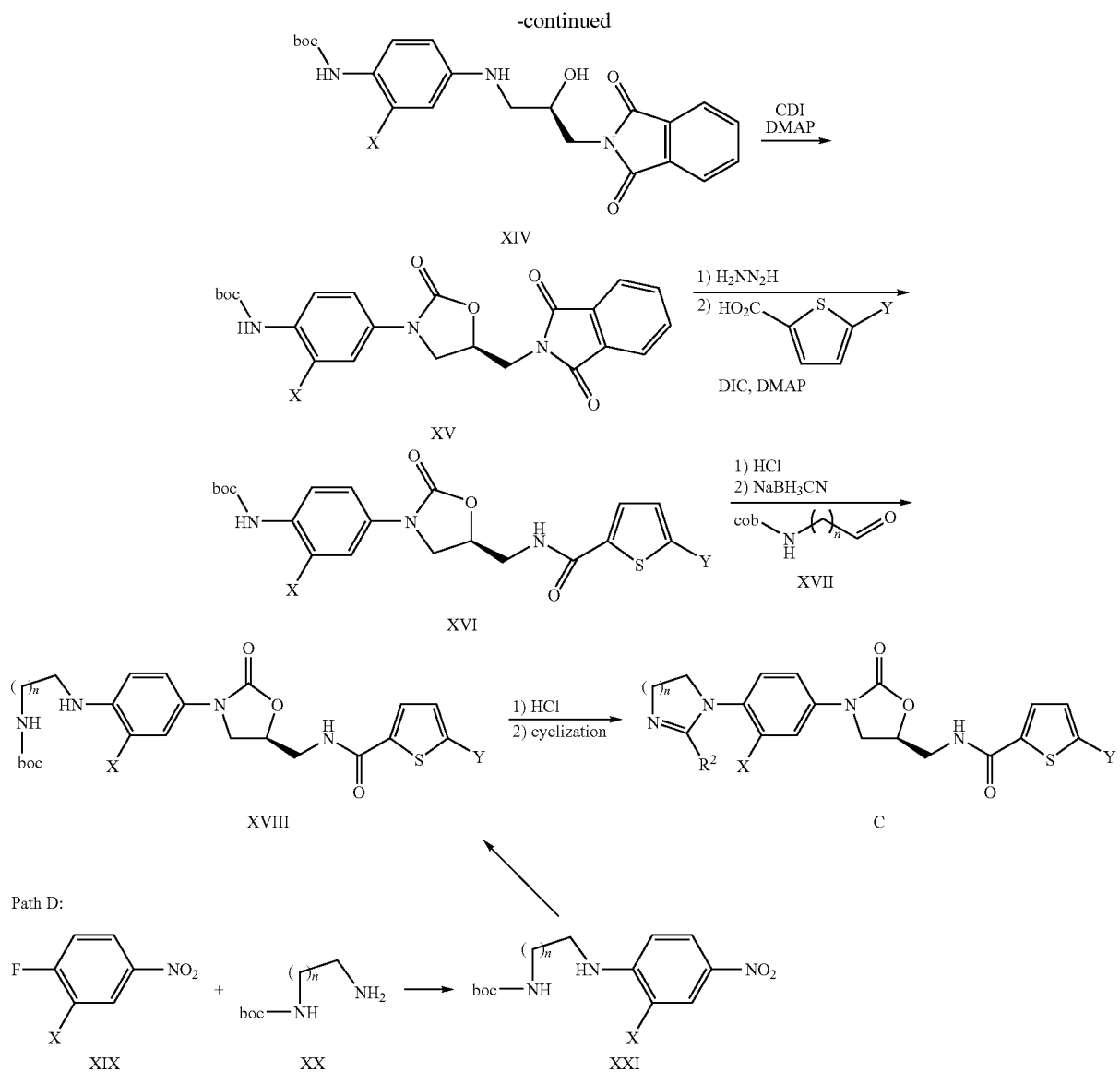

The oxazolidinone derivatives with cyclic amidines represented by Chemical Formula (1) according to the invention can be employed in the field of medicines as a pharmaceutical active ingredient for treating and preventing thrombosis, myocardial infarction, arteriosclerosis, inflammation, cerebral apoplexy, angina pectoris, recurrent stricture after angioplasty, intermittent claudication, phlebothrombosis, pulmonary embolism, arterial thrombosis, myocardial ischemia, unstable angina based on thrombosis or thromboembolism such as attack.

Furthermore, the oxazolidinone derivatives with cyclic amidines represented by Chemical Formula (1) according to the invention can be used for treating or preventing atherosclerotic diseases such as diseases in coronary, cerebral or peripheral arteries. The oxazolidinone derivatives with cyclic amidines can be used in combination with other thrombolytic drugs (such as Alteplase, Tenecteplase) for treatment of myocardial infarction, and they can be also used for preventing thrombolysis, reocclusion after percutaneous transluminal coronary angioplasty (PTCA) or coronary bypass surgery.

In addition, the oxazolidinone derivatives with cyclic amidines can be also used for preventing rethrombokinesis in precise operations, or as an anticoagulant in connection with artificial internal organs or in hemodialysis. The compounds may be employed for washing catheters or medical assist devices used in a patient's body, or as an anticoagulant composition for preserving blood, plasma and other blood products in vitro. The compounds according to the present invention can be used for treating diseases wherein coagulation of blood significantly contributes in the course of the diseases, such as cancers including metastatic cancers, or diseases wherein coagulation makes up secondary cause of lesions, such as inflammatory disorder (including arthritis) and diabetes.

The oxazolidinone derivatives with cyclic amidines represented by Chemical Formula (1) according to the invention can be used as pharmaceutically acceptable salts thereof, including acid addition salts formed with pharmaceutically acceptable free acids. Examples of the free acids include both inorganic and organic acids: inorganic acids such as hydrochloric acid, bromic acid, sulfuric acid and phosphoric acid, and organic acids such as citric acid, acetic acid, lactic acid, maleic acid, umaric acid, gluconic acid, methanesulfonic acid, glyconic acid, succinic acid, 4-toluenesulfonic acid, trifluoroacetic acid, galacturonic acid, embonic acid, glutamic acid and aspartic acid.

BRIEF DESCRIPTION OF DRAWINGS

FIG. 1—Mechansim of blood coagulation

BEST MODE

Now, desirable Examples and Experimental Examples are presented for better understanding of the present invention, which are provided for illustration only but are not intended to limit the scope of the invention by any means.

PREPARATION EXAMPLE 1

Preparation of 5-chloro-thiophene-2-carboxylic acid [(S)-3-(4-cyanophenyl)-2-oxo-oxazolidin-5-ylmethyl]-amide (Compound X-a)

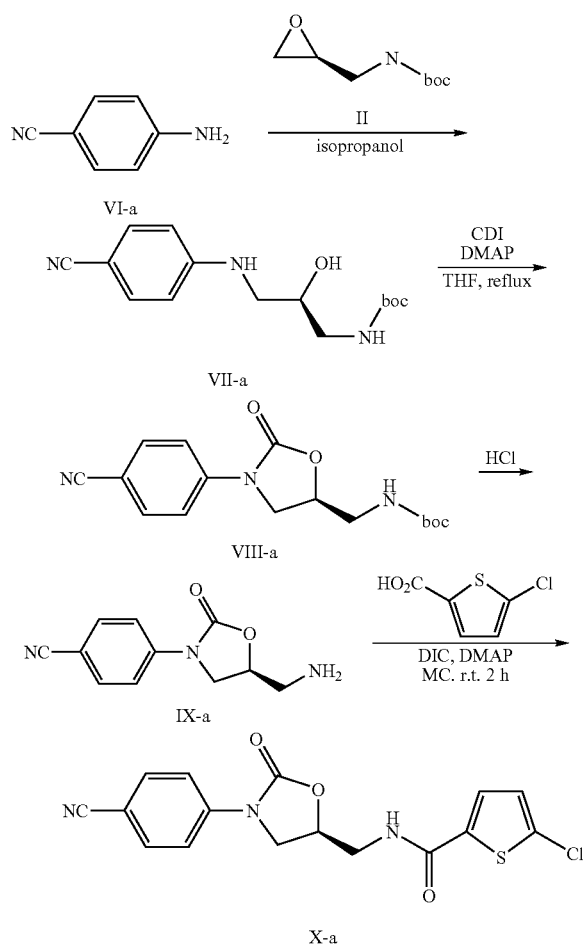

Preparation of [(R)-3-(4-cyanophenylamino)-2-hydroxy-propyl]-carbamic acid tert-butyl ester (Compound VII-a)

To 2-propyl alcohol (20 mL), added were 4-aminobenzonitrile (VI-a) (5 g, 42.30 mmol) and 2-(((S)-oxiran-2-yl)methyl)tert-butyloxycarbonyl (II) (8.79 g, 50.78 mmol), and the mixture was stirred under reflux for 12 hours. The reaction mixture was concentrated under reduced pressure, and the residue was purified via column chromatography to obtain the title compound (VII-a) (7.30 g, 25.1 mmol, 59%) as white solid.

$^1$H NMR (400 MHz, chloroform-$d_1$) δ=7.41 (d, J=8.4 Hz, 4H), 6.59 (d, J=8.4 Hz, 1H), 4.95 (br s, 1H), 4.80 (br s, 1H), 3.97-3.93 (m, 1H), 3.31-3.15 (m, 5H), 1.46 (s, 9H)

Preparation of [(S)-3-(4-cyanophenyl)-2-oxo-oxazolidin-5-ylmethyl]-carbamic acid tert-butyl ester (Compound VIII-a)

Compound (VII-a) (7.30 g, 25.05 mmol) obtained as above, 1,1-carbonyldiimidazole (4.87 g, 30.06 mmol) and dimethylaminopyridine (1.53 g, 12.52 mmol) were sequentially added to tetrahydrofuran (70 mL), and the mixture was stirred under reflux for 12 hours. The reaction mixture was concentrated under reduced pressure, and the residue was dissolved in ethyl acetate (300 mL). The solution was then sequentially washed with aqueous 1N-HCl solution (50 mL) and aqueous sodium bicarbonate solution (50 mL), and dehydrated by using sodium sulfate. Concentration under reduced pressure and washing with diethyl ether (100 mL) gave Compound (VIII-a) (6.60 g, 20.8 mmol, 83%) as white solid.

$^1$H NMR (400 MHz, chloroform-$d_1$) δ=7.67 (s, 4H), 4.95 (br s, 1H), 4.82-4.79 (m, 1H), 4.07 (dd, J=8.8, 8.8 Hz, 1H), 3.94 (dd, J=8.8, 6.8 Hz, 1H), 3.56-3.54 (m, 2H), 1.38 (s, 9H)

Preparation of 5-chloro-thiophene-2-carboxylic acid [(S)-3-(4-cyanophenyl)-2-oxo-oxazolidin-5-ylmethyl]-amide (Compound X-a)

Compound (VIII-a) (6 g, 18.90 mmol) obtained as above was added to ethyl acetate (10 mL), and 4N-HCl dissolved in 1,4-dioxane (60 mL) was then added thereto. After stirring the mixture at ambient temperature for 1 hour, the solid produced was filtered under reduced pressure. Sequential washing of the solid with ethyl acetate (20 mL) and diethyl ether (30 mL) gave the hydrochloride of the amine compound with Boc eliminated (Compound IX-a) (4.60 g, 18.1 mmol, 95.9%) as white solid.

$^1$H NMR (400 MHz, chloroform-$d_1$) δ=8.36 (br s, 3H), 7.90 (d, J=8.8 Hz, 2H), 7.73 (d, J=8.8 Hz, 2H), 5.03-4.96 (m, H), 4.25 (dd, J=9.2, 9.2 Hz, 1H), 3.92 (dd, J=9.2, 6.4 Hz, 1H), 3.28-3.25 (m, 2H)

The amine compound (IX-a) (4.60 g, 18.13 mmol) thus obtained, HOBt (2.75 g, 19.94 mmol), EDC (4.17 g, 21.75 mmol), 5-chlorothiophene-2-carboxylic acid (3.20 g, 19.04 mmol) and triethylamine (5.70 ml, 39.88 mmol) were sequentially added to N,N-dimethylformamide (50 mL), and the mixture was stirred at ambient temperature for 12 hours. The reaction mixture was slowly added to distilled water (800 mL), and the solid produced was filtered under reduced pressure. Washing the solid with diethyl ether to obtain Compound (X-a) (5.70 g, 15.8 mmol, 87%) as white solid.

$^1$H NMR (400 MHz, DMSO-$d_6$) δ=8.93 (t, J=5.2 Hz, 1H), 7.81 (d, J=9.2 Hz, 2H), 7.69 (d, J=9.2 Hz, 2H), 7.63 (d, J=4.0 Hz, 1H), 7.15 (d, J=4.0 Hz, 1H), 4.86-4.81 (m, 1H), 4.17 (dd, J=9.2, 9.2 Hz, 1H), 3.83 (dd, J=9.2, 5.2 Hz, 1H), 3.57 (dd, J=5.2, 5.2 Hz, 2H)

LCMS: 362 (M+W) for $C_{16}H_{12}ClN_3O_3S$

PREPARATION EXAMPLE 2

Preparation of 5-bromo-thiophene-2-carboxylic acid [(S)-3-(4-cyanophenyl)-2-oxo-oxazolidin-5-ylmethyl]-amide (Compound X-b)

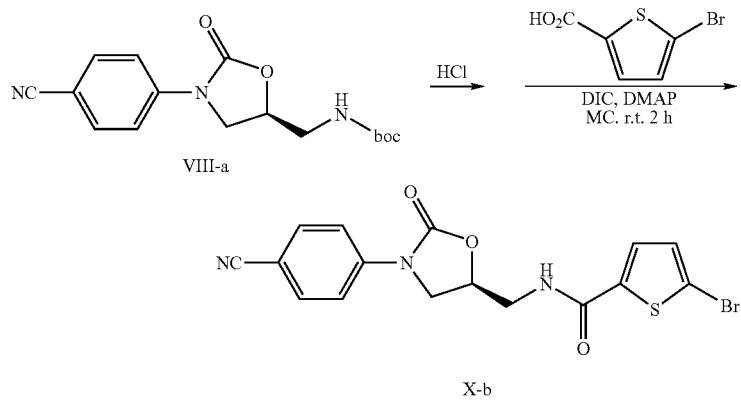

According to the same procedure as Preparation Example 1, but using Compound (VIII-a) (0.50 g, 2.30 mmol) prepared from Preparation Example 1 and 5-bromothiophene-2-carboxylic acid (0.50 g, 2.40 mmol), obtained was the title compound (X-b) (0.78 g, 1.92 mmol, 83.4%) as white solid.

$^1$H NMR (400 MHz, DMSO-$d_6$) δ=8.95 (t, J=5.6 Hz, 1H), 7.86 (d, J=8.8 Hz, 2H), 7.73 (d, J=8.8 Hz, 2H), 7.62 (d, J=4.0 Hz, 1H), 7.29 (d, J=4.0 Hz, 1H), 4.92-4.85 (m, 1H), 4.22 (dd, J=9.2, 9.2 Hz, 1H), 3.88 (dd, J=9.2, 5.6 Hz, 1H), 3.61 (dd, J=5.6, 5.6 Hz, 2H)

LCMS: 407 (M+H$^+$) for $C_{16}H_{12}BrN_3O_3S$

PREPARATION EXAMPLE 3

Preparation of 5-Chloro-thiophene-2-carboxylic acid [(S)-3-(3-fluoro-4-cyano-phenyl)-2-oxo-oxazolidin-5-ylmethyl]-amide (Compound X-c)

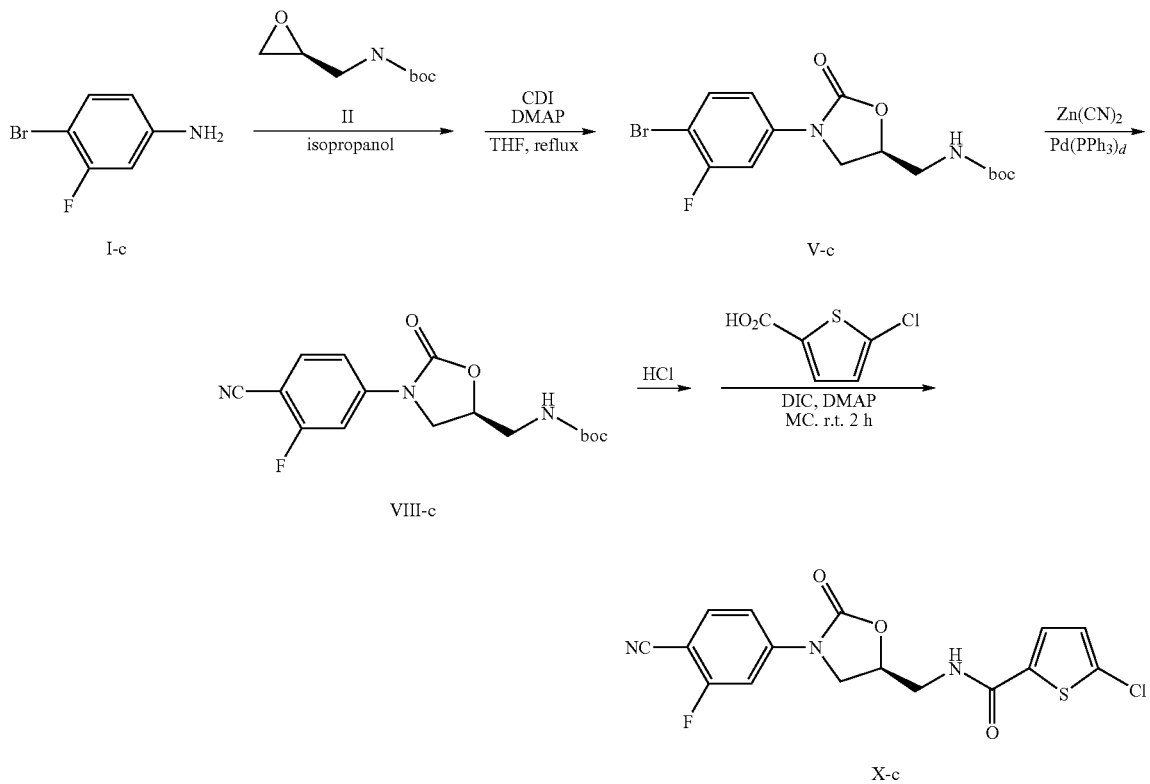

Preparation of [(S)-3-(4-bromo-3-fluorophenyl)-2-oxo-oxazolidin-5-ylmethyl]-carbamic acid tert-butyl ester (Compound V-c)

According to the same procedure as Preparation Example 1, but using 4-bromo-3-fluorobenzenamine (I-c) (0.58 g, 3.03 mmol) and 2-(((S)-oxiran-2-yl)methyl)tert-butyloxycarbonyl (2) (0.58 g, 3.33 mmol), obtained was the title compound (V-c) (1.10 g, 2.83 mmol, 93%) as white solid.

$^1$H NMR (400 MHz, chloroform-$d_1$) δ 7.56 (m, 2H), 7.13 (d, J=10.4 Hz, 1H), 4.96 (br s, 1H), 4.80-4.74 (m, 1H), 4.01 (t, J=9.2 Hz, 1H), 3.85 (t, J=6.4 Hz, 1H), 3.53-4.09 (t, J=6.0 Hz, 2H), 1.40 (s, 9H)

Preparation of [(S)-3-(4-cyano-3-fluorophenyl)-2-oxo-oxazolidin-5-ylmethyl]-carbamic acid tert-butyl ester (Compound VIII-c)

Compound (V-c) (0.50 g, 1.28 mmol) obtained as above was dissolved in dimethyl formamide (5 mL), and zinc cyanide (0.09 g, 0.77 mmol) was added to the solution. After adding tetrakistriphenylphosphine palladium (0) (0.12 g, 0.10 mmol) thereto, the resultant mixture was stirred under reflux for 12 hours. After cooling, the reaction mixture was dissolved in ethyl acetate (50 mL), and the solution was washed three times with distilled water (40 mL). Drying over sodium sulfate and concentration under reduced pressure gave Compound (VIII-c) (0.34 g, 1.01 mmol, 79%) as white solid.

LCMS: 358 (M+Na$^+$) for $C_{20}H_{20}Cl_2N_4O_3S$

Preparation of 5-Chloro-thiophene-2-carboxylic acid [(S)-3-(4-cyano-3-fluoro-phenyl)-2-oxo-oxazolidin-5-ylmethyl]-amide (Compound X-c)

According to the same procedure as Preparation Example 1, but using Compound (VIII-c) (0.34 g, 1.01 mmol) obtained as above and 5-chlorothiophene-2-carboxylic acid (0.20 g, 1.21 mmol), obtained was the title compound (X-c) (0.20 g, 0.53 mmol, 56%) as white solid.

$^1$H NMR (400 MHz, DMSO-$d_6$) δ 8.882 (t, J=5.6 Hz, 1H), 7.74 (dd, J=12.4, 2.0 Hz, 1H), 7.71 (t, J=8.0 Hz, 1H), 7.63 (d, J=4.0 Hz, 1H), 7.43 (dd, J=8.8, 1.6 Hz, 1H), 6.96 (d, J=4.0 Hz, 1H), 4.96-4.89 (m, 1H), 4.20 (t, J=8.8 Hz, 1H), 3.66 (dd, J=9.2, 6.4 Hz, 1H), 3.74-3.63 (m, 2H)

PREPARATION EXAMPLE 4

Preparation of 5-chloro-thiophene-2-carboxylic acid [(S)-3-(3-chloro-4-cyanophenyl)-2-oxo-oxazolidin-5-ylmethyl]-amide (Compound X-d)

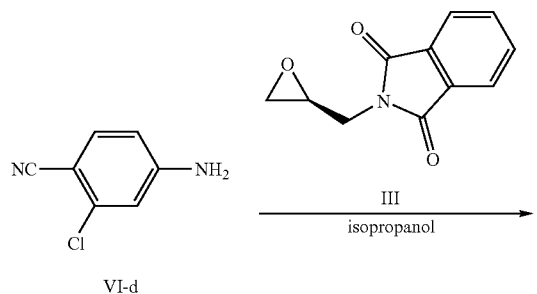

VI-d

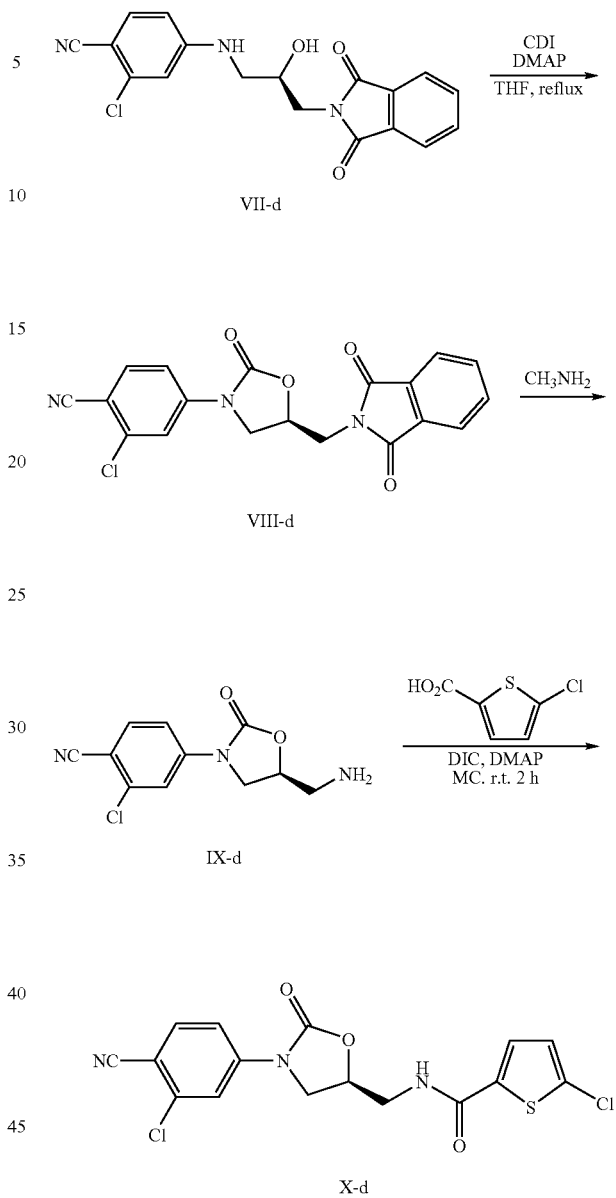

Preparation of 2-((R)-3-(4-cyano-3-chlorophenylamino)-2-hydroxypropyl)isoindoline-1,3-dione) (Compound VII-d)

According to the same procedure as Preparation Example 1, 4-cyano-3-chloroaniline (VI-d) (3.00 g, 19.66 mmol) and 2-(((S)-oxiran-2-yl)methyl)isoindoline-1,3-dione (III) (4.66 g, 20.64 mmol) were stirred under reflux in 2-propylalcohol to obtain the title compound (VII-d) (3.00 g, 8.43 mmol, 43%) as yellow solid.

$^1$H NMR (400 MHz, chloroform-$d_1$) δ 7.69 (d, J=9.2 Hz, 2H), 7.63 (d, J=9.2 Hz, 2H), 7.18 (d, J=8.8 Hz, 1H), 6.56 (d, J=2.0 Hz, 1H), 6.42 (dd, J=8.8, 4.8 Hz, 1H), 5.25 (t, J=5.6 Hz, 1H), 4.15-4.09 (m, 1H), 3.54-3.48 (m, 1H), 3.25-3.10 (m, 3H)

LCMS: 356 (M+H$^+$) for $C_{18}H_{14}ClN_3O_3$

Preparation of 2-((R)-3-(4-cyano-3-chlorophenyl)-2-oxooxazolidin-5-yl)methyl)isoindoline-1,3-dione (Compound VIII-d)

Compound (VII-d) (0.89 g, 2.49 mmol) obtained as above was stirred under reflux with 1,1-carbonyldiimidazole (0.61 g, 3.74 mmol) and dimethylaminopyridine (0.06 g, 0.50 mmol) in tetrahydrofuran (10 mL) to obtain the title compound (VIII-d) (0.30 g, 0.79 mmol, 32%) as yellow solid, according to the same procedure as Preparation Example 1.

$^1$H NMR (400 MHz, DMSO-$d_6$) δ 7.94 (d, J=8.8 Hz, 1H), 7.87-7.81 (m, 4H), 7.59 (d, J=8.8 Hz, 1H), 4.95 (q, J=6.4 Hz, 1H), 4.21 (t, J=9.6 Hz, 1H), 4.00-3.86 (m, 3H)

Preparation of ((S)-5-(aminomethyl)-3-(4-cyano-3-chlorophenyl)oxazolidin-2-one) (Compound IX-d)

Compound (VIII-d) (0.20 g, 0.52 mmol) obtained as above was dissolved in ethyl alcohol (5 mL), and methylamine (0.07 g, 2.30 mmol) was added to the solution. After stirring under reflux for 1 hour, the reaction mixture was cooled and concentrated under reduced pressure to obtain the title compound (IX-d) (0.12 g, 0.52 mmol, 100%) as pale brown oil without further purification.

$^1$H NMR (400 MHz, DMSO-$d_6$) δ 7.99 (d, J=8.8 Hz, 1H), 7.94 (dd, J=8.0, 2.4 Hz, 1H), 7.70 (dd, J=8.0, 2.4 Hz, 1H), 4.70-4.64 (m, 1H), 4.21-4.10 (m, 2H), 3.93 (dd, J=9.2, 6.4 Hz, 1H)

Preparation of 5-Chloro-thiophene-2-carboxylic acid [(S)-3-(3-chloro-4-cyanophenyl)-2-oxo-oxazolidin-5-ylmethyl]-amide (Compound X-d)

According to the same procedure as Preparation Example 1 but using Compound (IX-d) (0.12 g, 0.48 mmol) obtained as above and 5-chlorothiophene-2-carboxylic acid (0.08 g, 0.50 mmol), obtained was the title compound (X-d) (0.07 g, 18 mmol, 37%) as white solid.

$^1$H NMR (400 MHz, DMSO-$d_6$) δ 8.92 (t, J=6.0 Hz, 1H), 7.93 (d, J=8.8 Hz, 1H), 7.87 (d, J=2.0 Hz, 1H), 7.62 (d, J=4.0 Hz, 1H), 7.60 (d, J=2.4 Hz, 1H), 7.14 (d, J=4.0 Hz, 1H), 4.86-4.81 (m, 1H), 4.18 (t, J=9.2 Hz, 1H), 3.84 (dd, J=9.2, 6.0 Hz, 1H), 3.56 (t, J=5.6 Hz, 2H)

PREPARATION EXAMPLE 5

Preparation of Compound (XVIII-a)

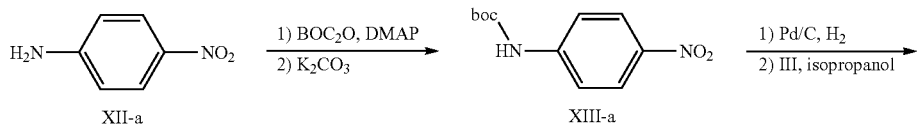

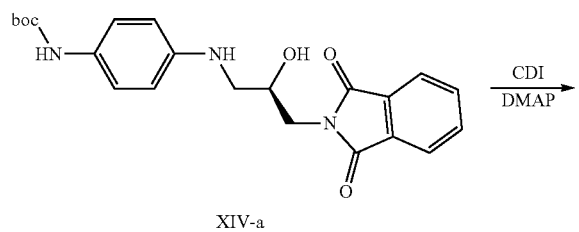

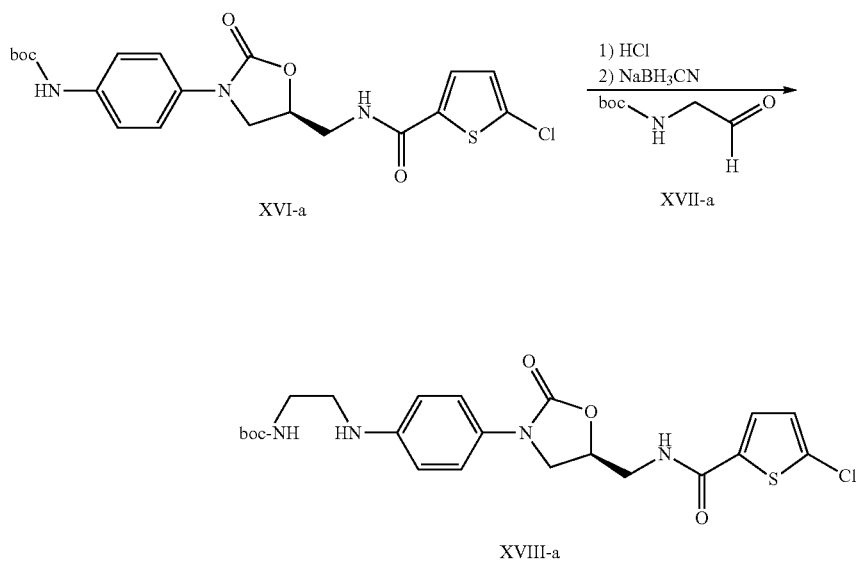

Preparation of Compound (XIII-a)

In acetonitrile (200 mL), dissolved was 4-nitroaniline (XII-a) (20 g, 145 mmol). To the solution, di-t-butyl dicarbonate (63.2 g, 290 mmol) and 4-dimethylaminopyridine (3.54 g, 29 mmol) were added dropwise, and the resultant mixture was stirred under reflux for 16 hours. The reaction mixture was then cooled to ambient temperature, and concentrated under reduced pressure to obtain the compound having two boc groups (49 g, 145 mmol, 100%) as brown solid.

$^1$H NMR (600 MHz, CDCl$_3$) δ=8.25 (d, J=9 Hz, 2H), 7.36 (d, J=9 Hz, 2H), 1.45 (s, 18H)

The compound (49 g, 145 mmol) thus obtained was dissolved in methanol (200 mL), and potassium carbonate (60 g, 434 mmol) was added dropwise thereto. After stirring under reflux for 16 hours, the reaction mixture was cooled to ambient temperature and concentrated under reduced pressure. Purification via column chromatography (n-hexane/ethyl acetate=6/1) gave the title compound (XIII-a) (17.6 g, 73.9 mmol, 51%) as light yellow solid.

$^1$H NMR (600 MHz, CDCl$_3$) δ=8.18 (d, J=9 Hz, 2H), 7.53 (d, J=9 Hz, 2H), 6.93 (br s, 1H), 1.54 (s, 9H)

Preparation of Compound (XIV-a)

Compound (XIII-a) (17.6 g, 73.9 mmol) obtained as above was dissolved in ethyl acetate (200 mL), and palladium/charcoal (10 wt %, 3.9 g) was added thereto. After stirring the mixture under hydrogen balloon for 16 hours, palladium/charcoal was filtered off through a celite filter. Concentration of the filtrate under reduced pressure gave the amine compound (15.4 g, 73.9 mmol, 100%) as light pink solid.

$^1$H NMR (600 MHz, CDCl$_3$) δ=7.12 (br s, 2H), 6.62 (d, J=9 Hz, 2H), 6.31 (br s, 1H), 3.53 (br s, 2H), 1.50 (s, 9H)

The amine compound (13.5 g, 65.1 mmol) thus obtained was dissolved in 2-propanol (170 mL), and (S)-glycidyl phthalimide (III) (14.6 g, 71.9 mmol) was added dropwise thereto. After 12 hours of reaction, (S)-glycidyl phthalimide (2.65 g, 13.0 mmol) was additionally added. After stirring under reflux for hours, the reaction mixture was cooled to ambient temperature, and concentrated under reduced pressure. Recrystallization from n-hexane (500 mL) gave the title compound (XVI-a) (26.8 g, 65.1 mmol, 100%) as yellow solid.

$^1$H NMR (600 MHz, CDCl$_3$) δ=7.89-7.84 (m, 2H), 7.78-7.73 (m, 2H), 7.15 (br, 2H), 6.63 (d, J=8 Hz, 2H), 6.26 (br, 1H), 4.18-4.12 (m, 1H), 4.05 (br, 1H), 3.94-3.86 (m, 2H), 3.25 (dd, J=13, 4.5 Hz, 1H), 3.15 (dd, J=13, 6.6 Hz, 1H), 2.84 (d, J=4.8 Hz, 1H), 1.50 (s, 9H)

Preparation of Compound (XV-a)

Compound (XVI-a) (26.8 g, 65.1 mmol) obtained as above was dissolved in tetrahydrofuran (200 mL), and 1,1-dimethylaminopyridine (1.59 g, 13.0 mmol) were added dropwise thereto. After stirring under reflux for 16 hours, the reaction mixture was cooled to ambient termperature, and concentrated under reduced pressure. Saturated aqueous ammonium chloride solution (200 mL) was added thereto, and the mixture was extracted with ethyl acetate (250 mL×2). The combined organic layer was dried over anhydrous sodium sulfate, and filtered. The filtrate was concentrated under reduced pressure and purified via column chromatography (n-hexane/ethyl acetate/dichloromethane=1/1/1) to obtain the title compound (XV-a) (20.0 g, 45.7 mmol, 70%) as light yellow solid.

$^1$H NMR (600 MHz, CDCl$_3$) δ=7.91-7.87 (m, 2H), 7.79-7.74 (m, 2H), 7.43 (d, J=9 Hz, 2H), 7.36 (d, J=9 Hz, 2H), 6.48 (br s, 1H), 5.00-4.95 (m, 1H), 4.15 (dd, J=14, 7 Hz, 1H), 4.11 (t, J=9 Hz, 1H), 3.97 (dd, J=14, 6 Hz, 1H), 3.89 (dd, J=9, 6 Hz, 1H), 1.52 (s, 9H)

Preparation of Compound (XVI-a)

Compound (XV-a) (15.3 g, 35.0 mmol) obtained as above was dissolved in ethanol (200 mL), and hydrazine hydrate (3.40 mL, 70.0 mmol) was added thereto. After stirring under reflux for hours, the reaction mixture was cooled to ambient temperature. White solid produced was then filtered off, and the filtrate was concentrated under reduced pressure. After adding dichloromethane (100 mL), the solid produced was filtered off, and the filtrate was concentrated under reduced pressure. The procedure was further repeated twice, and the product was dried to obtain the amine compound (10.0 g, 32.5 mmol, 93%) as white solid.

$^1$H NMR (600 MHz, CDCl$_3$) δ=7.45 (d, J=9 Hz, 2H), 7.37 (d, J=9 Hz, 2H), 6.65 (br s, 1H), 4.67-4.63 (m, 1H), 4.03 (t, J=9 Hz, 1H), 3.82 (dd, J=9, 7 Hz, 1H), 3.09 (dd, J=14, 4 Hz, 1H), 2.98 (dd, J=14, 6 Hz, 1H), 1.52 (s, 9H)

The amine compound (3.63 g, 11.8 mmol) thus obtained was dissolved in chloroform (50 mL), and 5-chlorothiophenecarboxylic acid (2.30 g, 14.1 mmol) and 4-dimethylaminopyridine (0.30 g, 13.0 mmol) were added dropwise thereto. The mixture was chilled to 0° C., and N,N'-diisopropylcarbodiimide (2.20 mL, 14.1 mmol) was added dropwise thereto. After stirring at ambient temperature for 2 hours, the reaction mixture was concentrated under reduced pressure. Recrystallization from n-hexane/diethyl ether (1/1, 200 mL) gave the title compound (XVI-a) (5.0 g, 11.1 mmol, 94%) as white solid.

$^1$H NMR (400 MHz, DMSO-d$_6$) δ=9.30 (s, 1H), 8.95 (t, J=6 Hz, 1H), 7.67 (d, J=4 Hz, 1H), 7.45-7.36 (m, 4H), 7.17 (d, J=4 Hz, 1H), 4.82-4.74 (m, 1H), 4.11 (t, J=9 Hz, 1H), 3.77 (dd, J=9, 6 Hz, 1H), 3.57 (t, J=5.6 Hz, 2H), 1.45 (s, 9H)

Preparation of Compound (XVIII-a)

Compound (XVI-a) (16.5 g, 36.5 mmol) obtained as above was dissolved in dichloromethane (150 mL), and hydrochloric acid (150 mL, 4M in 1,4-dioxane) was added thereto. After stirring at ambient temperature for 1 hour, the reaction mixture was concentrated under reduced pressure and dried to obtain the amine compound (14.1 g, 36.3 mmol, 99%) as white solid.

$^1$H NMR (600 MHz, DMSO-d$_6$) δ=9.07 (t, J=6 Hz, 1H), 7.73 (d, J=3.6 Hz, 1H), 7.63 (d, J=9 Hz, 2H), 7.37 (d, J=9 Hz, 2H), 7.20 (d, J=3.6 Hz, 1H), 4.88-4.83 (m, 1H), 4.18 (t, J=9 Hz, 1H), 3.87 (dd, J=9, 6 Hz, 1H), 3.61 (t, J=5.4 Hz, 2H)

To the amine compound (3.0 g, 7.73 mmol) thus obtained, methanol (40 mL) and N,N-dimethylformamide (15 mL) were added dropwise, and N-Boc-2-aminoacetaldehyde (XVII-a) (1.48 g, 9.30 mmol) and sodium cyanoborohydride (486 mg, 7.73 mmol) were then added dropwise thereto. After stirring the mixture at ambient temperature for 16 hours, saturated aqueous ammonium chloride solution (20 mL) was added to the reaction mixture. The solvent was evaporated under reduced pressure, and saturated aqueous ammonium chloride solution (50 mL) was added thereto. After extraction with ethyl acetate (50 mL×2), the combined organic layer was dried over anhydrous sodium sulfate, and filtered. The filtrate was concentrated under reduced pressure and purified via column chromatography (n-hexane/ethyl acetate, 1/2→1/4) to obtain the title compound (XVIII-a) (2.76 g, 5.58 mmol, 72%) as white solid.

$^1$H NMR (400 MHz, CDCl$_3$) δ=7.30 (d, J=4 Hz, 1H), 7.18 (d, J=9 Hz, 2H), 7.00 (t, J=6 Hz, 1H), 6.80 (d, J=4 Hz, 1H), 6.53 (d, J=9 Hz, 2H), 4.84-4.74 (m, 2H), 4.04 (br, 1H), 3.98 (t, J=9 Hz, 1H), 3.81 (ddd, J=14.4, 6, 3 Hz, 1H), 3.74 (dd, J=9, 6 Hz, 1H), 3.66 (dt, J=14.8, 9 Hz, 1H), 3.36-3.26 (m, 2H), 3.18 (t, J=6 Hz, 2H), 1.41 (s, 9H)

EXAMPLE 1

Preparation of 5-chlorothiophene-2-carboxylic acid {(S)-3-[4-(4,5-dihydro-1H-imidazol-2-yl)-phenyl]-2-oxo-oxazolidin-5-ylmethyl}-amide (Compound 100)

Compound X-a (1.30 g, 3.59 mmol) obtained from Preparation Example 1 was added to absolute methyl alcohol (100 mL), and hydrogen chloride gas was bubbled at 0° C. for 30

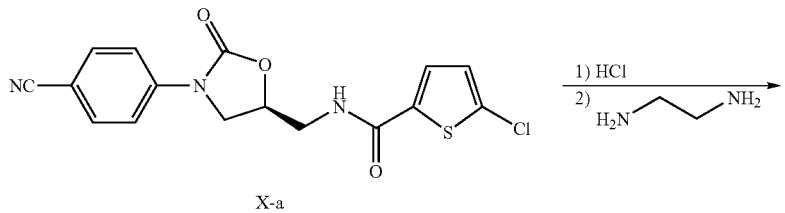

X-a

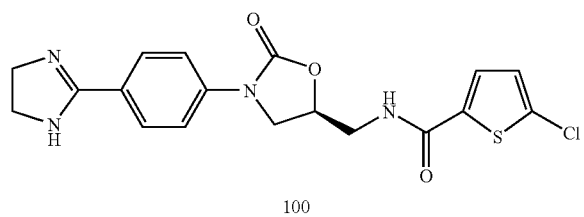

100 minutes. After stirring at ambient temperature for 2 hours, the reaction mixture was concentrated under reduced pressure to remove residual hydrochloric acid. Then, absolute methyl alcohol (60 mL) and ethylenediamine (1 g, 16.58 mmol) was sequentially added thereto. After stirring at ambient temperature for 12 hours, the solid produced was filtered under reduced pressure and washed with diethyl ether (50 mL) to obtain the title compound (100) (1.3 g, 3.22 mmol, 90%) as white solid.

$^1$H NMR (400 MHz, DMSO-d$_6$) δ=10.52 (s, 1H), 9.04 (t, J=6.4 Hz, 1H), 7.99 (d, J=8.8 Hz, 2H), 7.76 (d, J=8.8 Hz, 2H), 7.68 (d, J=4.0 Hz, 1H), 7.15 (d, J=4.0 Hz, 1H), 4.88-4.84 (m, 1H), 4.20 (m, 1H), 3.94 (s, 4H), 3.92-3.88 (m, 1H), 3.58-3.56 (m, 2H)

LCMS: 405 (M+H$^+$) for C$_{18}$H$_{17}$ClN$_4$O$_3$S

EXAMPLE 2

Preparation of 5-chlorothiophene-2-carboxylic acid {(S)-3-[4-(1-methyl-4,5-dihydro-1H-imidazol-2-yl)-phenyl]-2-oxo-oxazolidin-5-ylmethyl}-amide (Compound 101)

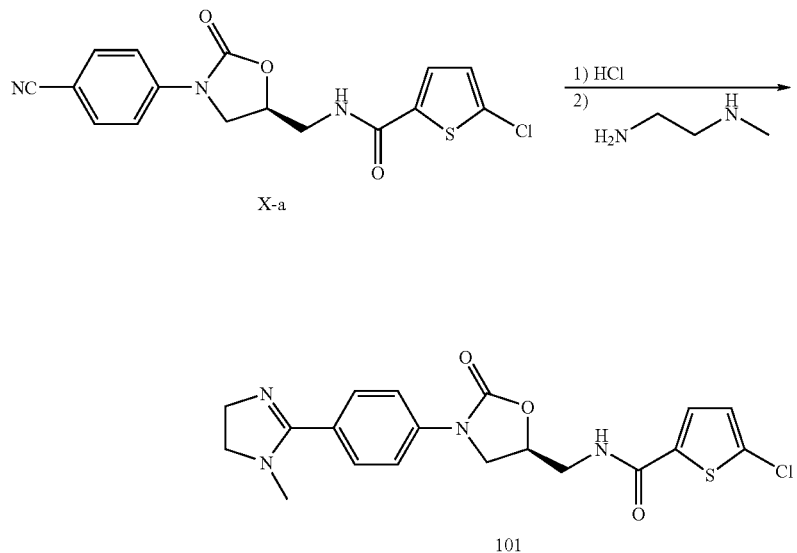

According to the same procedure as Example 1 but using Compound (X-a) (0.2 g, 0.51 mmol) obtained from Preparation Example 1 and N-methylethylenediamine (75 mg, 1.01 mmol), obtained was the title compound (101) (170 mg, 0.40 mmol, 79.6%) as white solid.

$^1$H NMR (400 MHz, chloroform-$d_1$) δ=7.54 (s, 4H), 7.35 (d, J=4.4 Hz, 1H), 6.88 (d, J=4.4 Hz, 1H), 4.80-4.77 (m, 1H), 4.02 (dd, J=9.2, 9.2 Hz, 1H), 3.89-3.79 (m 4H), 3.69-3.62 (m 1H), 3.49-3.43 (m, 2H), 2.79 (s, 3H)

LCMS: 419 (M+H$^+$) for $C_{19}H_{19}ClN_4O_3S$

EXAMPLE 3

Preparation of 5-chlorothiophene-2-carboxylic acid {(S)-3-[4-(1-ethyl-4,5-dihydro-1H-imidazole-2-yl)-phenyl]-2-oxo-oxazolidin-5-ylmethyl}-amide (Compound 102)

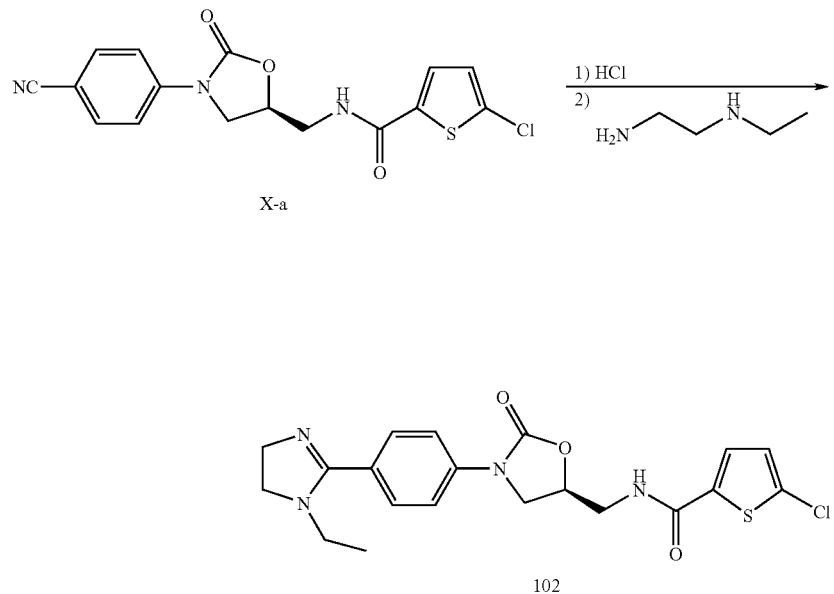

According to the same procedure as Example 1 but using Compound (X-a) (1 g, 2.76 mmol) obtained from Preparation Example 1 and N-ethylethylenediamine (480 mg, 5.52 mmol), obtained was the title compound (102) (320 mg, 0.74 mmol, 27%) as white solid.

$^1$H NMR (400 MHz, chloroform-$d_1$) δ=7.54 (d, J=8.8 Hz, 2H), 7.52 (d, J=8.8 Hz, 2H), 7.34 (d, J=4.0 Hz, 1H), 6.97 (t, J=5.6 Hz, 1H), 6.89 (d, J=4.0 Hz, 1H), 4.83-4.78 (m, 1H), 4.06 (dd, J=8.8, 8.8 Hz, 1H), 3.90-3.83 (m 4H), 3.69-3.62 (m 1H), 3.47 (t, J=9.6 Hz, 2H), 3.09 (q, J=6.4 Hz, 2H), 1.11 (t, J=6.41 Hz, 3H)

LCMS: 432 (M+H$^+$) for $C_{20}H_{21}ClN_4O_3S$

PREPARATION EXAMPLE 4

Preparation of 5-chlorothiophene-2-carboxylic acid {(S)-3-[4-(1-isopropyl-4,5-dihydro-1H-imidazole-2-yl)-phenyl]-2-oxo-oxazolidin-5-ylmethyl}-amide (Compound 103)

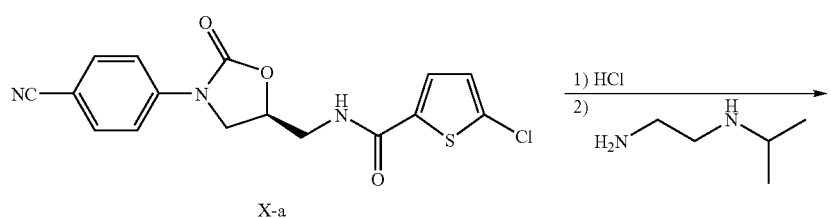

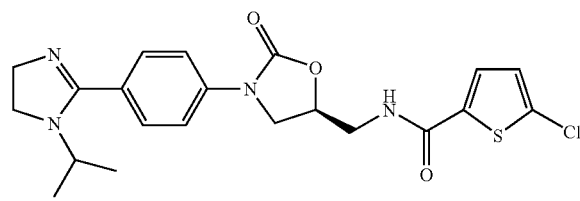

According to the same procedure as Example 1 but using Compound (X-a) (100 mg, 0.27 mmol) obtained from Preparation Example 1 and N-isopropylethylenediamine (56 mg, 0.55 mmol), obtained was the title compound (103) (20 mg, 0.04 mmol, 17%) as white solid.

$^1$H NMR (400 MHz, chloroform-$d_1$) δ=7.94 (d, J=4.4 Hz, 1H), 7.60 (d, J=8.8 Hz, 2H), 7.45 (d, J=8.8 Hz, 2H), 6.84 (d, J=4.4 Hz, 1H), 5.01-4.98 (m, 1H), 4.13-4.04 (m, 1H), 3.77 (t, J=10 Hz, 2H), 3.75-3.71 (m 3H), 3.38 (t, J=10 Hz, 2H), 3.15-3.13 (m, 1H), 1.00 (dd, J=6.4, 0.8 Hz, 6H)

LCMS: 447 (M+H$^+$) for $C_{21}H_{23}ClN_4O_3S$

EXAMPLE 5

Preparation of 5-chlorothiophene-2-carboxylic acid {(S)-3-[4-(1-acetyl-4,5-dihydro-1H-imidazole-2-yl)-phenyl]-2-oxo-oxazolidin-5-ylmethyl}-amide (Compound 104)

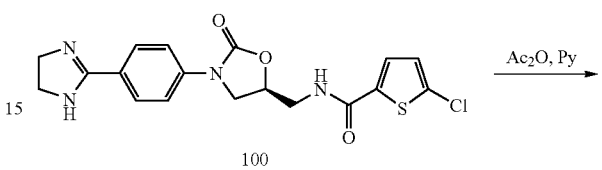

-continued

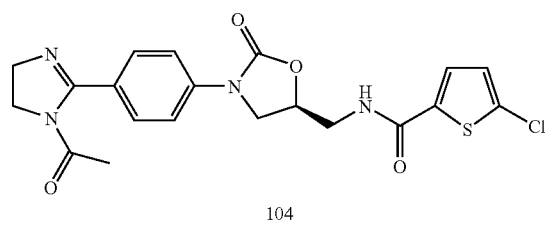

Compound (100) (100 mg, 0.24 mmol) synthesized from Example 1 and acetic anhydride (50 mg, 0.49 mmol) were sequentially added to pyridine (2 mL), and the mixture was stirred at ambient temperature for 8 hours. The reaction mixture was dissolved in dichloromethane (10 mL), and the solution was washed with aqueous sodium bicarbonate solution (5 mL) and dried over sodium sulfate. Concentration under reduced pressure, and preparative chromatography gave the title compound (104) (35 mg, 0.08 mmol, 32%) as white solid.

$^1$H NMR (400 MHz, chloroform-d$_1$) δ=7.65 (s, 2H), 7.59 (d, J=8.8 Hz, 1H), 7.53 (d, J=8.8 Hz, 1H), 7.32 (d, J=4.0 Hz, 1H), 6.91 (d, J=4.0 Hz, 1H), 6.63 (t, J=4.8 Hz, 1H), 4.93-4.88 (m, 1H), 4.19-4.13 (m, 1H), 3.99-3.89 (m 4H), 3.79-3.74 (m, 1H), 3.49-3.43 (m, 1H), 1.93 (s, 3H)

LCMS: 447 (M+H$^+$) for C$_{20}$H$_{19}$ClN$_4$O$_4$S

EXAMPLE 6

Preparation of 5-chlorothiophene-2-carboxylic acid {(S)-3-[4-(1-methanesulfonyl-4,5-dihydro-1H-imidazole-2-yl)-phenyl]-2-oxo-oxazolidin-5-ylmethyl}-amide (Compound 105)

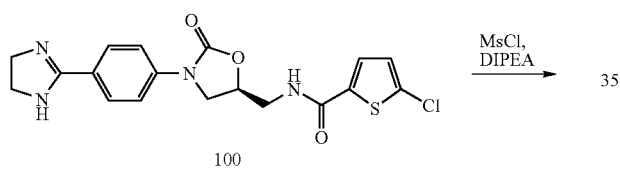

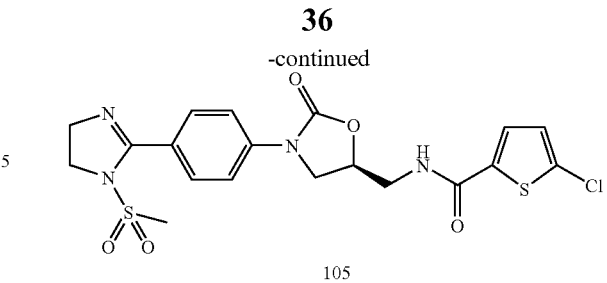

Compound (100) (100 mg, 0.24 mmol) synthesized from Example 1, diisopropylethylamine (65 mg, 0.24 mmol) and methanesulfonyl chloride (42 mg, 0.37 mmol) were sequentially added to dichloromethane (2 mL), and the mixture was stirred at ambient temperature for 6 hours. The reaction mixture was dissolved in dichloromethane (10 mL), and the solution was washed with aqueous sodium bicarbonate solution (5 mL) and dried over sodium sulfate. Concentration under reduced pressure, and preparative chromatography gave the title compound (105) (40 mg, 0.08 mmol, 34%) as white solid.

$^1$H NMR (400 MHz, DMSO-d$_6$) δ=8.94 (t, J=5.2 Hz, 1H), 7.65 (d, J=4.0 Hz, 1H), 7.62 (d, J=8.0 Hz, 2H), 7.53 (d, J=8.0 Hz, 2H), 7.15 (d, J=4.0 Hz, 1H), 4.83-4.78 (m, 1H), 4.16 (dd, J=8.8, 8.8 Hz, 1H), 3.89 (dd, J=8.8, 5.2 Hz, 4H), 3.58-3.55 (m, 2H), 3.02 (s, 3H)

LCMS: 432 (M+H$^+$) for C$_{19}$H$_{19}$ClN$_4$O$_5$S$_2$

EXAMPLE 7

Preparation of 5-chlorothiophene-2-carboxylic acid {(S)-2-oxo-3-[4-(1,4,5,6-tetrahydropyrimidine-2-yl)-phenyl]-oxazolidin-5-ylmethyl}-amide (Compound 106)

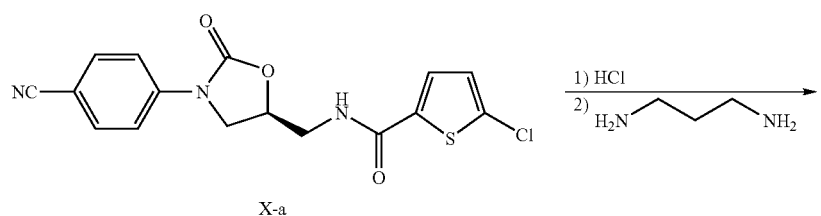

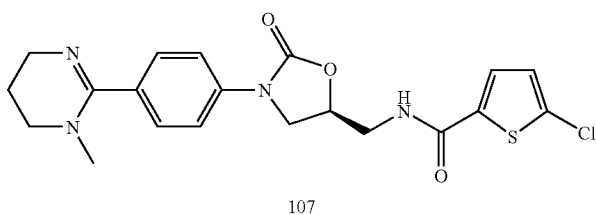

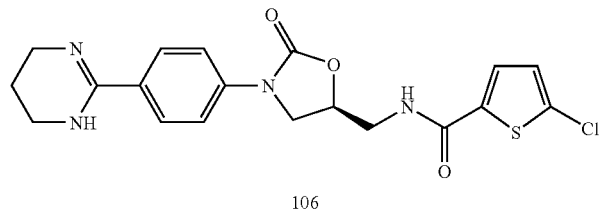

106

According to the same procedure as Example 1 but using Compound (X-a) (1.3 g, 3.59 mmol) obtained from Preparation Example 1 and propylenediamine (0.53 g, 7.19 mmol), obtained was the title compound (106) (1.38 g, 3.30 mmol, 92.0%) as white solid.

$^1$H NMR (400 MHz, DMSO-d$_6$) δ=9.09 (t, J=5.6 Hz, 1H), 7.74 (d, J=9.2 Hz, 2H), 7.70 (d, J=4.0 Hz, 1H), 7.57 (d, J=9.2 Hz, 2H), 7.15 (d, J=4.0 Hz, 1H), 4.85-4.81 (m, 1H), 4.18 (dd, J=8.8, 8.8 Hz, 1H), 3.89 (dd, J=8.8, 5.6 Hz, 4H), 3.59-3.54 (m, 2H), 3.39-3.53 (m, 4H), 1.88-1.84 (m 2H)

LCMS: 419 (M+H$^+$) for C$_{19}$H$_{19}$ClN$_4$O$_3$S

EXAMPLE 8

Preparation of 5-chlorothiophene-2-carboxylic acid {(S)-3-[4-(1-methyl-1,4,5,6-tetrahydropyrimidine-2-yl)-phenyl]-2-oxo-oxazolidin-5-ylmethyl}-amide (Compound 107)

According to the same procedure as Example 1 but using Compound (X-a) (200 mg, 0.51 mmol) obtained from Preparation Example 1 and N-methylpropylenediamine (87 mg, 1.01 mmol), obtained was the title compound (107) (180 mg, 0.41 mmol, 81.53%) as white solid.

$^1$H NMR (400 MHz, chloroform-d$_1$) δ=7.48 (d, J=8.4 Hz, 2H), 7.40 (d, J=4.0 Hz, 1H), 7.37 (d, J=8.4 Hz, 2H), 6.88 (d, J=4.0 Hz, 1H), 4.62-4.58 (m, 1H), 3.89 (dd J=8.8, 8.8 Hz, 1H), 3.81-3.77 (m, 2H) 3.62-3.57 (m 1H), 3.46 (t, J=5.6 Hz, 2H), 3.29 (t, J=5.6 Hz, 2H), 2.75 (s, 3H), 2.03-1.94 (m, 2H)

LCMS: 432 (M+H$^+$) for C$_{20}$H$_{21}$ClN$_4$O$_3$S

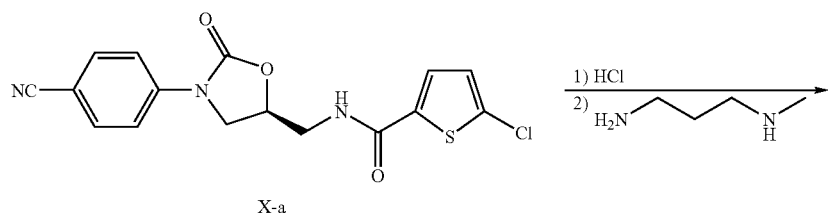

X-a

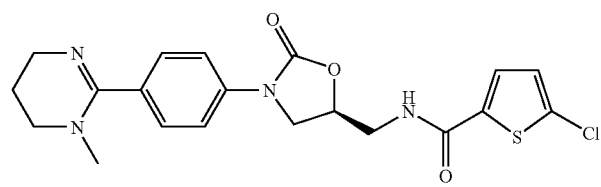

107

EXAMPLE 9

Preparation of 5-bromothiophene-2-carboxylic acid {(S)-3-[4-(1-methyl-4,5-dihydro-1H-imidazol-2-yl)-phenyl]-2-oxo-oxazolidin-5-ylmethyl}-amide (Compound 108)

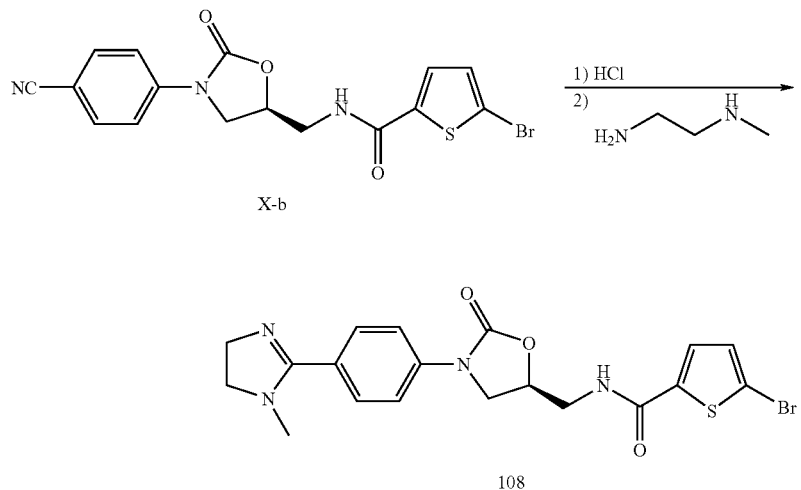

According to the same procedure as Example 1 but using Compound (X-b) (100 mg, 0.24 mmol) obtained from Preparation Example 2 and N-methylethylenediamine (36 mg, 0.49 mmol), obtained was the title compound (108) (29 mg, 0.06 mmol, 24%) as white solid.

$^1$H NMR (400 MHz, chloroform-$d_1$) δ=7.55 (d, J=9.2 Hz, 2H), 7.52 (d, J=4.4 Hz, 1H), 7.49 (d, J=9.2 Hz, 2H), 7.00 (d, J=4.4 Hz, 1H), 4.89-4.81 (m, 1H), 4.09-3.99 (m 2H), 3.94-3.88 (m, 2H), 3.85-3.73 (m 2H), 3.68-3.56 (m, 2H), 2.79 (s, 3H)

LCMS: 464 (M+H$^+$) for $C_{19}H_{19}BrN_4O_3S$

EXAMPLE 10

Preparation of 5-bromothiophene-2-carboxylic acid {(S)-3-[4-(1-ethyl-4,5-dihydro-1H-imidazol-2-yl)-phenyl]-2-oxo-oxazolidin-5-ylmethyl}-amide (Compound 109)

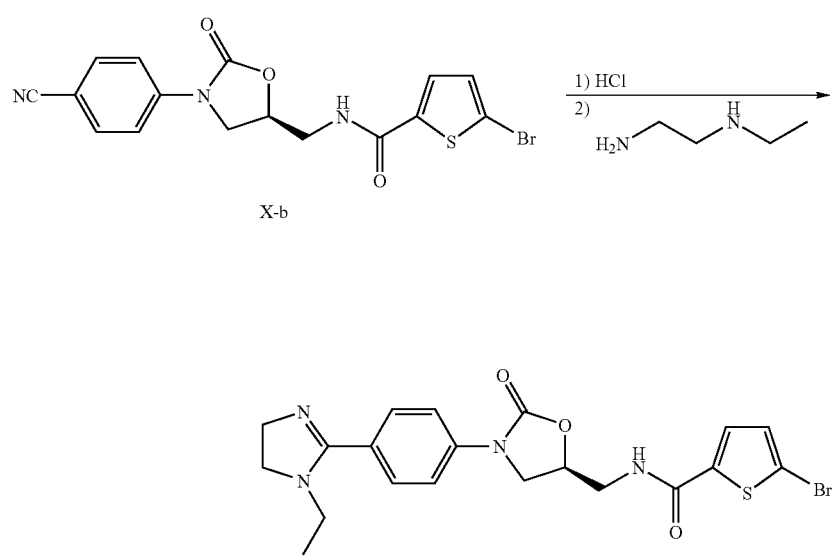

According to the same procedure as Example 1 but using Compound (X-b) (100 mg, 0.24 mmol) obtained from Preparation Example 2 and N-ethylethylenediamine (36 mg, 0.49 mmol), obtained was the title compound (108) (29 mg, 0.06 mmol, 24%) as white solid.

¹H NMR (400 MHz, chloroform-d₁) δ=7.55 (d, J=9.2 Hz, 2H), 7.52 (d, J=4.4 Hz, 1H), 7.49 (d, J=9.2 Hz, 2H), 7.00 (d, J=4.4 Hz, 1H), 4.89-4.81 (m, 1H), 4.09-3.99 (m 2H), 3.94-3.88 (m, 2H), 3.85-3.73 (m 2H), 3.68-3.56 (m, 2H), 2.79 (s, 3H)

LCMS: 464 (M+H⁺) for $C_{19}H_{19}BrN_4O_3S$

EXAMPLE 11

Preparation of 5-chlorothiophene-2-carboxylic acid {(S)-3-[4-(1-ethyl-4,5-dihydro-1H-imidazol-2-yl)-phenyl]-2-oxo-oxazolidin-5-ylmethyl}-amide (Compound 110)

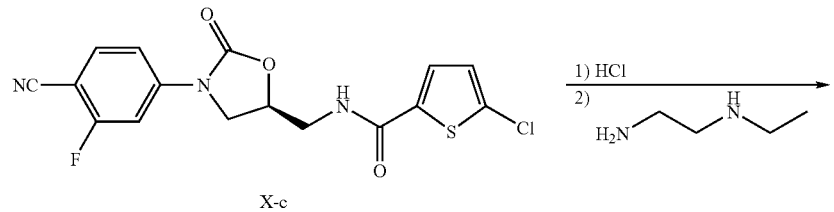

X-c

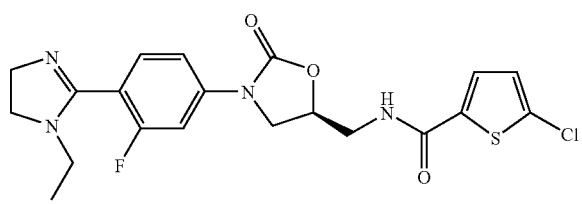

110

According to the same procedure as Example 1 but using Compound (X-c) (0.10 g, 0.27 mmol) obtained from Preparation Example 3 and N-ethylethylenediamine (0.05 g, 0.53 mmol), obtained was the title compound (110) (0.11 g, 0.25 mmol, 91.6%) as white solid.

¹H NMR (400 MHz chloroform-d₁) δ 8.77 (t, J=5.6 Hz, 1H), 7.88 (d, J=4.0 Hz, 1H), 7.76 (dd, J=13.2, 2.0 Hz, 1H), 7.58 (t, J=8.4 Hz, 1H), 7.30 (t, J=6.0 Hz, 1H), 6.82 (d, J=4.0 Hz, 1H), 4.98-4.87 (m, 1H), 4.44-4.40 (m, 1H), 4.14-4.03 (m, 5H), 3.96-3.87 (m, 1H), 3.66-3.61 (m, 1H), 3.35-3.30 (m, 2H), 1.00-0.92 (m, 3H)

LCMS: 451 (M+H⁺) for $C_{20}H_{20}ClN_4O_3S$

EXAMPLE 12

Preparation of 5-chloro-thiophene-2-carboxylic acid {(S)-3-[3-fluoro-4-(1-methyl-1,4,5,6-tetrahydropyrimidin-2-yl)-phenyl]-2-oxo-oxazolidin-5-ylmethyl}-amide (Compound III)

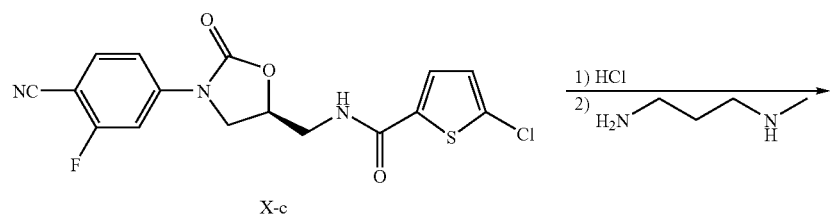

X-c

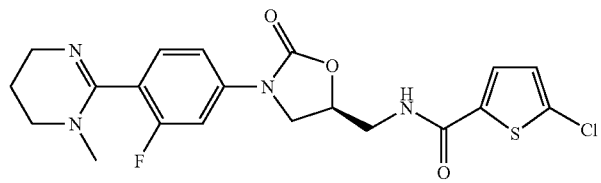

111

According to the same procedure as Example 1 but using Compound (X-c) (0.10 g, 0.27 mmol) obtained from Preparation Example 3 and N-methylpropylenediamine (0.05 g, 0.53 mmol), obtained was the title compound (III) (70 mg, 0.16 mmol, 61.3%) as white solid.

$^1$H NMR (400 MHz, DMSO-$d_6$) δ 9.23 (br s, 1H), 7.79 (d, J=4.0 Hz, 1H), 7.68 (d, J=12.8 Hz, 1H), 7.60 (t, J=8.0 Hz, 1H), 7.52 (br s, 1H), 7.15 (dd, J=4.0, 2.0 Hz, 1H), 4.89-4.85 (m, 1H), 4.17 (t, J=9.2 Hz, 1H), 3.96 (dd J=9.2, 6.0 Hz, 1H), 3.56 (d, J=5.2 Hz, 4H), 3.37-3.30 (m, 4H), 2.90 (s, 3H)

LCMS: 451 (M+H$^+$) for $C_{20}H_{20}ClN_4O_3S$

EXAMPLE 13

Preparation of 5-chlorothiophene-2-carboxylic acid {(S)-3-[3-chloro-4-(1-ethyl-4,5-dihydro-1H-imidazol-2-yl)-phenyl]-2-oxo-oxazolidin-5-ylmethyl}-amide (Compound 112)

According to the same procedure as Example 1 but using Compound (X-d) (0.20 g, 0.50 mmol) obtained from Preparation Example 4 and N-ethylethylenediamine (0.09 g, 1.00 mmol), obtained was the title compound (112) (41.3 mg, 0.09 mmol, 17.7%) as white solid.

$^1$H NMR (400 MHz, DMSO-$d_6$) δ 9.07 (t, J=5.6 Hz, 1H), 7.95 (s, 1H), 7.74 (t, J=4.0 Hz, 3H), 7.20 (d, J=4.0 Hz, 1H), 4.93-4.89 (m, 1H), 4.24 (t, J=9.2 Hz, 1H), 4.13-3.98 (m, 2H), 3.96-3.92 (m, 1H), 3.68-3.58 (m, 2H), 3.25-3.19 (m, 2H), 1.12 (t, J=7.2 Hz, 1H)

LCMS: 467 (M+H$^+$) for $C_{20}H_{20}Cl_2N_4O_3S$ (free form)

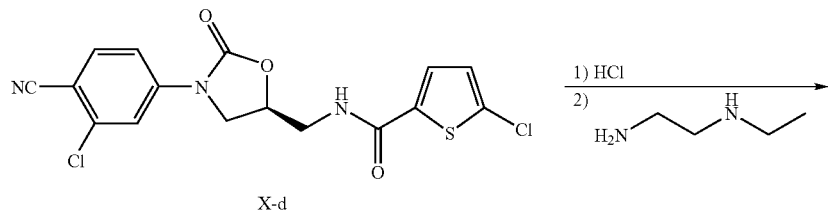

X-d

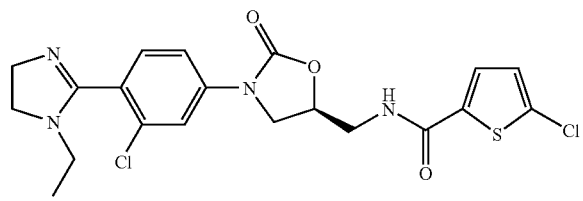

112

EXAMPLE 14

Preparation of 5-chloro-thiophene-2-carboxylic acid {(S)-3-[3-chloro-4-(1-methyl-1,4,5,6-tetrahydropyrimidin-2-yl)-phenyl]-2-oxo-oxazolidin-5-ylmethyl}-amide (Compound 113)

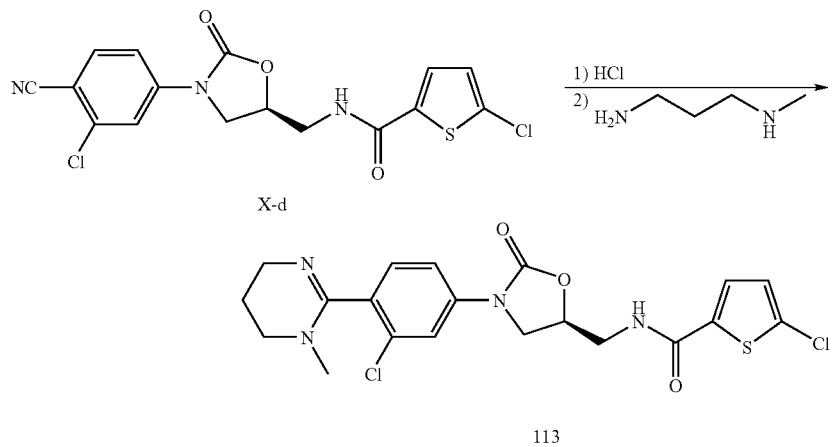

113

According to the same procedure as Example 1 but using Compound (X-d) (0.20 g, 0.50 mmol) obtained from Preparation Example 4 and N-methylpropylenediamine (0.09 g, 1.00 mmol), obtained was the title compound (113) (17.2 mg, 0.04 mmol, 7.4%) as white solid.

$^1$H NMR (400 MHz, DMSO-d$_6$) δ 9.07 (t, J=5.6 Hz, 1H), 7.95 (s, 1H), 7.74 (t, J=4.0 Hz, 3H), 7.20 (d, J=4.0 Hz, 1H), 4.93-4.89 (m, 1H), 4.24 (t, J=9.2 Hz, 1H), 4.13-3.98 (m, 2H), 3.96-3.92 (m, 1H), 3.68-3.58 (m, 2H), 2.80 (s, 3H)

LCMS: 467 (M+H$^+$) for C$_{20}$H$_{20}$Cl$_2$N$_4$O$_3$S (free form)

EXAMPLE 15

Preparation of Compound (114)

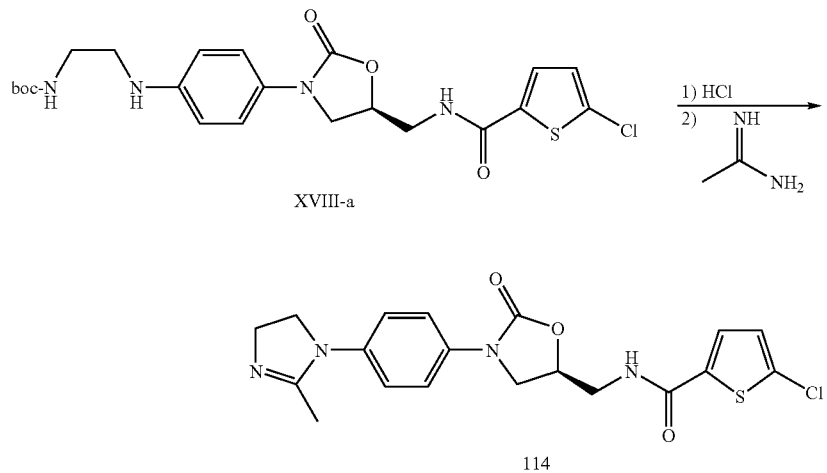

114

Compound (XVIII-a) (168 mg, 0.34 mmol) obtained from Preparation Example 5 was dissolved in dichloromethane (5 mL), and hydrochloric acid (5 mL, 4 M in 1,4-dioxane) was added to the solution. After stirring at ambient temperature for 5 hours, the reaction mixture was concentrated under reduced pressure to obtain the product (159 mg, 0.34 mmol, 100%) as white solid.

$^1$H NMR (400 MHz, DMSO-d$_6$) δ=9.11 (t, J=5.6 Hz, 1H), 8.32 (br, 3H), 7.76 (d, J=3.6 Hz, 1H), 7.37 (d, J=8 Hz, 2H), 7.20 (d, J=3.6 Hz, 1H), 6.88 (d, J=8 Hz, 2H), 4.84-4.76 (m, 1H), 4.10 (t, J=9 Hz, 1H), 3.81 (dd, J=9, 6 Hz, 1H), 3.62-3.53 (m, 2H), 3.35 (t, J=6 Hz, 2H), 3.06-2.94 (m, 2H)

The compound (80 mg, 0.17 mmol) thus obtained was dissolved in 2-propanol (2 mL), and acetamidine hydrochloride (18 mg, 0.19 mmol) and sodium carbonate (27 mg, 0.25 mmol) were added thereto. After stirring the mixture under reflux for 3 hours, the solvent was thoroughly evaporated, and distilled water (10 mL) was added to the residue. The solid produced was filtered, washed with distilled water (10 mL) and diethyl ether (30 mL), and dried to obtain the title compound (114) (38 mg, 0.091 mmol, 53%) as light yellow solid.

$^1$H NMR (400 MHz, DMSO-d$_6$) δ=8.94 (br s, 1H), 7.65 (d, J=4.4 Hz, 1H), 7.44 (d, J=8.8 Hz, 2H), 7.19-7.10 (m, 3H), 4.82-4.73 (m, 1H), 4.12 (t, J=9 Hz, 1H), 3.82-3.75 (m, 1H), 3.73-3.64 (m, 2H), 3.62-3.50 (m, 4H), 1.88 (s, 3H)

LCMS: 419.0 (M+H$^+$) for C$_{19}$H$_{19}$ClN$_4$O$_3$S

EXAMPLE 16

Preparation of Compound (115)

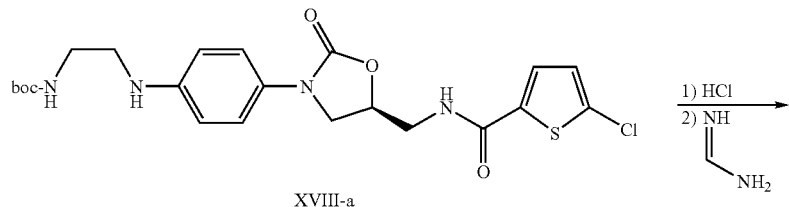

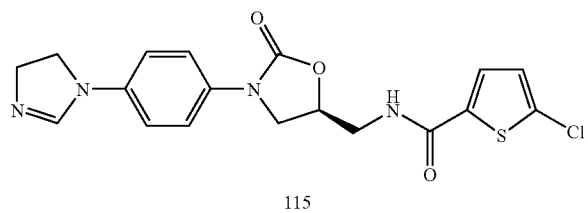

According to a similar procedure to Example 15, but using formamidine acetate instead of acetamidine hydrochloride, synthesized was the title compound (115).

$^1$H NMR (400 MHz, DMSO-$d_6$) δ=8.93 (t, J=5 Hz, 1H), 7.83 (s, 1H), 7.64 (d, J=4 Hz, 1H), 7.38 (d, J=8.8 Hz, 2H), 7.15 (d, J=4 Hz, 1H), 7.40 (d, J=8.8 Hz, 2H), 4.79-4.70 (m, 1H), 4.09 (t, J=9 Hz, 1H), 3.84-3.71 (m, 3H), 3.60-3.50 (m, 4H)

LCMS: 405.0 (M+H$^+$) for $C_{18}H_{17}ClN_4O_3S$

EXAMPLE 17

Preparation of Compound (116)

Compound (XVIII-a) (100 mg, 0.21 mmol) obtained from Preparation Example 5 was treated with hydrochloric acid according to the same procedure as Example 15 to obtain white solid. The solid was dissolved in acetic acid (4 mL), and triethylorthopropionate (2 mL) was added thereto. After stirring the mixture under reflux for 5 hours, the solvent was thoroughly evaporated under reduced pressure. The residue was diluted with saturated aqueous sodium hydrogen carbonate solution (20 mL), and the solution was extracted with dichloromethane (25 mL×2). The combined organic layer was dried over anhydrous sodium sulfate, and filtered. Hydrochloric acid (0.2 mL, 4 N in 1,4-dioxane) was added thereto, and the mixture was concentrated under reduced pressure. White solid produced during this stage was washed with diethyl ether and dried to obtain the title compound (116) (70 mg, 0.15 mmol, 70%).

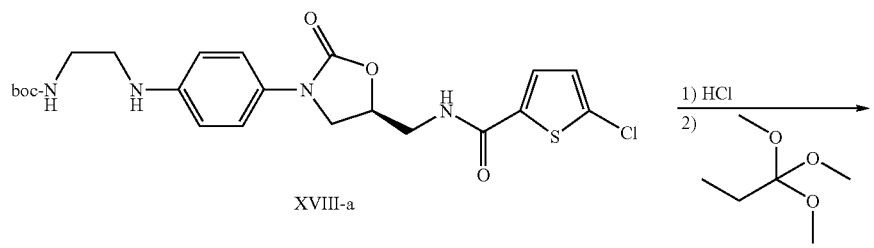

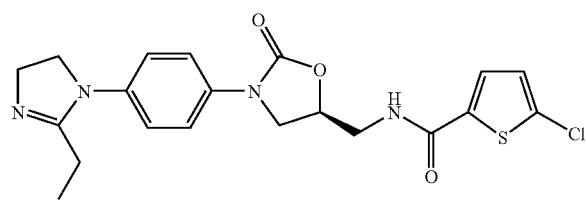

¹H NMR (400 MHz, DMSO-d₆) δ=10.67 (s, 1H), 9.12-9.03 (m, 1H), 7.73 (d, J=4 Hz, 1H), 7.68 (d, J=9 Hz, 2H), 7.52 (d, J=9 Hz, 2H), 7.20 (d, J=4 Hz, 1H), 4.96-4.80 (m, 1H), 4.38-4.18 (m, 2H), 4.02-3.86 (m, 2H), 3.70-3.56 (m, 2H), 3.40-3.30 (m, 2H), 2.50-2.40 (m, 2H), 1.20-1.00 (m, 3H)

LCMS: 433 (M+H⁺) for $C_{20}H_{21}ClN_4O_3S$

EXAMPLE 18

Preparation of Compound (117)

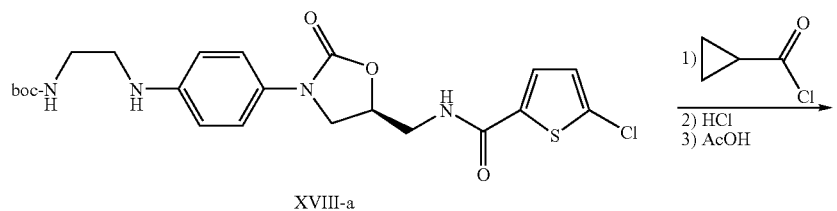

XVIII-a

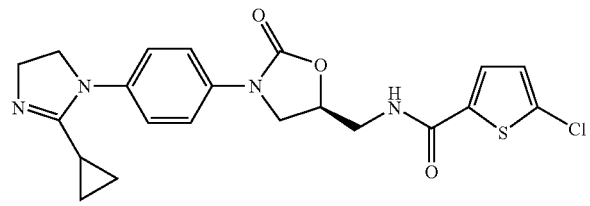

117

Compound (XVIII-a) (200 mg, 0.40 mmol) obtained from Preparation Example 5 was dissolved in dichloromethane (5 mL), and pyridine (48 mg, 0.61 mmol), 4-dimethylaminopyridine (10 mg, 0.08 mmol) and cyclopropane carbonyl chloride (51 mg, 0.48 mmol) were sequentially added dropwise thereto. After stirring the mixture at ambient temperature for 16 hours, saturated aqueous ammonium chloride solution (20 mL) was added to the reaction mixture, which was then extracted with dichloromethane (20 mL×2). The combined organic layer was dried over anhydrous sodium sulfate, and filtered. The filtrate was concentrated under reduced pressure and purified via column chromatography (n-hexane/ethyl acetate=1/2→1/4) to obtain the cyclopropyl amide compound (210 mg, 0.37 mmol, 92%).

¹H NMR (400 MHz, CDCl₃) δ=7.57 (d, J=9 Hz, 2H), 7.37 (dd, J=4, 0.8 Hz, 1H), 7.29 (d, J=9 Hz, 2H), 6.95 (t, J=6 Hz, 1H), 6.89 (dd, J=4, 0.8 Hz, 1H), 5.09 (br s, 1H), 4.94-4.86 (m, 1H), 4.14 (t, J=8.8 Hz, 1H), 3.94-3.85 (m, 2H), 3.85-3.73 (m, 3H), 3.27 (dd, J=11, 6 Hz, 2H), 1.28-1.24 (m, 1H), 1.03-0.97 (m, 2H), 0.66-0.59 (m, 2H)

The compound (210 mg, 0.37 mmol) thus obtained was dissolved in dichloromethane (5 mL), and hydrochloric acid (5 mL, 4 M in 1,4-dioxane solution) was added thereto. After stirring at ambient temperature for 1 hour, the reaction mixture was concentrated under reduced pressure and dried to obtain white solid (185 mg, 0.37 mmol, 99%). The compound (210 mg, 0.45 mmol) thus obtained was dissolved in acetic acid (4 mL) and the solution was stirred under reflux for 16 hours. After cooling to ambient temperature, the reaction mixture was concentrated under reduced pressure, and purified via column chromatography (dichloromethane/methanol (v/v) 20/1→10/1) to obtain the title compound (117) (68 mg, 0.15 mmol, 34%) as white solid.

¹H NMR (600 MHz, DMSO-d₆) δ=9.13 (t, J=6 Hz, 1H), 7.76 (d, J=4 Hz, 1H), 7.68 (d, J=9 Hz, 2H), 7.52 (d, J=9 Hz, 2H), 7.20 (d, J=4 Hz, 1H), 4.90-4.82 (m, 1H), 4.26-4.13 (m, 3H), 3.91 (dd, J=9, 6 Hz, 1H), 3.82 (t, J=10.2 Hz, 2H), 3.66-3.56 (m, 2H), 1.63-1.56 (m, 1H), 1.28-1.20 (m, 2H), 1.17-1.10 (m, 2H)

LCMS: 445 (M+H⁺) for $C_{21}H_{21}ClN_4O_3S$

EXAMPLE 19

Preparation of Compound (118)

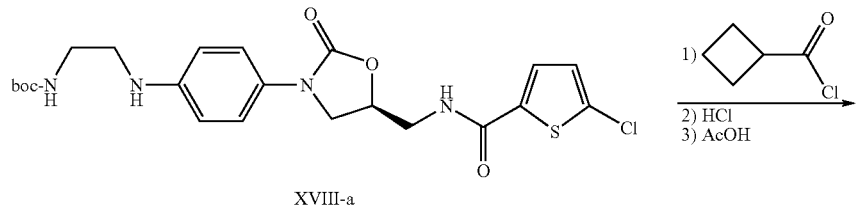

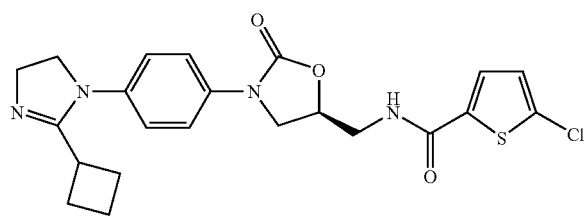

According to a similar procedure to Example 18, synthesized was the title compound (118).

$^1$H NMR (400 MHz, CDCl$_3$) δ=7.55 (d, J=8.8 Hz, 2H), 7.41 (d, J=4 Hz, 1H), 7.22 (t, J=6 Hz, 1H), 7.14 (d, J=8.8 Hz, 2H), 6.89 (d, J=4 Hz, 1H), 4.94-4.85 (m, 1H), 4.15 (t, J=9 Hz, 1H), 3.93 (dd, J=8.8, 6.8 Hz, 1H), 3.90-3.85 (m, 1H), 3.84-3.76 (m, 1H), 3.72 (t, J=6.4 Hz, 2H), 3.00-2.89 (m, 1H), 2.80 (t, J=6.4 Hz, 2H), 2.34-2.19 (m, 2H), 1.79-1.71 (m, 4H)

LCMS: 459 (M+H$^+$) for C$_{22}$H$_{23}$ClN$_4$O$_3$S

EXAMPLE 20

Preparation of Compound (119)

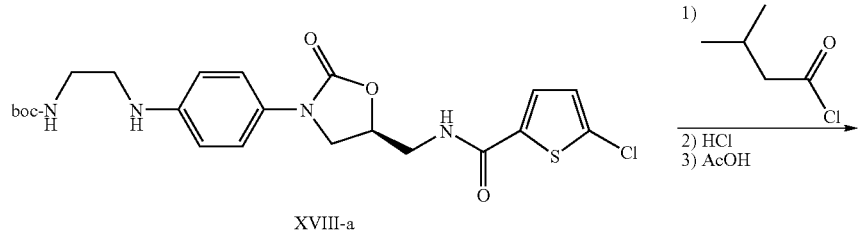

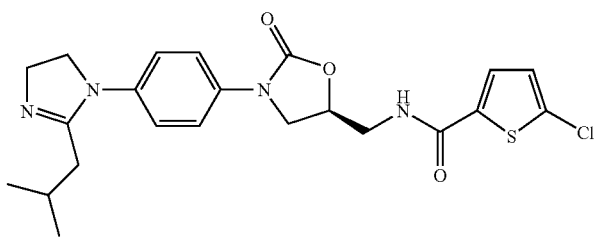

Reaction was carried out according to a similar procedure to Example 18. To the compound obtained after concentration under reduced pressure, hydrochloric acid (0.5 mL, 4 N solution in 1,4-dioxane) was added, and the resultant mixture was concentrated under reduced pressure. White solid produced in this stage was washed with diethyl ether, and dried to obtain hydrochloride of the title compound (119).

$^1$H NMR (400 MHz, DMSO-d$_6$) δ=10.65 (s, 1H), 9.04 (t, J=6 Hz, 1H), 7.72 (d, J=4 Hz, 1H), 7.69 (d, J=8.8 Hz, 2H), 7.53 (d, J=9 Hz, 2H), 7.20 (d, J=4 Hz, 1H), 4.91-4.83 (m, 1H), 4.29 (t, J=10.6 Hz, 2H), 4.21 (t, J=9 Hz, 1H), 3.96 (t, J=10.6 Hz, 2H), 3.89 (dd, J=9, 6 Hz, 1H), 2.36 (d, J=8 Hz, 2H), 1.85-1.75 (m, 1H), 0.82 (d, J=6.8 Hz, 6H)

LCMS: 461 (M+H$^+$) for C$_{22}$H$_{25}$ClN$_4$O$_3$S

EXAMPLE 21

Preparation of Compound (120)

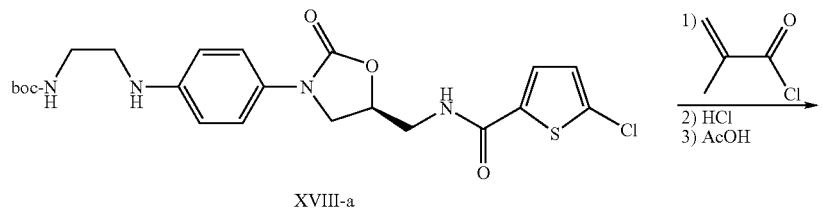

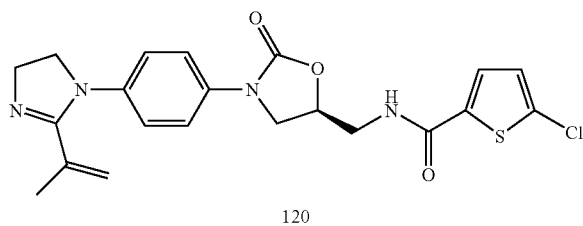

120

The title compound (120) was synthesized according to a similar procedure to Example 18.

$^1$H NMR (600 MHz, CDCl$_3$) δ=7.43 (d, J=9 Hz, 2H), 7.37 (d, J=4.2 Hz, 1H), 7.04 (d, J=9.0 Hz, 2H), 6.90 (d, J=4.2 Hz, 1H), 6.86 (br, 1H), 5.34 (s, 1H), 5.29 (s, 1H), 4.89-4.84 (m, 1H), 4.10 (t, J=9.0 Hz, 1H), 3.98-3.94 (m, 1H), 3.93-3.85 (m, 4H), 3.79-3.74 (m, 2H), 3.65-3.62 (m, 1H), 1.88 (s, 3H)

LCMS: 445 (M+H$^+$) for C$_{21}$H$_{21}$ClN$_4$O$_3$S

EXAMPLE 22

Preparation of Compound (121)

The title compound (121) was synthesized according to a similar procedure to Example 18.

$^1$H NMR (600 MHz, DMSO-d$_6$) δ=8.99 (t, J=6 Hz, 1H), 7.90 (br s, 1H), 7.69 (d, J=4 Hz, 1H), 7.58 (d, J=9 Hz, 2H), 7.26 (d, J=9 Hz, 2H), 7.20 (d, J=4 Hz, 1H), 5.34 (br s, 1H), 4.87-4.81 (m, 1H), 4.20 (t, J=9 Hz, 1H), 3.86 (dd, J=9, 6 Hz, 1H), 3.64 (t, J=6 Hz, 2H), 3.61 (t, J=5.4 Hz, 2H), 3.14 (dd, J=12.6, 6 Hz, 2H), 2.01 (s, 3H), 1.75 (s, 3H), 1.62 (s, 3H)

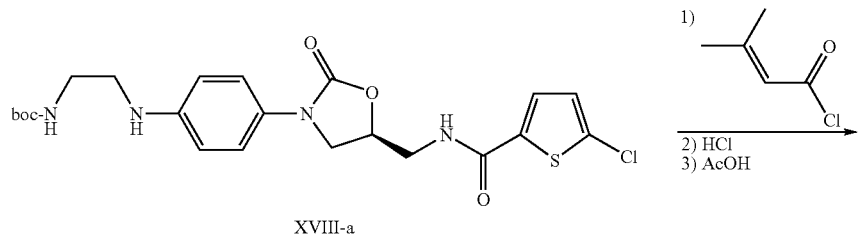

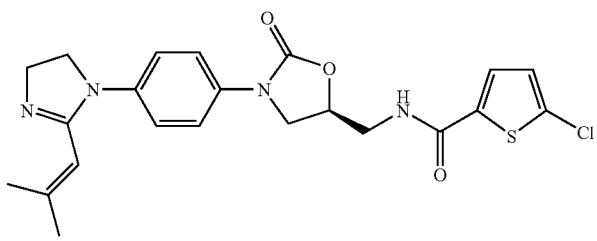

121

EXAMPLE 23
Preparation of Compound (122)
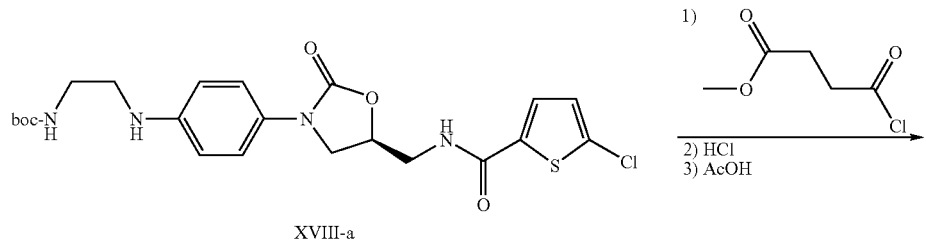
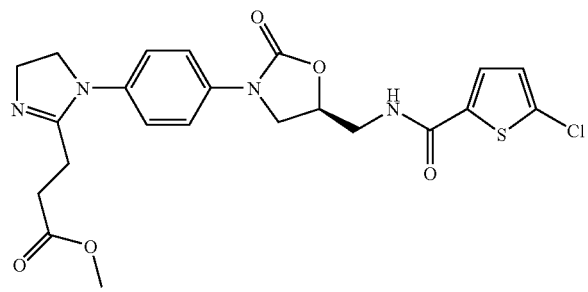
122
The title compound (122) was synthesized according to a similar procedure to Example 18.
$^1$H NMR (600 MHz, acetone-$d_6$) δ=8.79 (t, J=6 Hz, 1H), 7.87 (d, J=4 Hz, 1H), 7.78 (d, J=9 Hz, 2H), 7.53 (d, J=9 Hz, 2H), 7.05 (d, J=4 Hz, 1H), 4.97-4.91 (m, 1H), 4.31 (t, J=11 Hz, 2H), 4.27 (t, J=9 Hz, 1H), 4.19 (dd, J=9, 6 Hz, 1H), 3.96 (t, J=11 Hz, 2H), 3.82-3.77 (m, 1H), 3.75-3.70 (m, 1H), 3.60 (s, 3H), 3.00 (t, J=7 Hz, 2H), 2.72 (t, J=7 Hz, 2H)
LCMS: 491 (M+H$^+$) for $C_{22}H_{23}ClN_4O_5S$
EXAMPLE 24
Preparation of Compound (123)
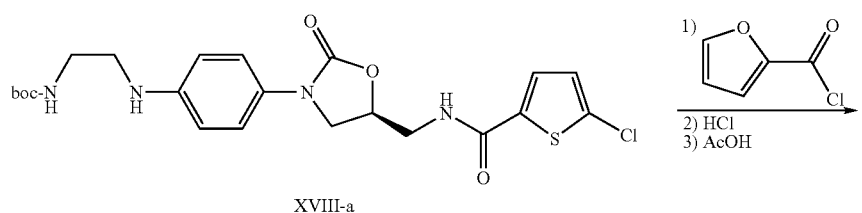
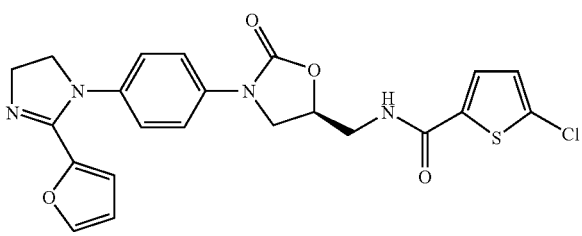
123

The title compound (123) was synthesized according to a similar procedure to Example 18.

$^1$H NMR (400 MHz, DMSO-$d_6$) δ=8.98 (br, 1H), 7.71 (br s, 1H), 7.69 (d, J=4.0 Hz, 1H), 7.47 (d, J=9 Hz, 2H), 7.20 (d, J=4.0 Hz, 1H), 7.00 (d, J=9 Hz, 2H), 6.52 (br s, 1H), 6.45 (br, 1H), 4.86-4.76 (m, 1H), 4.15 (t, J=9 Hz, 1H), 3.96-3.79 (m, 5H), 3.64-3.56 (m, 2H)

LCMS: 471 (M+H$^+$) for $C_{22}H_{19}ClN_4O_4S$

EXAMPLE 25

Preparation of Compound (124)

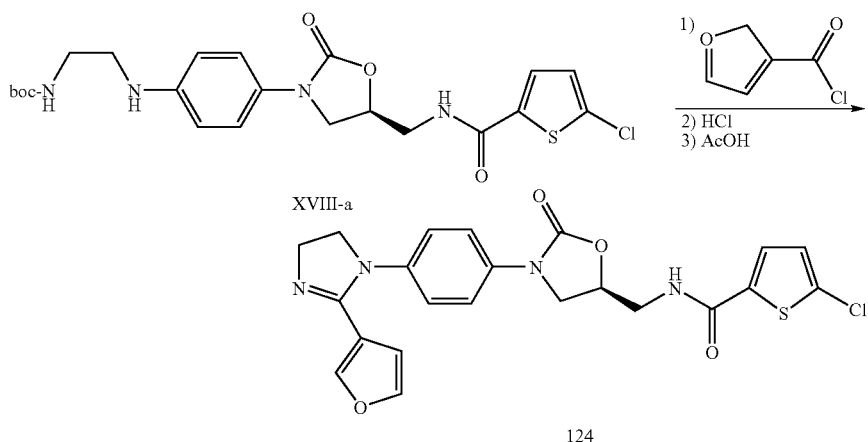

The title compound (124) was synthesized according to a similar procedure to Example 18.

$^1$H NMR (600 MHz, DMSO-$d_6$) δ=8.97 (d, J=6 Hz, 1H), 7.72-7.66 (m, 2H), 7.55-7.40 (m, 3H), 7.22-7.16 (m, 3H), 6.36 (s, 1H), 4.86-4.80 (m, 1H), 4.17 (t, J=9.0 Hz, 1H), 3.96-3.89 (m, 4H), 3.85-3.82 (m, 1H), 3.63-3.57 (m, 2H)

LCMS: 471 (M+H$^+$) for $C_{22}H_{19}ClN_4O_4S$

EXAMPLE 26

Preparation of Compound (125)

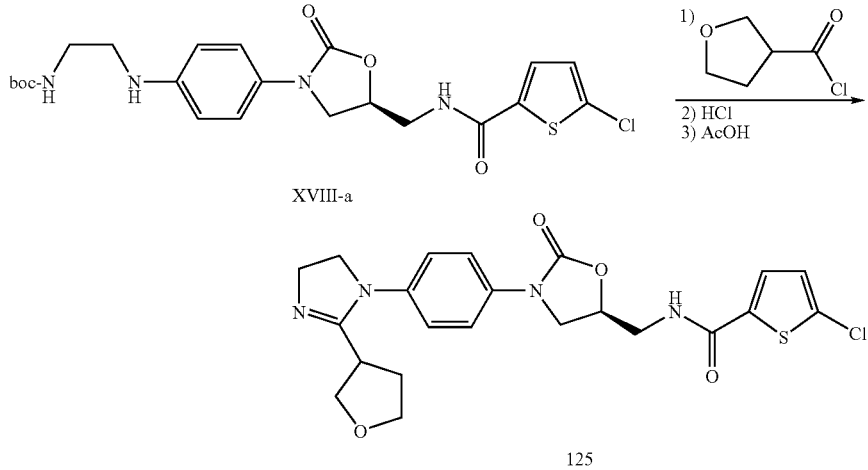

The title compound (125) was synthesized according to a similar procedure to Example 18.

$^1$H NMR (400 MHz, CDCl$_3$) δ=7.53 (d, J=9 Hz, 2H), 7.30 (d, J=4 Hz, 1H), 7.14 (d, J=9 Hz, 2H), 6.92 (d, J=4 Hz, 1H), 6.41 (t, J=6 Hz, 1H), 4.92-4.84 (m, 1H), 4.13 (td, J=8.8, 2.8 Hz, 1H), 3.96-3.73 (m, 11H), 3.03-2.94 (m, 1H), 2.25-2.15 (m, 1H), 2.04-1.96 (m, 1H)

LCMS: 475 (M+H$^+$) for C$_{22}$H$_{23}$ClN$_4$O$_4$S

EXAMPLE 27

Preparation of Compound (126)

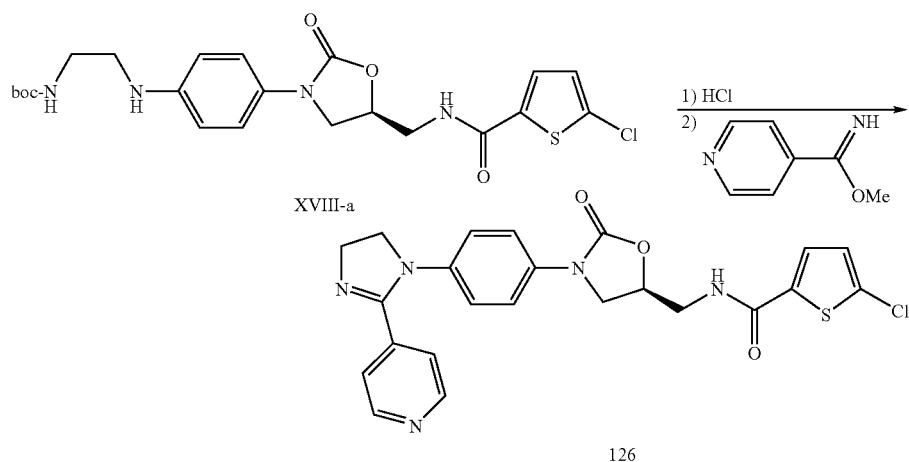

Compound (XVIII-a) obtained from Preparation Example 5 was treated with hydrochloric acid as was in Example 15 to obtain a compound (120 mg, 0.26 mmol). The compound was then suspended in chloroform (5 mL), and 4-pyridinecarboxylmidamide (reference: J. Med. Chem. 1990, 33, 1230) (120 mg, 0.88 mmol) was added thereto. The resultant mixture was stirred under reflux for 12 hours, and then cooled to ambient temperature. Saturated aqueous sodium hydrogen carbonate solution (10 mL) was added, and the mixture was extracted with dichloromethane (20 mL×3). The combined organic layer was dried over anhydrous sodium sulfate, and filtered. Purification via column chromatography (dichloromethane/methanol (v/v) 20/1→10/1) gave the title compound (126) (30 mg, 0.062 mmol, 24%) as light yellow solid.

$^1$H NMR (600 MHz, CDCl$_3$) δ=8.54 (d, J=6.0 Hz, 2H), 7.64 (t, J=6.0 Hz, 1H), 7.37-7.29 (m, 5H), 6.81-6.78 (m, 3H), 4.86-4.80 (m, 1H), 4.11-4.08 (m, 2H), 4.06-4.01 (m, 3H), 3.78-3.83 (m, 2H), 3.61-3.71 (m, 1H)

LCMS: 482 (M+H$^+$) for C$_{23}$H$_{20}$ClN$_5$O$_3$S

EXAMPLE 28

Preparation of Compound (127)

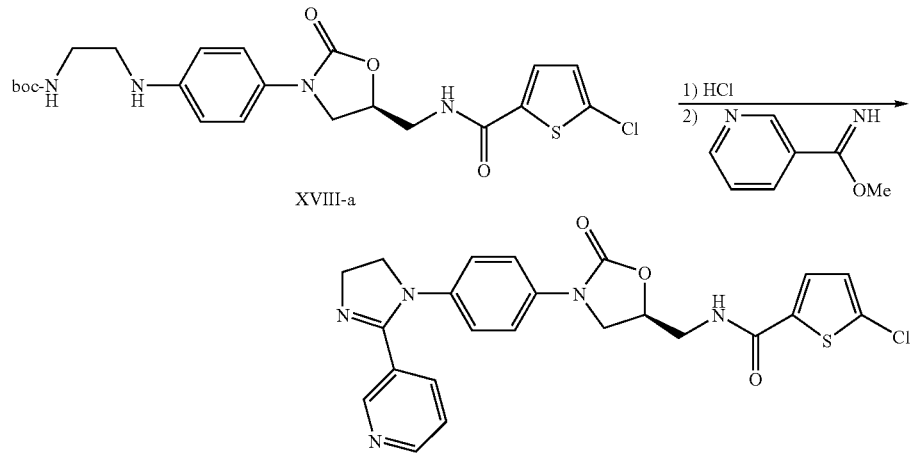

The title compound (127) was synthesized according to a similar procedure to Example 27.

$^1$H NMR (600 MHz, DMSO-d$_6$) δ=8.96 (t, J=6 Hz, 1H), 8.59-8.55 (m, 2H), 7.77-7.73 (m, 1H), 7.67 (d, J=4.2 Hz, 1H), 7.41-7.35 (m, 3H), 7.19 (d, J=4.2 Hz, 1H), 7.13-7.08 (m, 2H), 4.82-4.75 (m, 1H), 4.10 (t, J=9 Hz, 1H), 4.00-3.91 (m, 4H), 3.79-3.74 (m, 1H), 3.59-3.54 (m, 2H)

LCMS: 482 (M+H$^+$) for C$_{23}$H$_{20}$ClN$_5$O$_3$S

EXAMPLE 29

Preparation of Compound (128)

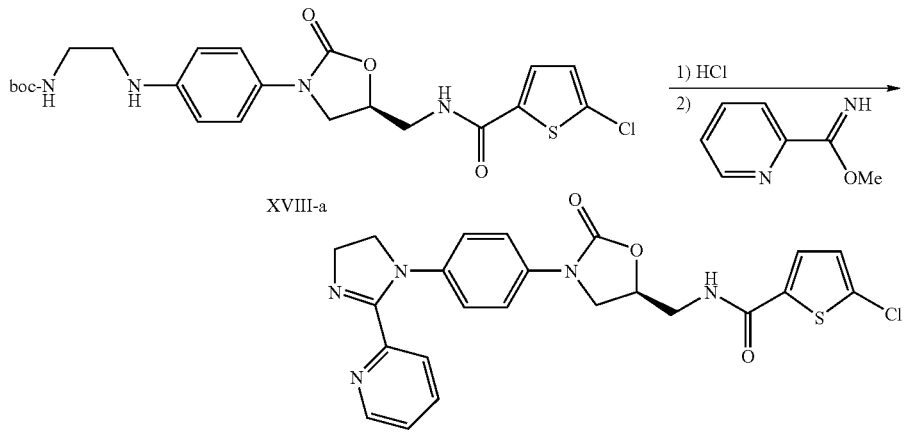

The title compound (128) was synthesized according to a similar procedure to Example 27.

$^1$H NMR (600 MHz, CDCl$_3$) δ=8.47 (d, J=5.4 Hz, 1H), 7.80 (d, J=6.0 Hz, 1H), 7.70 (t, J=7.2 Hz, 1H), 7.66 (d, J=7.2 Hz, 1H), 7.35 (d, J=4.2 Hz, 1H), 7.27 (d, J=7.2 Hz, 1H), 7.25 (d, J=9.0 Hz, 2H), 6.76 (d, J=4.2 Hz, 2H), 6.69 (d, J=9.0 Hz, 2H), 4.81-4.77 (m, 1H), 4.13-4.08 (m, 2H), 4.05-3.97 (m, 3H), 3.81-3.78 (m, 1H), 3.74-3.70 (m, 1H), 3.65-3.61 (m, 1H)

LCMS: 482 (M+H$^+$) for C$_{23}$H$_{20}$ClN$_5$O$_3$S

EXAMPLE 30

Preparation of Compound (129)

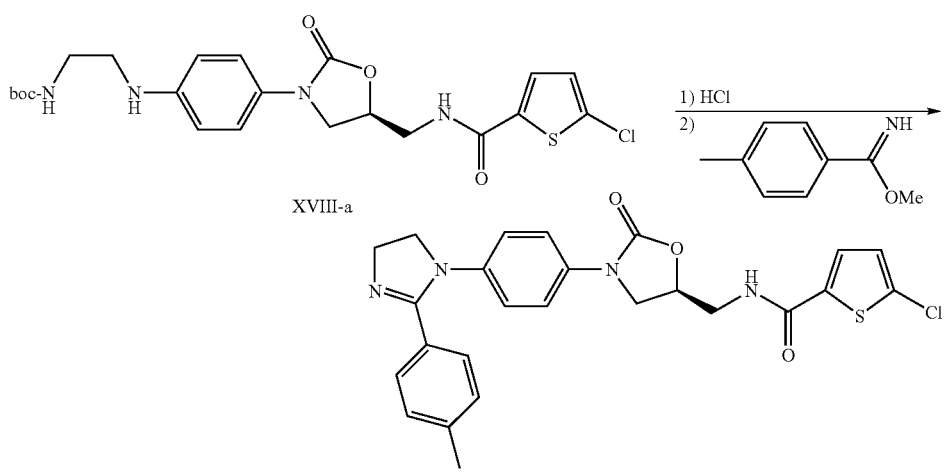

The title compound (129) was synthesized according to a similar procedure to Example 27.

$^1$H NMR (600 MHz, DMSO-d$_6$) δ=9.03 (t, J=6 Hz, 1H), 7.71 (d, J=4 Hz, 1H), 7.50 (d, J=9 Hz, 2H), 7.33 (d, J=7.8 Hz, 2H), 7.27 (d, J=7.8 Hz, 2H), 7.20 (d, J=4 Hz, 1H), 7.17 (d, J=9 Hz, 2H), 4.86-4.78 (m, 1H), 4.33 (t, J=9.6 Hz, 2H), 4.13 (t, J=9 Hz, 1H), 4.05 (t, J=10 Hz, 2H), 3.81 (dd, J=9, 6 Hz, 1H), 3.65-3.53 (m, 2H), 2.33 (s, 3H)

LCMS: 495 (M+H$^+$) for C$_{25}$H$_{23}$ClN$_4$O$_3$S

EXAMPLE 31

Preparation of Compound (130)

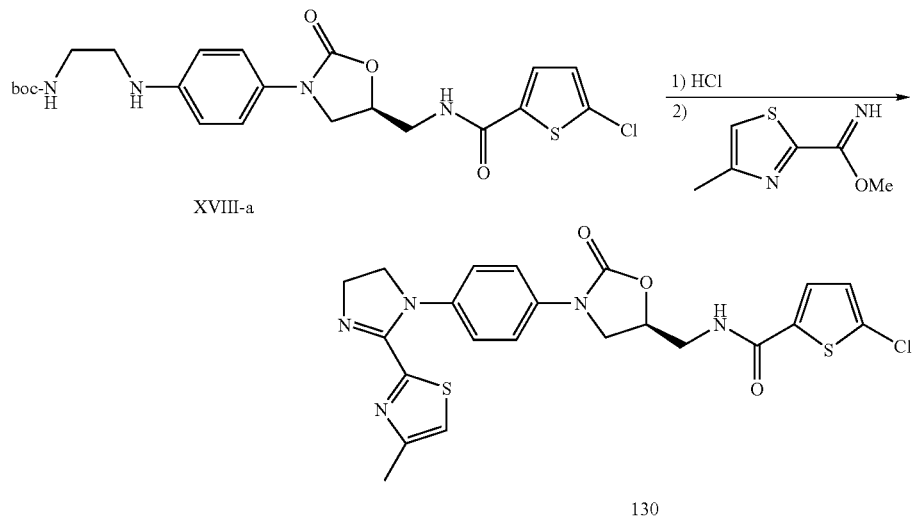

The title compound (130) was synthesized according to a similar procedure to Example 27.

$^1$H NMR (600 MHz, CDCl$_3$) δ=7.38 (d, J=9 Hz, 1H), 7.34 (d, J=4.2 Hz, 1H), 6.98 (t, J=6 Hz, 1H), 6.95 (d, J=1.2 Hz, 1H), 6.93 (d, J=9 Hz, 2H), 6.86 (d, J=4.2 Hz, 1H), 4.88-4.82 (m, 1H), 4.12-4.05 (m, 3H), 4.05-3.99 (m, 2H), 3.89-3.82 (m, 2H), 3.73 (dt, J=15, 6 Hz, 1H), 2.32 (s, 3H)

LCMS: 502 (M+H$^+$) for C$_{22}$H$_{20}$ClN$_5$O$_3$S$_2$

EXAMPLE 32

Preparation of Compound (131)

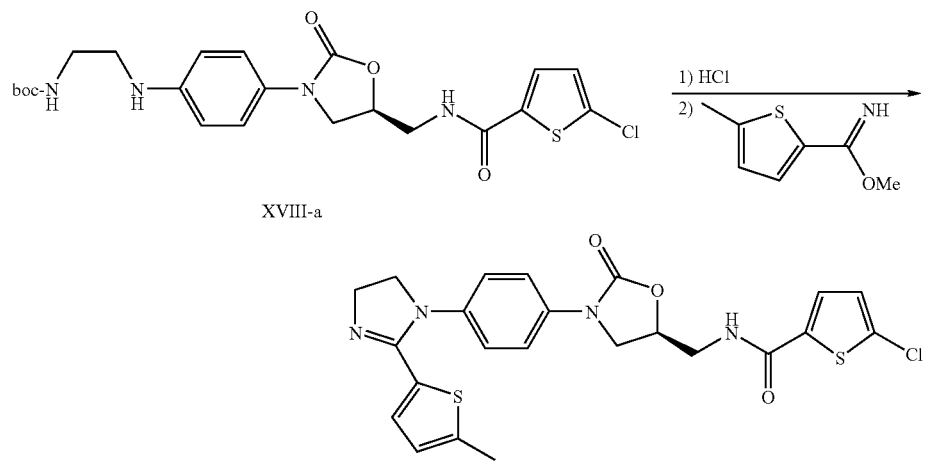

The title compound (131) was synthesized according to a similar procedure to Example 27.

$^1$H NMR (400 MHz, CDCl$_3$) δ=7.45 (d, J=8.8 Hz, 2H), 7.34 (d, J=4.0 Hz, 1H), 7.09 (d, J=8.8 Hz, 2H), 6.90 (d, J=4.0 Hz, 1H), 6.83 (d, J=4.0 Hz, 1H), 6.72 (t, J=5.6 Hz, 1H), 6.54 (d, J=4.0 Hz, 1H), 4.87-4.79 (m, 1H), 4.15-3.80 (m, 7H), 3.77-3.68 (m, 1H), 2.42 (s, 3H)

LCMS: 501 (M+H$^+$) for C$_{23}$H$_{21}$ClN$_4$O$_3$S$_2$

EXAMPLE 33

Preparation of Compound (132)

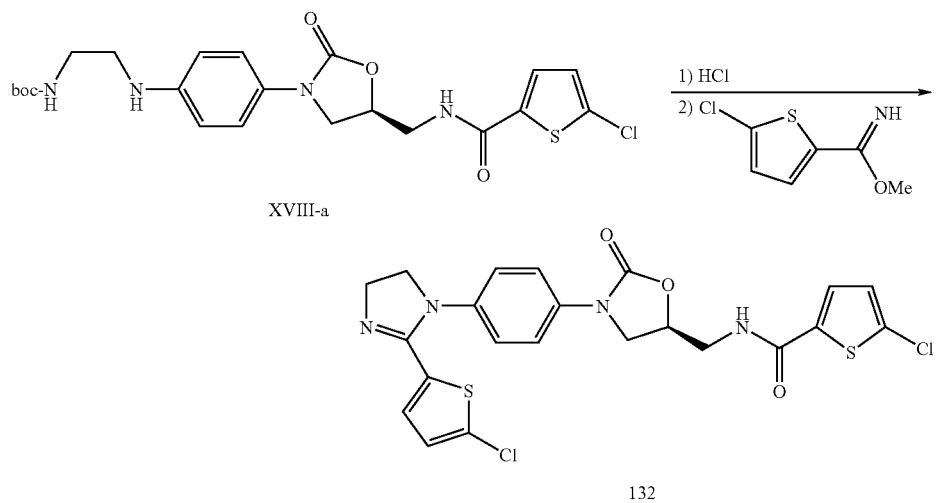

The title compound (132) was synthesized according to a similar procedure to Example 27.

$^1$H NMR (400 MHz, CDCl$_3$) δ=7.45 (d, J=8.8 Hz, 2H), 7.29 (d, J=4.0 Hz, 1H), 7.09 (t, J=8.8 Hz, 2H), 6.91 (d, J=4.0 Hz, 1H), 6.66 (d, J=4.0 Hz, 1H), 6.58 (d, J=4.0 Hz, 1H), 6.43 (t, J=6.0 Hz, 1H), 4.89-4.83 (m, 1H), 4.11 (t, J=9 Hz, 1H), 4.05-3.97 (m, 2H), 3.95-3.83 (m, 4H), 3.74 (dt, J=9, 6 Hz, 1H)

LCMS: 521 (M+H$^+$) for C$_{22}$H$_{18}$Cl$_2$N$_4$O$_3$S$_2$

EXAMPLE 34

Preparation of Compound (133)

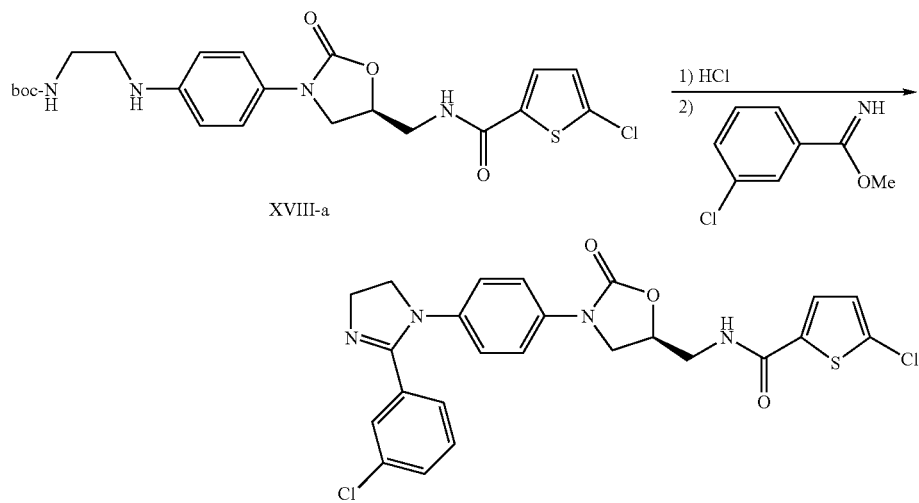

The title compound (133) was synthesized according to a similar procedure to Example 27.

$^1$H NMR (400 MHz, CDCl$_3$) δ=7.53 (s, 1H), 7.37-7.31 (m, 4H), 7.31-7.26 (m, 1H), 7.19 (t, J=8 Hz, 1H), 6.88 (d, J=4.4 Hz, 1H), 6.81 (d, J=8.8 Hz, 2H), 6.81-6.74 (br, 1H), 4.87-4.79 (m, 1H), 4.13-3.97 (m, 5H), 3.87 (ddd, J=14.8, 6.4, 3.2 Hz, 1H), 3.80 (dd, J=9.2, 6.4 Hz, 1H), 3.70 (dt, J=14.8, 6 Hz, 1H)

LCMS: 515 (M+H$^+$) for C$_{24}$H$_{20}$Cl$_2$N$_4$O$_3$S

EXAMPLE 35

Preparation of Compound (134)

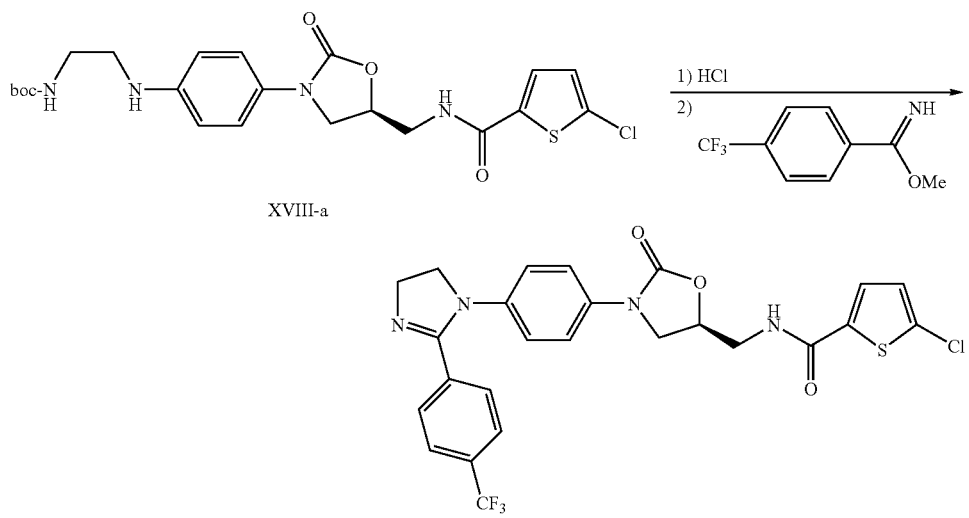

The title compound (134) was synthesized according to a similar procedure to Example 27.

$^1$H NMR (400 MHz, CDCl$_3$) δ=7.61 (d, J=8.0 Hz, 2H), 7.55 (d, J=8.0 Hz, 2H), 7.36 (d, J=8 Hz, 2H), 7.32 (d, J=3.6 Hz, 1H), 6.90 (d, J=3.6 Hz, 1H), 6.82 (d, J=8 Hz, 2H), 6.67 (t, J=6 Hz, 1H), 4.88-4.79 (m, 1H), 4.16-4.01 (m, 5H), 3.92-3.84 (m, 1H), 3.84-3.77 (m, 1H), 3.75-3.66 (m, 1H)

LCMS: 549 (M+H$^+$) for C$_{25}$H$_{20}$ClF$_3$N$_4$O$_3$S

EXAMPLE 36

Preparation of Compound (135)

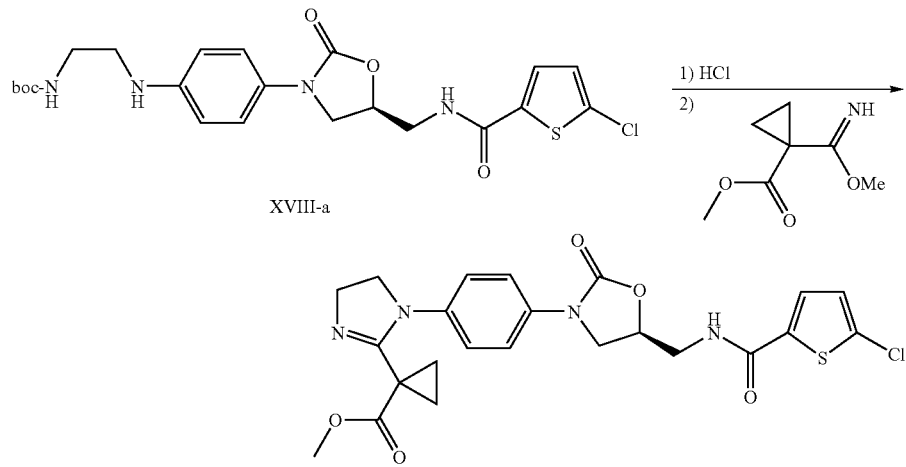

The title compound (135) was synthesized according to a similar procedure to Example 27.

$^1$H NMR (600 MHz, CDCl$_3$) δ=7.53 (d, J=9.0 Hz, 2H), 7.33 (d, J=4.2 Hz, 1H), 7.21 (d, J=9.0 Hz, 2H), 6.91 (d, J=4.2 Hz, 1H), 6.68 (t, J=6.0 Hz, 1H), 4.90-4.86 (m, 1H), 4.13-4.07 (m, 3H), 3.98-3.95 (m, 2H), 3.93-3.86 (m, 2H), 3.79-3.75 (m, 1H), 3.45 (s, 3H), 1.32-1.24 (m, 4H)

LCMS: 503 (M+H$^+$) for C$_{23}$H$_{23}$ClN$_4$O$_5$S

EXAMPLE 37

Preparation of Compound (136)

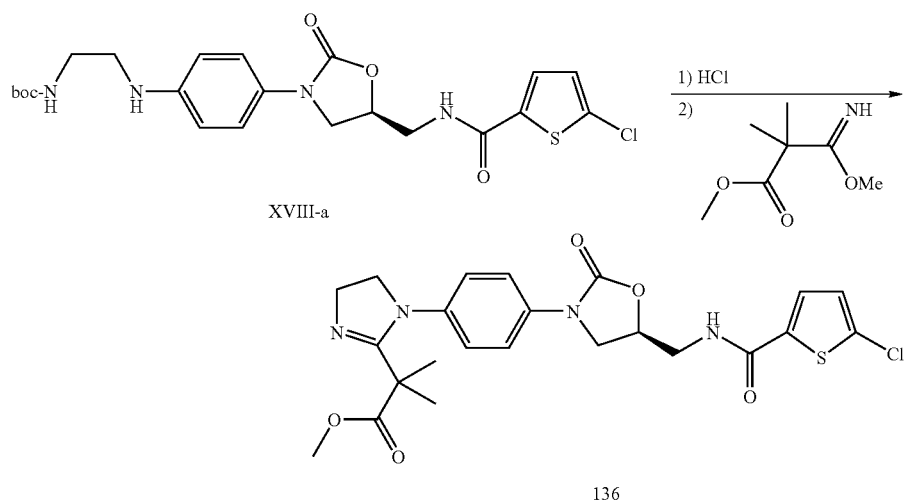

136

The title compound (136) was synthesized according to a similar procedure to Example 27.

$^1$H NMR (600 MHz, CDCl$_3$) δ=7.52 (d, J=8 Hz, 2H), 7.34-7.31 (m, 1H), 7.17 (d, J=8 Hz, 2H), 6.94-6.91 (m, 1H), 6.55 (t, J=6 Hz, 1H), 4.91-4.84 (m, 1H), 4.12 (t, J=9 Hz, 1H), 3.95-3.84 (m, 4H), 3.81-3.73 (m, 3H), 3.51 (s, 3H), 1.39 (s, 6H)

LCMS: 505 (M+H$^+$) for C$_{23}$H$_{25}$ClN$_4$O$_5$S

EXAMPLE 38

Preparation of Compound (137)

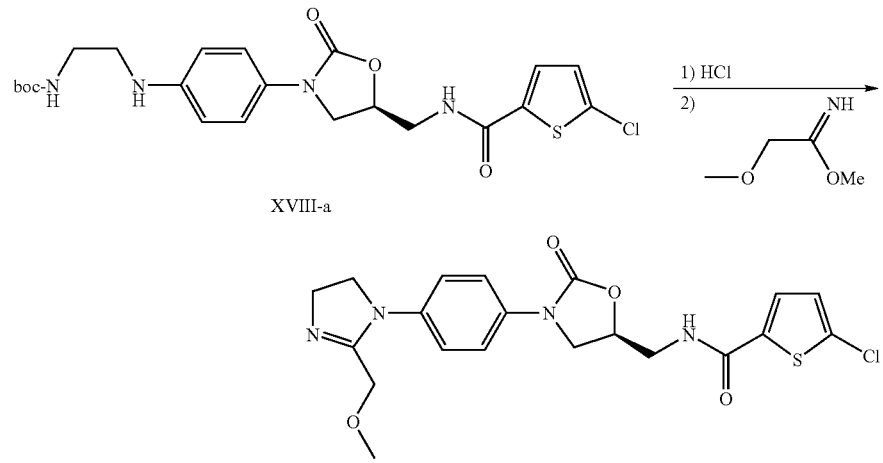

137

The title compound (137) was synthesized according to a similar procedure to Example 27.

$^1$H NMR (400 MHz, acetone-d$_6$) δ=8.49 (br, 1H), 7.77 (d, J=4 Hz, 2H), 7.58 (d, J=8.8 Hz, 2H), 7.28 (d, J=8.8 Hz, 2H), 7.06 (d, J=4 Hz, 1H), 4.94-4.87 (m, 1H), 4.23 (t, J=9.2 Hz, 1H), 4.14 (s, 2H), 4.06-4.00 (m, 1H), 3.95-3.88 (m, 3H), 3.85-3.73 (m, 4H), 3.31 (m, 3H)

LCMS: 449 (M+H$^+$) for C$_{20}$H$_{21}$ClN$_4$O$_4$S

EXAMPLE 39

Preparation of Compound (138)

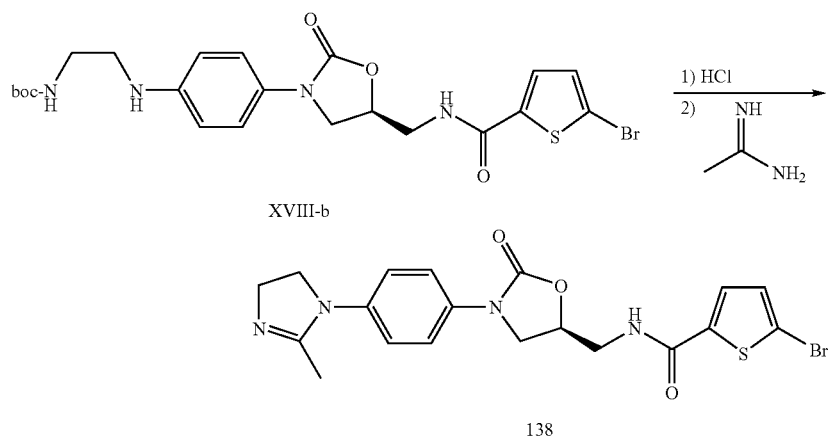

According to a similar procedure for Compound (XVIII-a) of Preparation Example 5, but using bromothiophene instead of chlorothiophene, obtained was Compound (XVIII-b). The title compound (138) was synthesized by using the compound (XVIII-b) according to the same procedure as Example 15.

$^1$H NMR (400 MHz, DMSO-d$_6$) δ=8.97 (br, 1H), 7.64 (d, J=4 Hz, 1H), 7.48 (d, J=9 Hz, 2H), 7.30 (d, J=4 Hz, 1H), 7.19 (d, J=9 Hz, 2H), 4.86-4.78 (m, 1H), 4.16 (t, J=8.8 Hz, 1H), 3.82 (dd, J=8.8, 6 Hz, 1H), 3.78-3.69 (m, 2H), 3.67-3.53 (m, 4H), 1.92 (s, 3H)

LCMS: 464 (M+H$^+$) for C$_{19}$H$_{19}$BrN$_4$O$_5$S

EXAMPLE 40

Preparation of Compound (139)

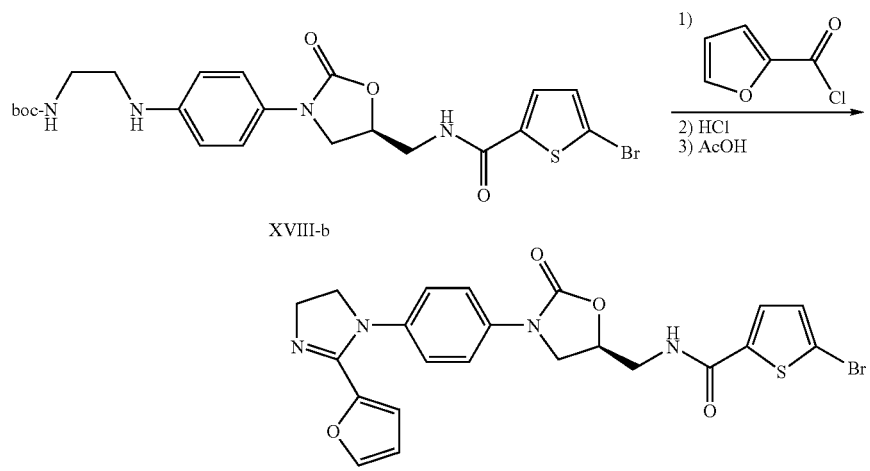

According to a similar procedure for Compound (XVIII-a) of Preparation Example 5, but using bromothiophene instead of chlorothiophene, obtained was Compound (XVIII-b). The title compound (139) was synthesized by using the compound (XVIII-b) according to the same procedure as Example 18.

$^1$H NMR (400 MHz, CDCl$_3$) δ=7.44 (d, J=8.8 Hz, 2H), 7.38 (d, J=4 Hz, 1H), 7.29 (d, J=4.0 Hz, 1H), 7.04 (d, J=4 Hz, 1H), 7.02 (d, J=8.8 Hz, 2H), 6.72 (t, J=6.0 Hz, 1H), 6.37 (d, J=3.6 Hz, 1H), 6.33 (dd, J=3.6, 2 Hz, 1H), 4.90-4.83 (m, 1H), 4.14-4.03 (m, 3H), 3.94-3.84 (m, 4H), 3.75 (dt, J=14.4, 6 Hz, 1H)

LCMS: 516 (M+H$^+$) for C$_{22}$H$_{19}$BrN$_4$O$_4$S

EXAMPLE 41

Preparation of Compound (140)

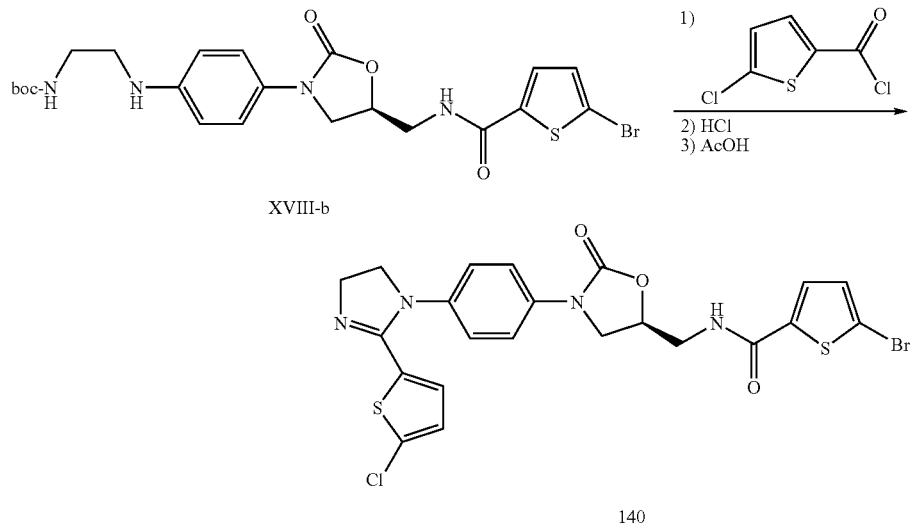

According to a similar procedure for Compound (XVIII-a) of Preparation Example 5, but using bromothiophene instead of chlorothiophene, obtained was Compound (XVIII-b). The title compound (140) was synthesized by using the compound (XVIII-b) according to the same procedure as Example 18.

$^1$H NMR (400 MHz, CDCl$_3$) δ=7.46 (d, J=8.8 Hz, 2H), 7.28 (d, J=4 Hz, 1H), 7.09 (d, J=8.8 Hz, 2H), 7.04 (d, J=4 Hz, 1H), 6.67 (d, J=4 Hz, 1H), 6.62 (t, J=6.4 Hz, 1H), 6.59 (d, J=4 Hz, 1H), 4.91-4.83 (m, 1H), 4.12 (t, J=9 Hz, 1H), 4.05-3.98 (m, 2H), 3.94-3.84 (m, 4H), 3.75 (dt, J=14.4, 6 Hz, 1H)

LCMS: 566 (M+H$^+$) for C$_{22}$H$_{18}$BrClN$_4$O$_4$S$_2$

EXAMPLE 42

Preparation of Compound (141)

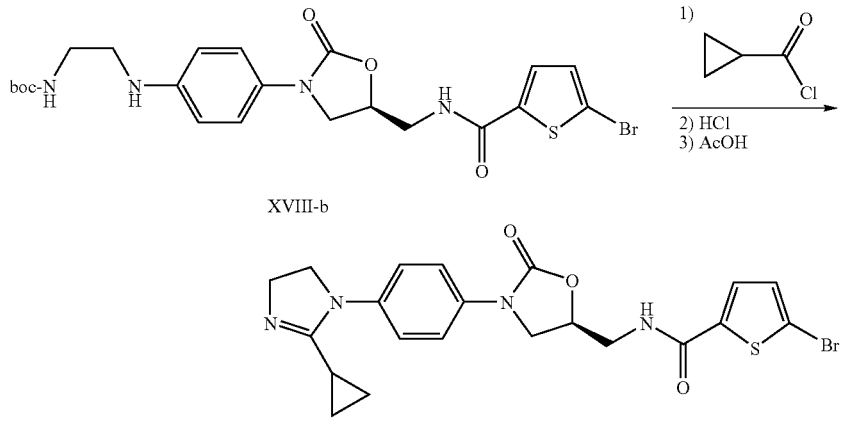

According to a similar procedure for Compound (XVIII-a) of Preparation Example 5, but using bromothiophene instead of chlorothiophene, obtained was Compound (XVIII-b). The title compound (141) was synthesized by using the compound (XVIII-b) according to the same procedure as Example 18.

$^1$H NMR (600 MHz, CDCl$_3$) δ=7.57 (d, J=9 Hz, 2H), 7.31 (d, J=4.2 Hz, 1H), 7.29 (d, J=9 Hz, 2H), 7.04 (d, J=4.2 Hz, 1H), 6.80 (t, J=6 Hz, 1H), 4.92-4.86 (m, 1H), 4.14 (t, J=9 Hz, 1H), 3.94-3.86 (m, 2H), 3.82-3.74 (m, 2H), 2.81 (t, J=6.6 Hz, 2H), 1.30-1.22 (m, 1H), 1.02-0.96 (m, 2H), 0.64-0.58 (m, 2H)

LCMS: 490 (M+H$^+$) for C$_{21}$H$_{21}$BrN$_4$O$_3$S

EXAMPLE 43

Preparation of Compound (142)

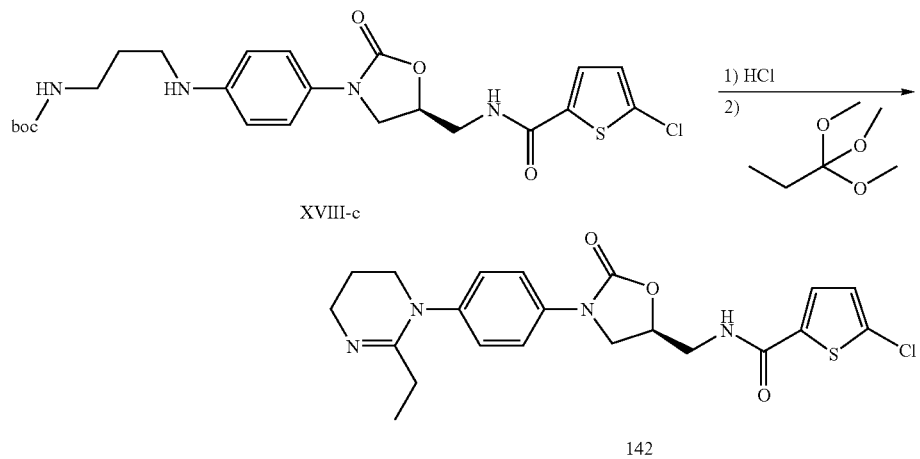

According to a similar procedure for Compound (XVIII-a) of Preparation Example 5, but using N-boc-3-aminopropanaldehyde instead of N-Boc-2-aminoacetaldehyde, obtained was Compound (XVIII-c). The title compound (142) was synthesized by using the compound (XVIII-c) according to the same procedure as Example 17.

$^1$H NMR (400 MHz, DMSO-d$_6$) δ=10.17 (s, 1H), 9.14-9.07 (m, 1H), 7.77-7.65 (m, 3H), 7.56-7.50 (m, 2H), 7.22-7.18 (m, 1H), 4.91-4.83 (m, 1H), 4.21 (t, J=9 Hz, 1H), 3.95-3.88 (m, 1H), 3.70-3.55 (m, 4H), 3.45-3.40 (m, 2H), 2.25 (q, J=7.6 Hz, 2H), 2.15-2.05 (m, 2H), 0.98 (t, J=7.6 Hz, 3H)

LCMS: 447 (M+H$^+$) for C$_{21}$H$_{23}$ClN$_4$O$_3$S

EXPERIMENTAL EXAMPLE 1

Analysis of Inhibiting Activity of Factor Xa Inhibitor

In order to determine the factor Xa inhibiting activity of the oxazolidinone derivatives with cyclic amidines, represented by Chemical Formula (1) according to the invention, IC$_{50}$ value (concentration of the compound to inhibit 50% of the enzyme activity) (it is associated with inhibiting constant Ki) was measured and evaluated. Relative rate of hydrolysis (as compared to control group without inhibition) was plotted versus logarithm of the concentration of the oxazolidinone derivative with a cyclic amidine represented by Chemical Formula (1) according to the invention, to obtain the concentration of the inhibitor for 50% decrease in the rate of hydrolysis of the substrate.

The factor Xa inhibiting activity for an oxazolidinone derivative with a cyclic amidine group represented by Chemical Formula (1) according to the invention was determined by calculating the inhibition constant Ki according to Equation (1), as described in Chen and Prusoff, Biochem. Pharmacol. (1973) 22, 3099-3108:

$$Ki=IC_{50}/\{1+([S]/Km)\} \qquad \text{[Equation 1]}$$

wherein, Km is Michaelis-Menten constant, exhibiting concentration of the substrate at the half of the maximum rate of the enzyme reaction, and IC$_{50}$ represents concentration of the inhibitor for 50% decrease in the rate of hydrolysis of the substrate.

Since the inhibition constant Ki represents the level of inhibition by the enzyme and the factor Xa inhibitor compound, lower dissociation constant implies stronger binding of the inhibitor to the enzyme, and thus higher inhibiting activity. The inhibition constant can be obtained by spectrophotometry whereby the color development is determined as a function of time, after being reacted with a specific substrate which develops color upon hydrolysis caused by action of factor Xa.

1) Reagents and Materials

Chromogenic substrate, S-2765(N-Z-D-Arg-Gly-Arg-pNA.2HCl required for measurement of factor Xa activity was purchased from Chromogenics. Factor Xa enzyme was purchased from Enzyme Research Laboratories, and a 96-well plate for microfactor was purchased from Costar.

2) Inhibition Activity of Factor Xa Inhibitor

The inhibition activity of the compounds of the present invention against factor Xa activity was determined according to the following description.

In each well of a 96-well plate, added was 50 μL of 160 mM Tris buffer solution (pH 7.8) containing 240 mM NaCl and 0.16% PEG-8000 (polyethyleneglycol, molecular weight: about 8,000). For the inhibitor solution, the inhibitor compound according to the present invention was diluted with dimethylsulfoxide (DMSO) in 10 mM, and then further diluted with third-distilled water (finally 10% DMSO solution), and the solution (10 μL) was added to each well. For the substrate solution, S-2765 was dissolved in third-distilled water in a concentration of 10 mM, and the solution was diluted with 100 mM Tris-HCl buffer (pH 7.8) containing 150 mM of NaCl and 0.1% PEG 8000, immediately before use, to give a concentration of 1.5 mM. The substrate solution (20 μL) thus prepared was added to each well.

To each well containing the reaction solution, added was a solution of factor Xa (20 µL) dissolved in 100 mM Tris buffer (pH 7.8) containing 150 mM NaCl and 0.1% PEG-8000, in a concentration of 13 nM, to initiate hydrolysis by the enzyme. Kinetic analysis of the reaction was performed by a kinetic plate reader (Molecular Devices, Spectramax 190) at 37° C. for 20 minutes. After adding S-2765 chromogenic substrate, the amount of p-nitroanilide generated from the reaction was monitored by means of change of absorbance at 405 nm for 5 minutes.

Relative rate of hydrolysis (compared to control group without inhibition) versus logarithm of the oxazolidinone derivative with a cyclic amidine group (Chemical Formula I) was plotted to obtain the concentration of the inhibitor to decrease the rate of hydrolysis of the substrate by 50%. GraFit (version 5.0.12) program for statistical process purchased from Erithacus Software was employed.

When inhibition constant Ki is calculated, it can be calculated according to Equation (1). In the equation, Km value used is 125 µM, which was obtained by alteration of substrate concentration at a constant enzyme concentration.

EXPERIMENTAL EXAMPLE 2

Effects on Blood Coagulation

The effect of oxazolidinone derivatives with cyclic amidines represented by Chemical Formula (1) according to the invention on blood coagulation was compared by measuring PT (prothrombin time) and aPTT (activated Partial Thromboplastin Time). The procedure of measurement is described below.

1) Measurement of PT

Citrated plasma was purchased from Daejeon-Chungnam Blood Institute (located at Daejeon, Korea). A compound solution (5 µL) according to the invention (in a various concentration gradient, 5% DMSO solution) was added to the plasma (45 µm), and the reaction was carried out at 37° C. for 5 minutes. STA-Neoplastine (Diagnostica Stago) (100 µL) was then added thereto, and the duration for plasma coagulation was measured. The duration for plasma coagulation is determined as the point when the absorbance at 340 nm reaches 0.1.

2) Measurement of aPTT

A solution (5 µL) of the oxazolidinone derivative with cyclic amidine group represented by Chemical Formula (1) according to the invention (in a various concentration gradient, 5% DMSO solution) was added to the plasma (45 µm), and the reaction was carried out at 37° C. for 2 minutes. STA-PTT (Diagnostica Stago) (50 µL) was then added thereto. After the reaction at 37° C. for additional 5 minutes, 25 mM $CaCl_2$ (50 µL) was added thereto, and the duration for plasma coagulation was measured. The duration for plasma coagulation was determined as the point when the absorbance at 340 nm reaches 0.1.

3) Determination of % Inhibition Against Thrombus Formation by Means of Arteriovenous Shunt Model (in vitro) in White Rats Antithrombotic effect of the compounds according to the present invention was evaluated by using arteriovenous shunt model in white rats. The animals used were male Sprague Dawleys with the body weight of 200-250 g. For one day before the experiment, the animals were fasted. Five to six animals were used for each test group. The compound of Example was orally administered 1 hour before opening of the shunt. The rats were anesthetized by abdominal administration of Rompun (Bay HealthCare) and Chloral hydrate or urethane in an amount of 12 and 50 mg per kg of the body weight. Into the left carotid artery and right jugular vein of the white rat, a polyethylene(PE)-60 tubing filled with physiological saline was inserted and secured. Both ends of individual PE tubing were connected to a silicone tubing having a length of 5 cm in which a cotton thread have been incorporated diagonally, and the shunt was open to provide circulation for 15 minutes. The shunt was then compressed by using jaws, and the cotton thread was carefully removed and the thrombus generated was weighed. The % inhibition of thrombus formation was calculated by using the weight of thrombus obtained from white rats of the control group to which a solution of oral administration was administered.

The factor Xa inhibition constant, and PT, aPTT and % inhibition values determined according to the method described above are shown in Table 1. As the control substance, Rivaroxaban (Chemical Formula A) was used.

TABLE 1

Factor Xa inhibition constant and % inhibition of blood coagulation of the compounds represented by Chemical Formula (1)

[Chemical Formula A]

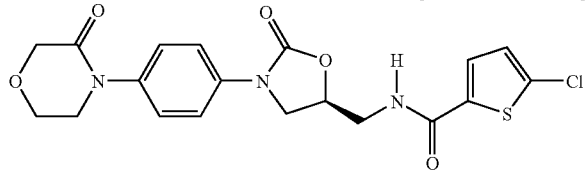

| Compound | Ki (nM) | PT | APTT | % Inhibition |
|---|---|---|---|---|
| Rivaroxaban | 0.76 | 0.09 | 0.39 | 83 |
| 100 | 47.05 | 0.22 | 2.29 | 40 |
| 101 | 2.97 | 0.05 | 0.22 | 2 |
| 102 | 3.43 | 0.04 | 0.17 | 26 |
| 106 | 13.07 | 0.09 | 0.55 | 0 |
| 107 | 5.70 | 0.09 | 0.28 | 50 |
| 108 | 2.42 | 0.03 | 0.15 | 30 |
| 109 | 4.67 | 0.05 | 0.19 | 26 |
| 110 | 4.40 | 0.03 | 0.19 | 38 |
| 111 | 10.50 | 0.03 | 0.28 | 49 |
| 112 | 4.05 | 0.05 | 0.19 | 26 |
| 113 | 9.19 | 0.11 | 0.35 | 53 |
| 114 | 2.45 | 0.03 | 0.12 | 41 |
| 115 | 1.29 | 0.34 | 2.61 | ND |
| 116 | 3.46 | 0.05 | 0.18 | 65 |
| 117 | 3.18 | 0.04 | 0.29 | 68 |
| 118 | 69.90 | 0.58 | ND | ND |
| 119 | 3.70 | 0.03 | ND | 4 |
| 120 | 27.95 | 0.31 | ND | 37 |
| 121 | 1.81 | 0.06 | ND | 35 |
| 123 | 0.39 | 0.07 | 0.26 | 71 |
| 124 | 1.71 | 0.07 | 0.26 | 52 |
| 125 | 2.33 | 0.05 | ND | 42 |
| 126 | 12.80 | 0.16 | ND | 22 |
| 127 | 6.14 | 0.12 | ND | 27 |
| 128 | 13.90 | 0.95 | ND | 22 |
| 129 | 0.92 | 0.30 | ND | 0 |
| 130 | 8.60 | 0.94 | ND | 15 |
| 131 | 0.69 | 0.08 | 0.39 | 0 |
| 132 | 1.09 | 0.29 | 0.88 | 60 |
| 133 | 1.21 | 0.26 | ND | 44 |
| 134 | 4.01 | 0.36 | ND | 4 |
| 135 | 31.50 | 0.15 | 1.34 | 62 |
| 136 | 1.78 | 0.10 | ND | 31 |
| 138 | 2.38 | 0.04 | 0.16 | 27 |
| 139 | 1.47 | 0.07 | 0.47 | 60 |
| 140 | 2.63 | 0.24 | ND | 40 |
| 142 | 2.52 | 0.04 | 0.17 | 47 |

*ND: not determined

As can be seen from Table 1, the oxazolidinone derivatives with cyclic amidines represented by Chemical Formula (1)

according to the present invention showed higher Ki value than that of Rivaroxaban (the control), but frequently lower PT values. As explained above, though factor Xa catalyzes conversion of prothrombin to thrombin, it is prothrombinase complex which practically plays a critical role in blood coagulation in vivo, so that the inhibition of the complex eventually results in the effect of inhibiting blood coagulation. Thus, PT value rather than Ki value is directly associated with % inhibition of blood coagulation. Accordingly, the oxazolidinone derivatives with cyclic amidines represented by Chemical Formula (1) according to the invention might have better effect of inhibiting blood coagulation than the control substance, Rivaroxaban. Further, it is proved that the oxazolidinone derivatives according to the invention exhibit comparable level of pharmacological effect to that of Rivaoxaban (the control substance) from the experiments for determination of % inhibition of thrombus formation by using arteriovenous shunt model in white rats. Therefore, a compound having similar pharmacological activity to that of Rivaoxaban with controlling side effects, particularly increased bleeding, can make a better medicine than Rivaroxaban. The compounds of the present invention can be converted into their salts by using an acid such as HCl, due to high basicity of cyclic amidines, thereby significantly increasing the aqueous solubility.

EXPERIMENTAL EXAMPLE 3

Determination of Aqueous Solubility and Plasma Protein Binding

The aqueous solubility and plasma protein binding of the oxazolidinone derivatives with cyclic amidines represented by Chemical Formula (1) according to the invention were determined according to the following procedures.

1) Determination of Aqueous Solubility

To each well of a multiscreen solubility 96 well plate (Millipore), added was 100 mM potassium phosphate buffer (pH 7.4) (190 µL), and solution (10 mM) of a compound according to the present invention in DMSO (10 µL) was added to make the final concentration of 500 µM (5% DMSO). The plate was agitated at ambient temperature for 90 minutes with a rate of 225 rpm. After agitation, the content of the plate was filtered with application of pressure. The filtrate (160 µL) was individually transferred to a uv-96 well plate (Costar), and mixed with 40 µL of acetonitrile, and then agitated at ambient temperature for 10 minutes with a rate of 225 rpm. By means of a plate reader (Molecular Devices, Spectramax 190), absorbances at the wavelengths of 280, 300, 320, 340, 360 and 800 nm were measured. As a reference solution, employed was 100 mM potassium phosphate buffer (pH 7.4) containing 20% acetonitrile added by 10 mM DMSO solution (8 µL). The aqueous solubility was calculated by subtracting absorbance at 800 nm from total sum of absorbances at 280, 300, 320, 340 and 360 nm of the sample and the reference solution.

2) Determination of Plasma Protein Binding

Citrated plasma was purchased from Daejeon-Chungnam Blood Institute (located at Daejeon, Korea). A compound solution (500 µM in DMSO) (10 µL), according to the invention Was added to the plasma (1 mL), and the reaction was carried out at 37° C. and 120 rpm for 60 minutes. To three wells of Ultracel-10 filter plate (Millipore), the reaction solution was transferred (300 µL each). Then, the plasma solution (70 µL) was taken, and the total concentration of the compound was quantified by means of LC-MS/MS (API3000, ABI). After centrifuging the Ultracel-10 filter plate at 37° C. and 2000×g for 45 minutes, the filtrate was taken to determine the concentration of the compound which was not bound to the plasma protein.

Percentage of plasma protein binding was obtained via Equation (2):

% Protein binding=(1−concentration of compound in filtrate/concentration of compound in entire solution)×100%

Free=100−% Protein binding    [Equation 2]

The aqueous solubility and protein binding (%) determined according to the procedure described above are shown in Table 2. Rivaroxaban (Chemical Formula A) was used as a control substance.

TABLE 2

Solubility and protein binding of compounds represented by Chemical Formula (1)

[Chemical Formula A]

| Compound | Solubility (µM) | Plasma protein binding (% Free) |
|---|---|---|
| Rivaroxaban | 50 | 9 |
| 100 | 441 | 17 |
| 101 | 434 | 23 |
| 102 | 462 | 28 |
| 107 | 411 | 31 |
| 117 | 484 | 17 |
| 123 | 474 | 3 |

As can be seen from Table 2, the oxazolidinone derivatives with cyclic amidines represented by Chemical Formula (1) according to the invention have at least 8 times of solubility as compared to that of Rivaroxaban, with at least 20% reduction of protein binding. These results suggest that the oxazolidinone derivatives with cyclic amidines represented by Chemical Formula (1) according to the invention may exhibit better pharmacological activity when they are clinically used in an animal's body. Since the cyclic amidines are present in the form of salts with high solubility, the oxazolidinone derivatives with cyclic amidines represented by Chemical Formula (1) according to the invention have high favorableness to be employed as oral or injectable preparations.

[Industrial Applicability]

The novel oxazolidinone derivatives with cyclic amidine groups according to the present invention exhibit higher Ki values than that of Rivaroxaban, with lower PT and APTT values, thereby providing even higher clinical effect of inhibiting blood coagulation. Furthermore, having far higher aqueous solubility than Rivaroxaban, the compounds according to the invention can be favorably developed as oral or injectable preparations.

The invention claimed is:

1. An oxazolidinone derivative with a cyclic amidine, represented by Chemical Formula (1), or optical isomers and pharmaceutically acceptable salts thereof:

Chemical Formula 1

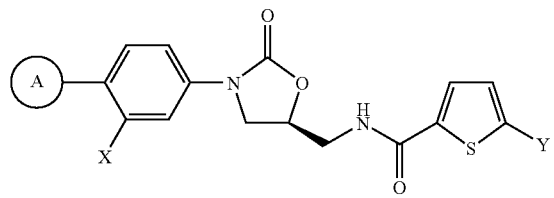

wherein, A is selected from the following structures:

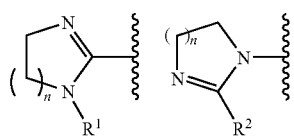

X represents hydrogen or halogen;

Y represents halogen;

$R^1$ and $R^2$ independently represent hydrogen, $(C_1-C_7)$ alkyl, $(C_3-C_{12})$cycloalkyl, a 5- to 7-membered heterocycloalkyl containing one or more heteroatom(s) selected from N, O and S, $(C_1-C_7)$alkyl containing one or more heteroatom(s) selected from N, O and S, $(C_6-C_{12})$aryl, $(C_4-C_{12})$heteroaryl, $-(CR^{11}R^{12})_mCO-R^{13}$, $-(CR^{11}R^{12})_mSO_2-R^{14}$ or $-(CR^{11}R^{12})_mCR^{21}=CR^{22}R^{23}$; and the alkyl, cycloalkyl, aryl or heteroaryl of $R^1$ and $R^2$ may be further substituted by one or more substituent(s) selected from $(C_1-C_7)$alkyl, halo$(C_1-C_7)$alkyl, $(C_1-C_7)$alkoxy and halogen;

$R^{11}$ and $R^{12}$ independently represent hydrogen or $(C_1-C_7)$ alkyl, or they may be linked via $(C_2-C_5)$alkylene to form a ring;

$R^{13}$ and $R^{14}$ independently represent hydrogen, $(C_1-C_7)$ alkyl or $(C_1-C_7)$alkoxy;

$R^{21}$ through $R^{23}$ independently represent hydrogen or $(C_1-C_7)$alkyl, m represents an integer from 0 to 3; and n represents an integer from 1 to 3.

2. An oxazolidinone derivative with a cyclic amidine group according to claim 1, which is represented by Chemical Formula (2) or (3), or optical isomers and pharmaceutically acceptable salts thereof:

Chemical Formula 2

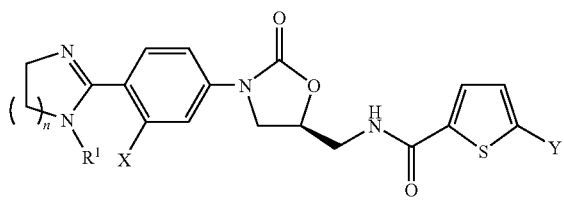

Chemical Formula 3

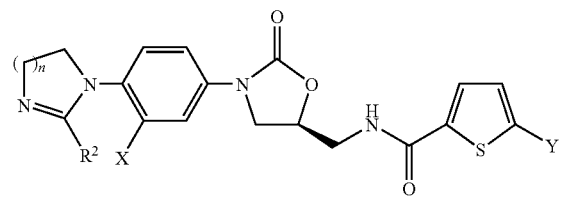

wherein, $R^1$ and $R^2$ are defined as in Chemical Formula (1) of claim 1;

X represents hydrogen, F or Cl;

Y represents Cl or Br; and n is an integer of 1 or 2.

3. An oxazolidinone derivative with a cyclic amidine group according to claim 2, wherein $R^1$ and $R^2$ independently represent hydrogen, methyl, ethyl, n-propyl, i-propyl, n-butyl, i-butyl, t-butyl, cyclopropyl, cyclobutyl, allyl, methylcarbonyl or methylsulfonyl, or a substituent selected from the following structures; and n is 1 or 2, or optical isomers and pharmaceutically acceptable salts thereof:

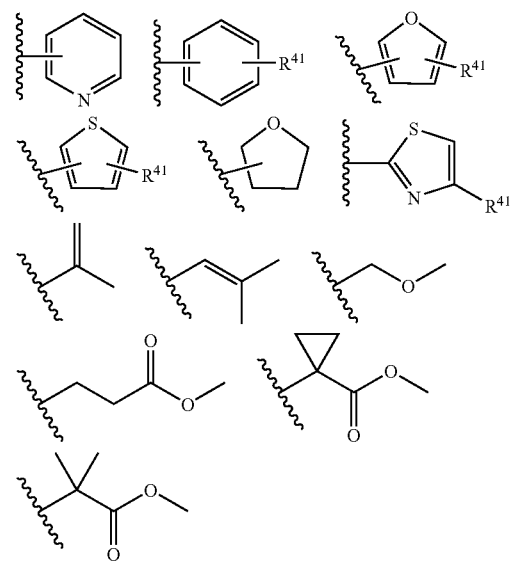

wherein, $R^{41}$ represents hydrogen, $(C_1-C_7)$alkyl, halo$(C_1-C_7)$alkyl or halogen.

4. An oxazolidinone derivative with a cyclic amidine group according to claim 1, which is selected from the following compounds, or optical isomers and pharmaceutically acceptable salts thereof:

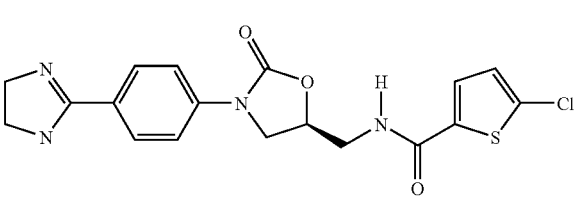

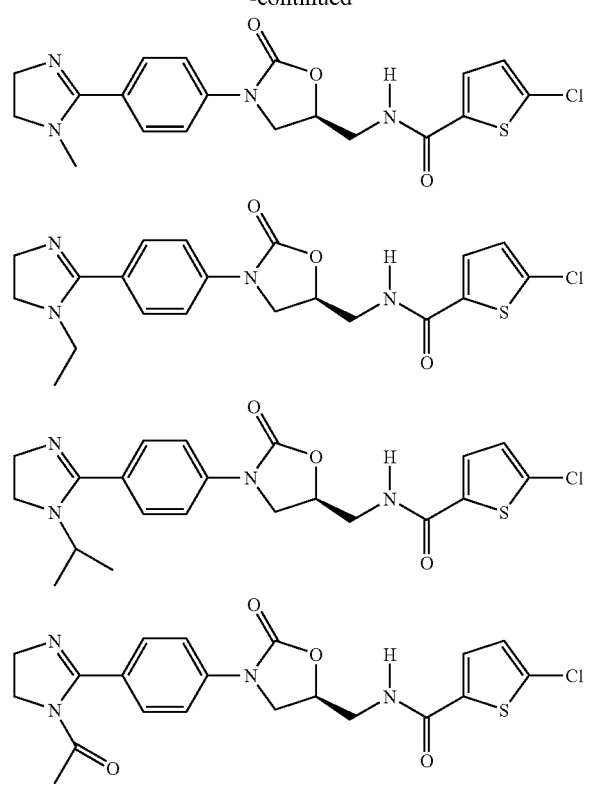
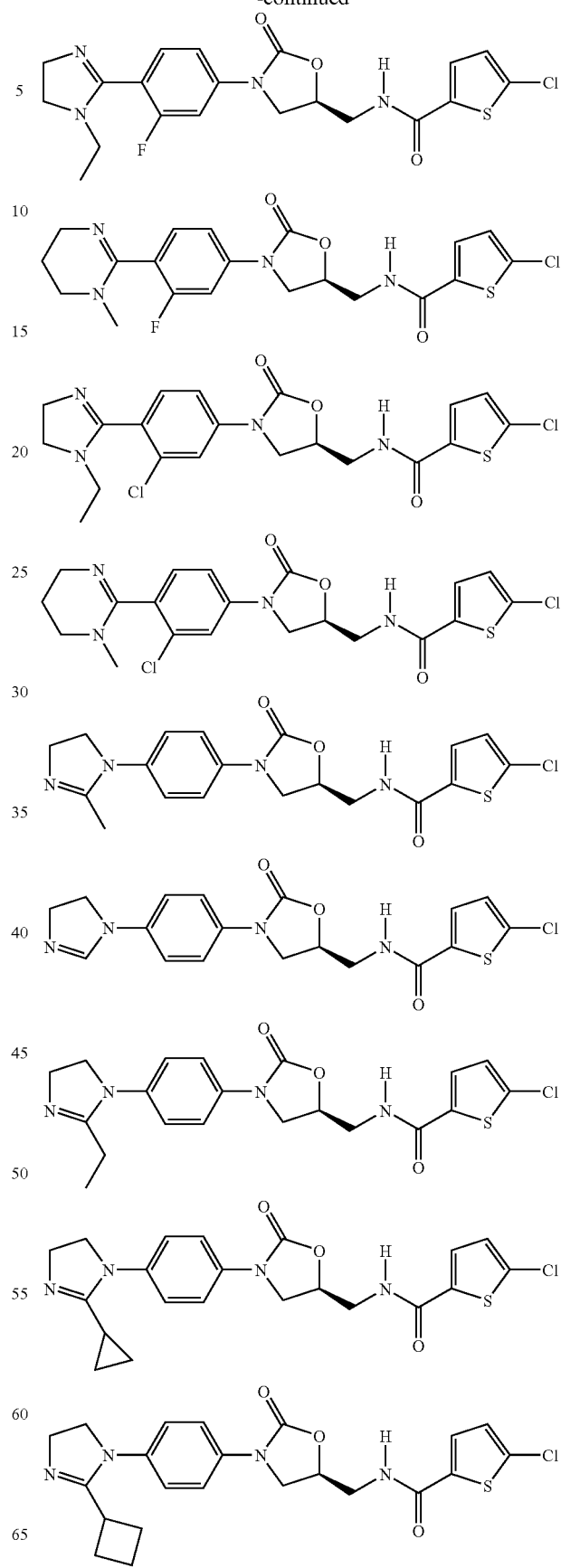

85
-continued
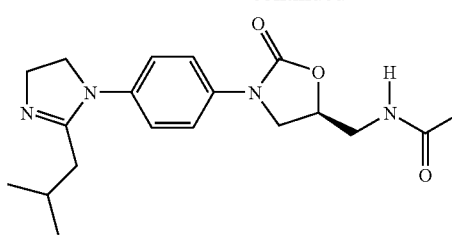
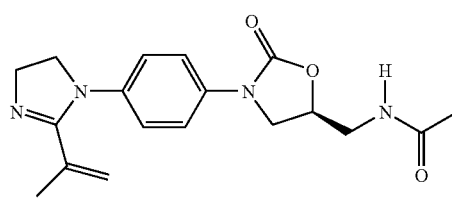
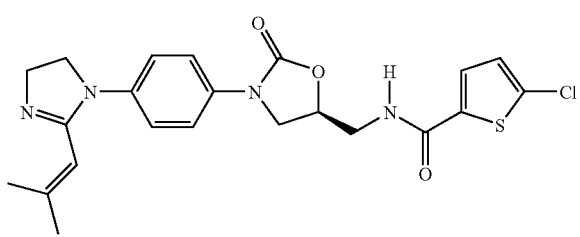
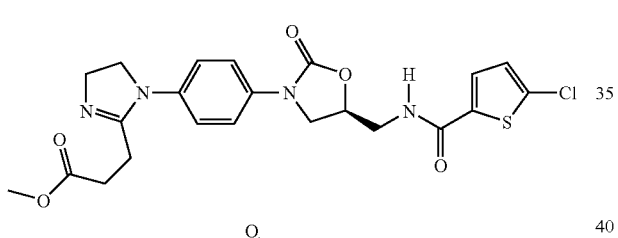
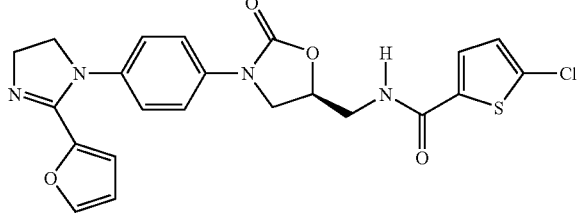
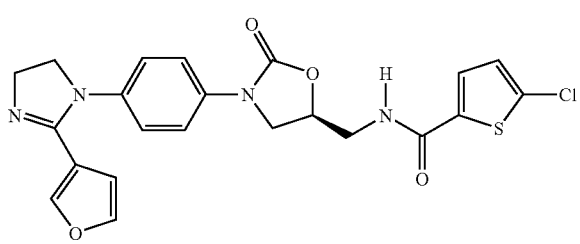
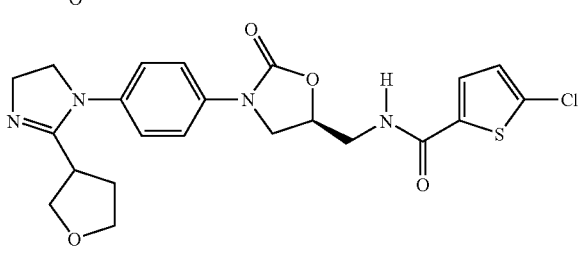
86
-continued
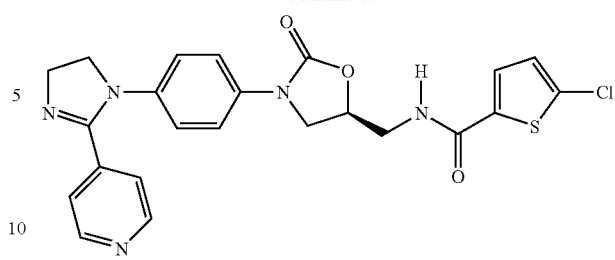
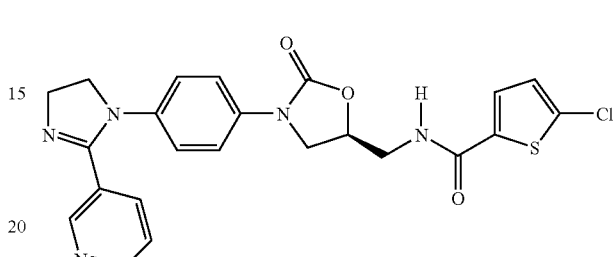
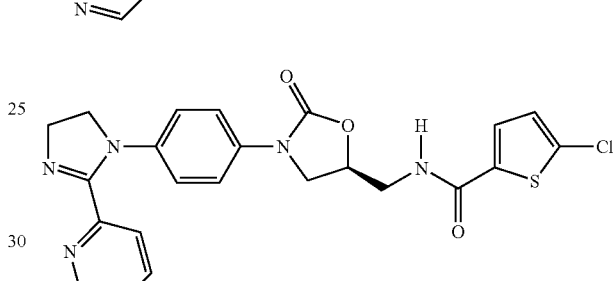
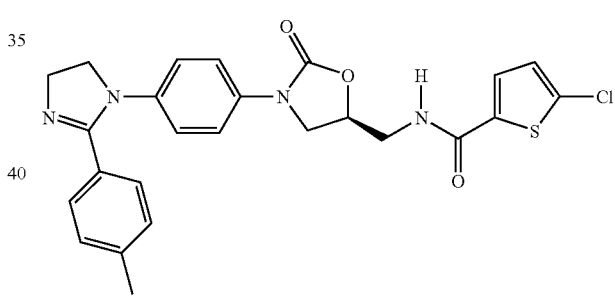
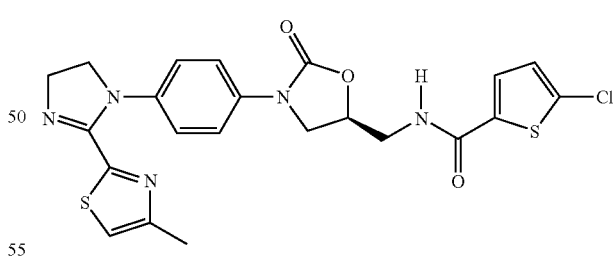
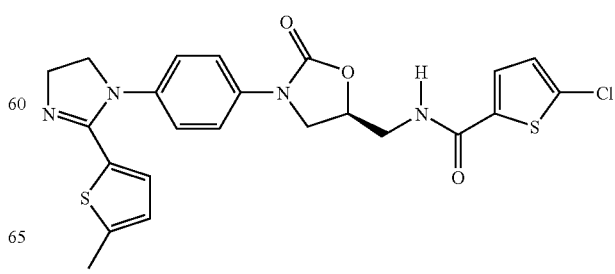

-continued

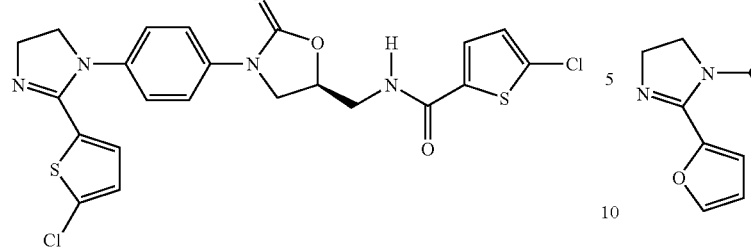

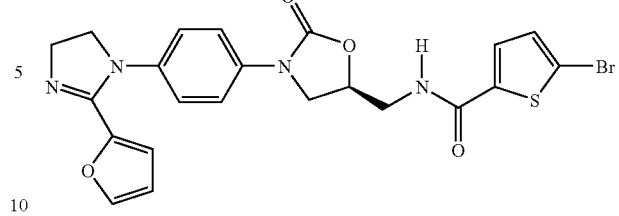

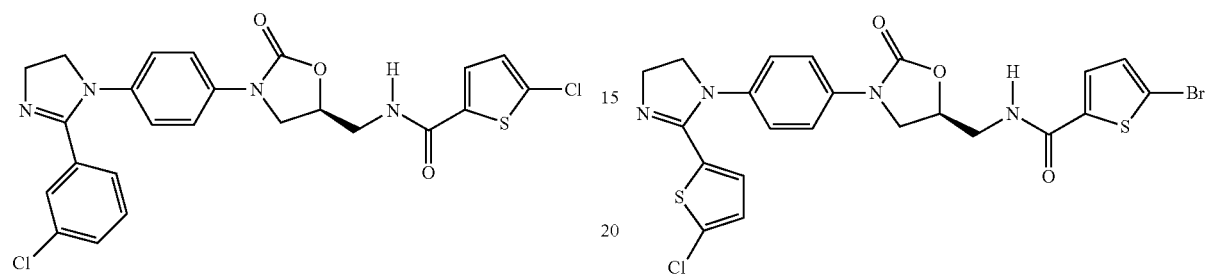

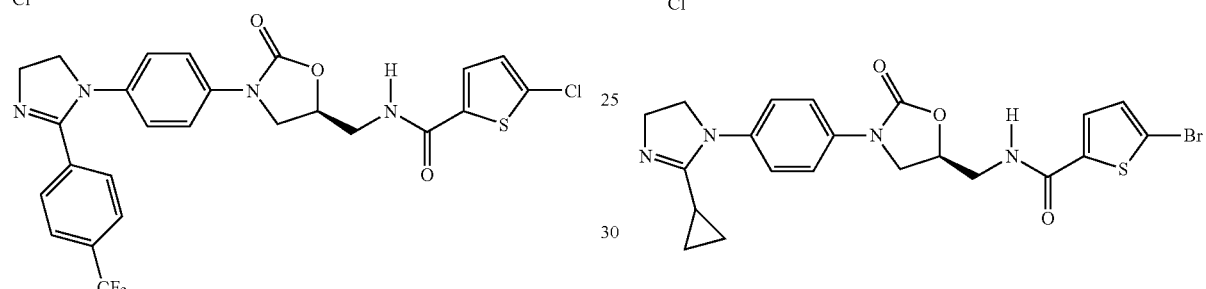

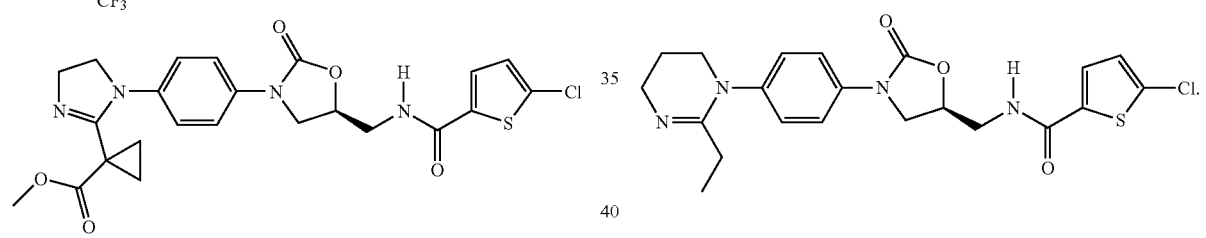

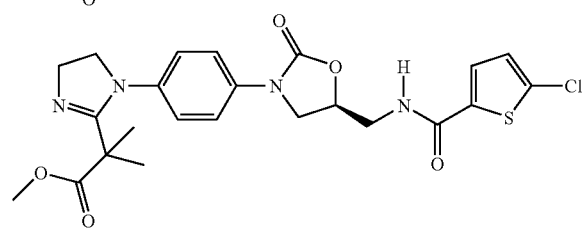

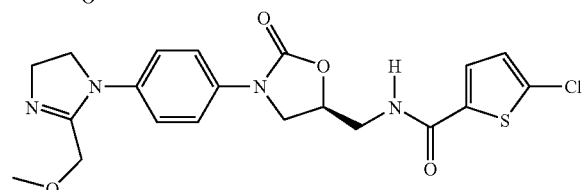

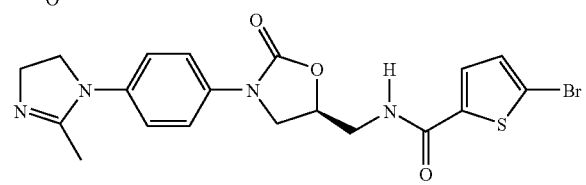

5. A pharmaceutical anticoagulant composition comprising an oxazolidinone derivative with a cyclic amidine group according to claim 1, as an active ingredient.

6. A pharmaceutical composition comprising an oxazolidinone derivative with a cyclic amidine group according to claim 1, for treating thrombosis, myocardial infarction, arteriosclerosis, inflammation, apoplexy, angina pectoris, recurrent stricture, intermittent claudication, phlebothrombosis, pulmonary embolism, arterial thrombosis, myocardial ischemia or thromboembolism.

7. A pharmaceutical composition comprising an oxazolidinone derivative with a cyclic amidine group according to claim 1 in combination with a thrombolytic drug, for treating diseases in coronary, cerebral or peripheral arteries.

8. An anticoagulant composition comprising an oxazolidinone derivative with a cyclic amidine group according to claim 1, for preserving blood, plasma or blood products in vitro.

* * * * *